(12) United States Patent
Bai et al.

(10) Patent No.: US 9,761,047 B2
(45) Date of Patent: *Sep. 12, 2017

(54) VIRTUAL MASK FITTING SYSTEM

(71) Applicant: Honeywell International Inc., Morris Plains, NJ (US)

(72) Inventors: Hao Bai, Beijing (CN); Henry Chen, Beijing (CN); Paul Derby, Lubbock, TX (US); Hari Thiruvengada, Plymouth, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/906,836

(22) PCT Filed: Mar. 12, 2014

(86) PCT No.: PCT/US2014/024200
§ 371 (c)(1),
(2) Date: Jan. 21, 2016

(87) PCT Pub. No.: WO2014/150776
PCT Pub. Date: Sep. 25, 2014

(65) Prior Publication Data
US 2016/0180587 A1    Jun. 23, 2016

Related U.S. Application Data

(63) Continuation of application No. 13/839,056, filed on Mar. 15, 2013, now Pat. No. 9,361,411, which is a
(Continued)

(51) Int. Cl.
*G06T 17/20* (2006.01)
*G06T 19/00* (2011.01)
(Continued)

(52) U.S. Cl.
CPC ............. *G06T 17/20* (2013.01); *A62B 7/02* (2013.01); *A62B 7/04* (2013.01); *G06F 17/50* (2013.01);
(Continued)

(58) Field of Classification Search
None
See application file for complete search history.

(56) References Cited

U.S. PATENT DOCUMENTS 8,194,097 B2 *   6/2012   Xiao .................. G06K 9/00261
                                                                     345/419
9,361,411 B2 *   6/2016   Thiruvengada ..... G06F 17/5009
(Continued)

*Primary Examiner* — James A Thompson
(74) *Attorney, Agent, or Firm* — Craige Thompson; Thompson Patent Law

(57) ABSTRACT

Apparatus and associated methods relate to determining a fit-quality metric for a mask/face combination based upon a calculated dead-space volume between a virtual mask and a virtual face virtually aligned so as to create an integrity seal circumscribing a mouth and nose region. In an illustrative embodiment, an interactive virtual fitting system may receive a three-dimensional (3D) virtual face associated with a person. The system may retrieve 3D models of various respirators selected by user determined criteria. The system may then compute a fit-quality metric for each of the retrieved 3D models. The potential wearer may then be presented with the metrics for review. The potential wearer may select a respirator based upon these computed metrics. A virtual fitting of many respirators may advantageously reduce the time needed for selecting a properly fitting respirator while simultaneously ensuring that the selected respirator may be comfortable and well fitting.

20 Claims, 38 Drawing Sheets

Related U.S. Application Data continuation of application No. 13/839,186, filed on Mar. 15, 2013, now abandoned.

(60) Provisional application No. 61/917,171, filed on Dec. 17, 2013, provisional application No. 61/861,294, filed on Aug. 1, 2013, provisional application No. 61/814,897, filed on Apr. 23, 2013, provisional application No. 61/814,905, filed on Apr. 23, 2013.

(51) Int. Cl.
| | |
|---|---|
| *G06T 19/20* | (2011.01) |
| *G06F 17/50* | (2006.01) |
| *A62B 7/02* | (2006.01) |
| *A62B 7/04* | (2006.01) |
| *G06K 9/00* | (2006.01) |
| *G06F 19/12* | (2011.01) |
| *G06F 19/24* | (2011.01) |
| *A62B 27/00* | (2006.01) |
| *A62B 99/00* | (2009.01) |

(52) U.S. Cl.
CPC ..... *G06F 17/5009* (2013.01); *G06K 9/00281* (2013.01); *G06T 19/006* (2013.01); *G06T 19/20* (2013.01); *A62B 27/00* (2013.01); *A62B 99/00* (2013.01); *G06F 19/12* (2013.01); *G06F 19/24* (2013.01); *G06T 2200/04* (2013.01); *G06T 2200/08* (2013.01); *G06T 2200/24* (2013.01); *G06T 2219/2004* (2013.01); *G06T 2219/2021* (2013.01)

(56) References Cited

U.S. PATENT DOCUMENTS

| | | | |
|---|---|---|---|
| 2006/0023228 A1* | 2/2006 | Geng | A61B 5/411 356/601 |
| 2006/0048777 A1* | 3/2006 | Brookman | A62B 7/02 128/201.22 |
| 2008/0006273 A1* | 1/2008 | Thornton | A61M 16/06 128/206.21 |
| 2008/0111814 A1* | 5/2008 | Sengamedu | G06T 7/0051 345/419 |
| 2008/0117215 A1* | 5/2008 | Hery | G06T 13/00 345/473 |
| 2009/0132371 A1* | 5/2009 | Strietzel | G06Q 30/0247 705/14.46 |
| 2009/0292614 A1* | 11/2009 | Reichow | G03B 21/10 705/14.72 |
| 2011/0298897 A1* | 12/2011 | Sareen | G06N 3/006 348/47 |
| 2014/0278319 A1* | 9/2014 | Thiruvengada | G06F 17/5009 703/11 |
| 2014/0278320 A1* | 9/2014 | Wang | G06F 17/5009 703/11 |
| 2015/0157822 A1* | 6/2015 | Karpas | B29C 33/52 128/206.24 |
| 2015/0235372 A1* | 8/2015 | Smolyanskiy | G06T 7/0071 345/420 |
| 2016/0162604 A1* | 6/2016 | Xiaoli | G06F 17/5009 703/1 |
| 2016/0196665 A1* | 7/2016 | Abreu | G06T 11/00 345/427 |
| 2016/0361511 A9* | 12/2016 | Karpas | A61M 16/0605 |

* cited by examiner

VIRTUAL MASK FITTING SYSTEM

CROSS-REFERENCE TO RELATED APPLICATIONS

This application fully incorporates the disclosures of the following previously submitted applications by reference herein:

| | | |
|---|---|---|
| 13/839,056 | System and Method for Selecting a Respirator | Mar. 15, 2013 |
| 13/839,186 | System and Method for Selecting a Respirator | Mar. 15, 2013 |
| 61/814,897 | System and Method for Selecting PPE | Apr. 23, 2013 |
| 61/814,905 | System and Method for Evaluating PPE Fit | Apr. 23, 2013 |
| 61/861,294 | Virtual Mask Fitting System | Aug. 1, 2013 |
| 61/917,171 | Virtual Mask Alignment for Fit Analysis | Dec. 17, 2013 |

TECHNICAL FIELD

Various embodiments relate generally to personal protection equipment, and more specifically to the fitting of such equipment to the human body.

BACKGROUND

Personal protective equipment (PPE), such as for example respirators, are widely used in a variety of different applications. For example, many workplaces that subject an employee to hazardous atmospheric conditions require the employee to wear respiratory protection for several hours per day. To be effective, respiratory protection requires a proper seal upon a facial area of the user. A poor seal and thus poor fit may result in leakage and the possibility of the inhalation of contaminants.

Finding a respirator that fits a unique facial area of the user can require the user to try on many different types and sizes of respirators. In some workplace environments, valuable time can be spent attempting to find an optimal fitting respirator. In other workplace environments, an employee may not be able to find a respirator having a suitable fit. For example, the employee may not be given adequate time to try on different respirators or the employee may not be given an adequate variety of respirator samples to try.

SUMMARY

Apparatus and associated methods relate to determining a fit-quality metric for a mask/face combination based upon a calculated dead-space volume between a virtual mask and a virtual face virtually aligned so as to create an integrity seal circumscribing a mouth and nose region. In an illustrative embodiment, an interactive virtual fitting system may receive a three-dimensional (3D) virtual face associated with a person. The system may retrieve 3D models of various respirators selected by user determined criteria. The system may then compute a fit-quality metric for each of the retrieved 3D models. The potential wearer may then be presented with the metrics for review. The potential wearer may select a respirator based upon these computed metrics. A virtual fitting of many respirators may advantageously reduce the time needed for selecting a properly fitting respirator while simultaneously ensuring that the selected respirator may be comfortable and well fitting.

Various embodiments may achieve one or more advantages. For example, some embodiments may reduce the time needed for a person to be fit to a PPE device. In some embodiments, the person to be fit may need not be present at the location where the virtual fitting is computed. The person to be fit, may need not be present at a storage facility for PPE devices. Sample fitting devices need not be purchased. The elimination of sample fitting devices may preclude the need for cleaning such devices between fittings. Inventories of PPE devices may be reduced by the elimination of sample fitting devices.

Potential wearer's of PPE devices may have more devices virtually fit than they would physically try on. This increased fitting count may translate into improved matching of PPE device to a wearer. Wearer's may find more comfort in their selected PPE devices. And PPE devices may properly fit a wearer. This proper fit may translate into improved protection against harm.

Apparatus and associated methods may relate to fitting a virtual mask to a virtual face by first fitting a chin region of the virtual mask to the virtual face, then determining a virtual mask angle that maintains the fitted chin region while simultaneously fitting a nose-bridge region of the virtual mask to the virtual face, and then calculating a fit-quality metric corresponding to the fitted position. In an illustrative embodiment, the fitted chin region may include the high curvature menton region of the chin. In some examples, a virtual mask may be virtually pressed toward the virtual face using a predetermined force corresponding to a force of a mask securing device of a real mask corresponding to the virtual mask In an exemplary embodiment, the fitting of a virtual mask to a virtual face may advantageously yield a mask's fit quality in a brief amount of time.

When an activity requires a person to wear a mask to protect the person from a known hazard, one or more fit tests may be performed to ensure that the mask seals properly to a person's face. Fit tests may be time consuming, as the person first may need to select a mask for testing, and then don the selected mask. After donning the selected mask, the person may subject him/herself to a qualitative test. The person may then stand in a testing chamber in which the ambient is exposed to chemicals that the user can detect by smell or taste, for example. If the user detects the chemical introduced into the ambient, the mask seal may be determined to be inadequate. Such a qualitative test may take tens of minutes to complete. And the results of the test are not precise as to the quality of the fit. For example, one may not be able to determine if the mask fit has a small seal leak or a large seal leak.

Sometimes the person may then undergo a quantitative test. In this test, the mask wearing person may have a machine connected to a mask portal via a tube. The machine may then monitor the quality of the exhalations from the mask portal. Measurable chemicals may be introduced into the testing chamber. If the chemicals are detected in the exhalation chemistry, the machine may measure the concentration of the detected chemical. The machine may then determine a magnitude of the mask seal leak. This test may take additional tens of minutes to perform. After performing the above described tests, the person often may have to repeat the testing process wearing another mask selected for testing. Such repetitions can be very time consuming and/or expensive.

Various embodiments may achieve one or more advantages. For example, some embodiments may facilitate the virtual fitting of many masks to a user in a brief amount of time. In some embodiments, the time and cost of performing qualitative and quantitative testing of masks that are unlikely to fit well may be eliminated. In some embodiments, an ability to suggest a mask having a good likelihood to provide a proper seal may result in more comfortable mask assignments. Such comfort may translate into improved worker productivity and/or increased mask use. In some embodiments, a database of users' 3D virtual faces may be used to direct inventory decisions. In an exemplary embodiment, the database of 3D virtual faces may direct future mask development activities. Safety masks having improved fit for a variety of faces may result from using such a database.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

To aid understanding, this document is organized as follows. First, an exemplary method of virtually aligning a virtual mask to a virtual face will be described with reference to FIGS. 1-13. Then, with reference to FIGS. 14-22, an exemplary virtual mask-fitting system that implements some of the virtual alignment techniques described in FIGS. 1-13. The discussion of alignment techniques begins with a description of an exemplary virtual alignment system, with reference to FIGS. 1 and 10. Then an exemplary chin region alignment technique will be described with reference to FIGS. 2-6C and 11. This will be followed by a description of an exemplary nose-bridge fitting technique, with reference to FIGS. 7-8 and 12. An exemplary virtual mask-tightening procedure will be described with reference to FIGS. 9 and 13. The discussion of a virtual mask-fitting system begins, with reference to FIGS. 14-21, by describing an exemplary PPE selection by a user using a virtual fitting station. Then, with reference to FIG. 22, a description of exemplary system components for a virtual fitting station will be detailed. Then, with reference to FIG. 23, an exemplary method of PPE selection using a virtual fitting station will be described.

Figure 1:
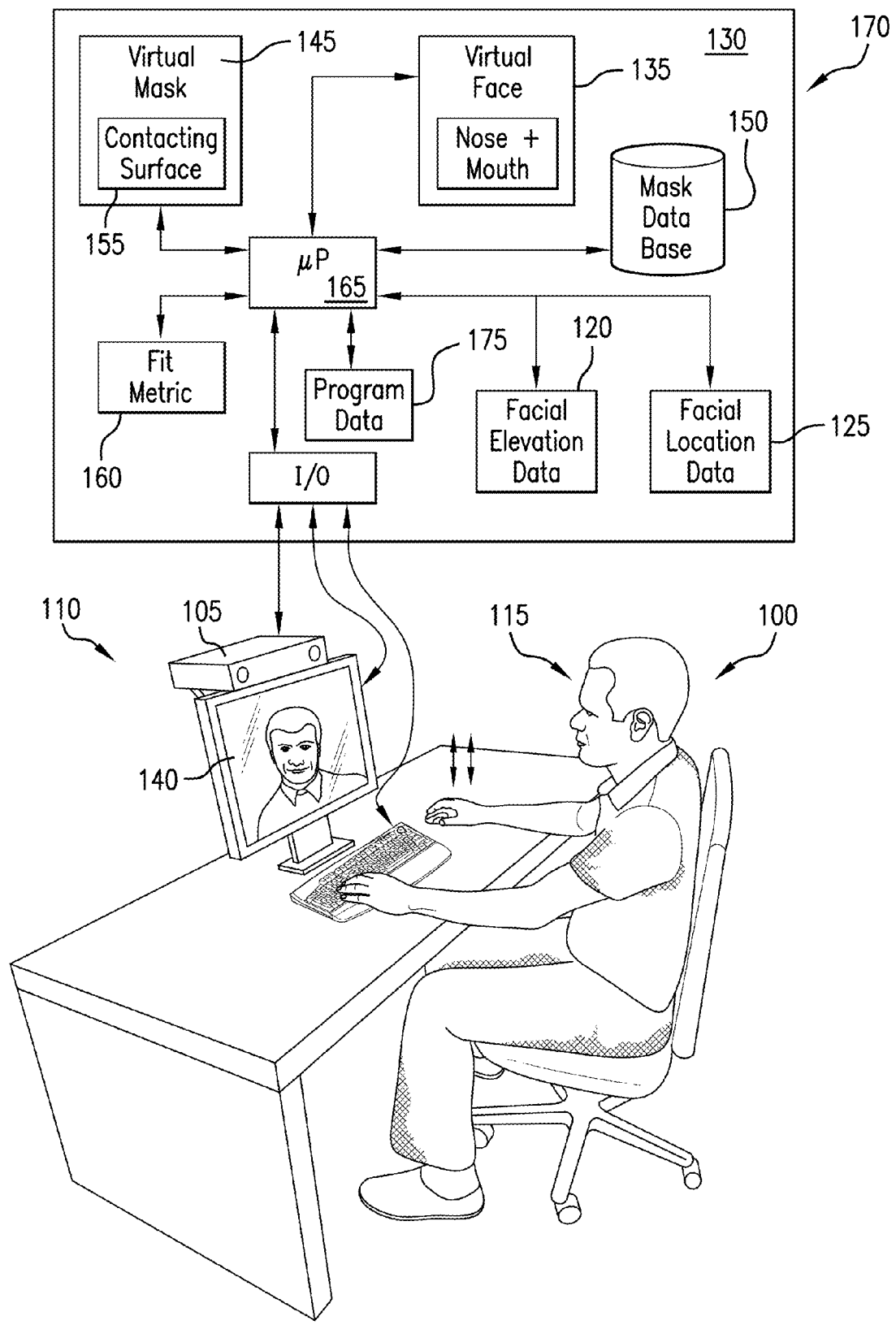
FIG. 1 depicts an exemplary PPE virtual fitting station.

FIG. 1 depicts an exemplary PPE virtual fitting station. In the FIG. 1 depiction, a user 100 is seated at a virtual fitting station 110. The virtual fitting station includes a 3D facial scanner 105, a display device 140 and a mask fitting engine 170. The mask fitting engine 170 is depicted having a processor 165 which may execute instructions received from program memory locations 175. The received program instructions may cause the processor 165 to perform operations related to obtaining data representative of a 3D facial model representative of a user's face, aligning the facial model to a 3D mask model, and calculating a fit-quality metric characterizing a quality of the mask model fit to the facial model. Such processor operations and/or other operations be repeated on other 3D mask models representative of different models and/or makes of masks. Such processor operations and/or other operations may be repeated on other facial models representative of other users' faces. These operations may advantageously return fit-quality metrics for one or more user/mask combinations in a short time. These fit-quality metrics may select real mask models, which may be tested further for fit integrity. Such further fit integrity testing may be avoided for user/mask combinations associated with a poor virtual fit-quality metric.

In the FIG. 1 depiction, a user 100 is operating a 3D facial scanner 105 at a virtual fitting station 110. The 3D facial scanner 105 has scanned a user's face 115 creating facial elevation data 120 and corresponding facial position data 125. A virtual fitting engine 130 may create a virtual face 135 based upon the scanned facial elevation data 120 and the corresponding facial position data 125. The virtual fitting engine 130 may send image data corresponding to the virtual face 135 to a display device 140. The virtual fitting engine 130 may retrieve a virtual mask 145 from a mask database 150. The virtual mask 145 may include a virtual facial-contacting surface 155 configured to contact a virtual face 135 circumscribing a nose and mouth region of a virtual face 135. The virtual fitting engine 130 may virtually align the virtual mask 145 to the virtual face 135 near a high curvature location of a chin region. The virtual fitting engine 130 may virtually rotate the virtual mask 145 about a chin region rotation point to bring a nose-bride region of the virtual mask 145 into virtual proximity with a nose-bridge region of the virtual face 135. In some embodiments, the virtual mask 145 may be virtually pressed against the virtual face 135 to simulate a force of a real mask attachment device when securing a real mask to a real face. The virtual fitting engine 130 may then calculate a fit-quality metric 160 based upon a relationship of the virtual facial-contacting surface 150 to adjacent facial elevation data 120 when the virtual mask 145 has been aligned as described above. In some embodiments, the fit-quality metric 160 may be calculated by evaluating the proximity of a virtual facial-contacting surface 155 along a path circumscribing the nose and mouth region of the virtual face 135. The calculated fit-metric 160 may be associated with a mask-user combination. The virtual fitting engine 130 may send a signal representative of the fit-quality metric 160 for display to the display device 140. After an initial scan of the user's face 115, many different virtual masks may be virtually fit to the virtual face 135 associated with the user 100 perhaps without need of the users continued participation. In this way, one or more well-fitting masks may be optimally selected from the mask database 150 for trial by the user 100.

Figure 2:
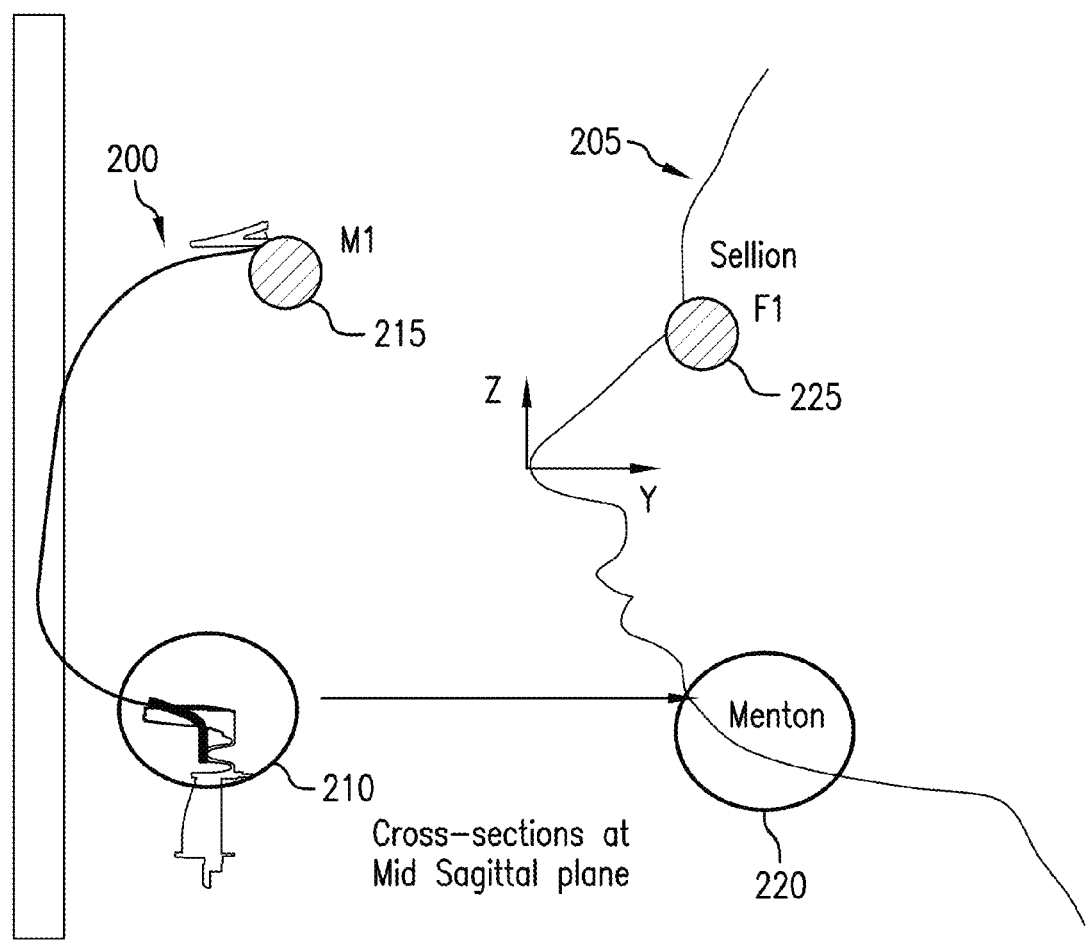
FIG. 2 depicts an exemplary mask face alignment along the mid-sagittal plane cross-section.

FIG. 2 depicts an exemplary mask/face alignment along a mid-sagittal plane cross-section. In the FIG. 2 depiction, an exemplary virtual mask 200 and an exemplary virtual face 205 are shown in cross-section along a mid-sagittal plane (the plane of the drawing sheet). A menton region 210 and a sellion region 215 of the virtual mask are identified. The virtual face 205 also has a menton region 220 and a sellion region 225. A coordinate system depicted in the figure aligns a Y-axis 220 in the vertical direction and a Z-axis 225 in the horizontal direction within the mid-sagittal plane. An X-axis (not depicted) may extend perpendicular to the drawing sheet. The virtual mask 200 may be fit to the virtual face 205 first at the menton region 210. The menton region 220 of the virtual face 205 may have high curvature in the Y-Z plane at a forward chin location. The virtual mask 200 may have a complementary high-curvature in the menton region 210 for receiving the high-curvature of the forward chin location. This high-curvature region may provide an initial fitting relationship between the virtual mask 200 and the virtual face 205. Then the virtual mask 200 may then be rotated about the fitted menton region 210 to optimally fit the sellion region 215 of the virtual mask 200 to the sellion region 225 of the virtual face 205. In some embodiments, the sellion region 215 may first be fit and then the mask rotated to fit the menton region 210. By fitting the mask along the mid-sagittal plane, a small fraction of the virtual contact points of the mask/face interface may be considered. This, in turn may result in an initial mask/face alignment being quickly determined.

Figure 3:
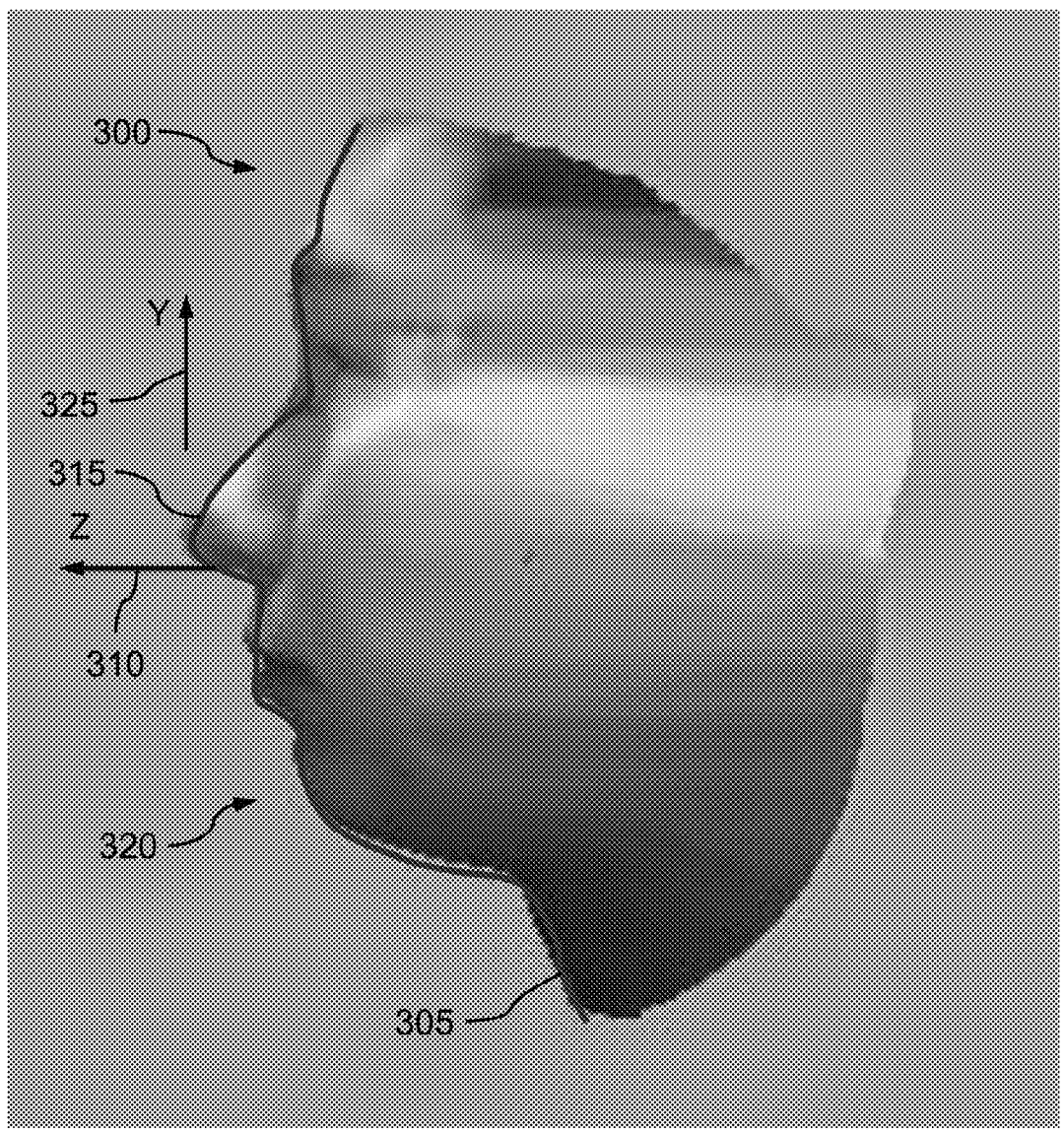
FIG. 3 depicts a side view of a 3D captured human face and the determination of facial profile along the mid-sagittal plane.

FIG. 3 depicts a side view of a 3D captured human face and the determination of facial profile along the mid-sagittal plane. In the FIG. 3 depiction, a captured 3D human face 300 is displayed from a side perspective so that a mid-sagittal plane profile 305 may be clearly depicted. The mid-sagittal plane has a Z-axis 310 and a Y-axis 325. In some embodiments, the maximal projection in the Z-direction 310 of the image may be used to identify a nose tip 315 of the captured 3D human face 300. A location of a menton region 320 may then be obtained using the relative Y and Z positions of the chin from the nose tip 315. In some embodiments, the curvature of the mid-sagittal plane profile 305 may be used to determine the location of the menton region 320. Locating the menton region 320 from the captured 3D human face 300 may provide an initial location for fitting a virtual mask, for example. In some embodiment, the mid-sagittal plane may be determined by finding a line of facial symmetry, for example. The determined mid-sagittal plane may be used to center a virtual mask upon a virtual face. After centering a virtual mask upon a virtual face, a vertical (Y-axis) location may be obtained for aligning a virtual mask to a virtual face. Where a face has little curvature along this vertical dimension, the face may present few locating features. But where the face has large curvature along the vertical dimension, locating features may be presented. If a virtual mask is designed to engage such a large curvature locating feature (e.g. chin or nose), for example, locating these features may assist in finding a good initial position for mask alignment.

Figure 4:
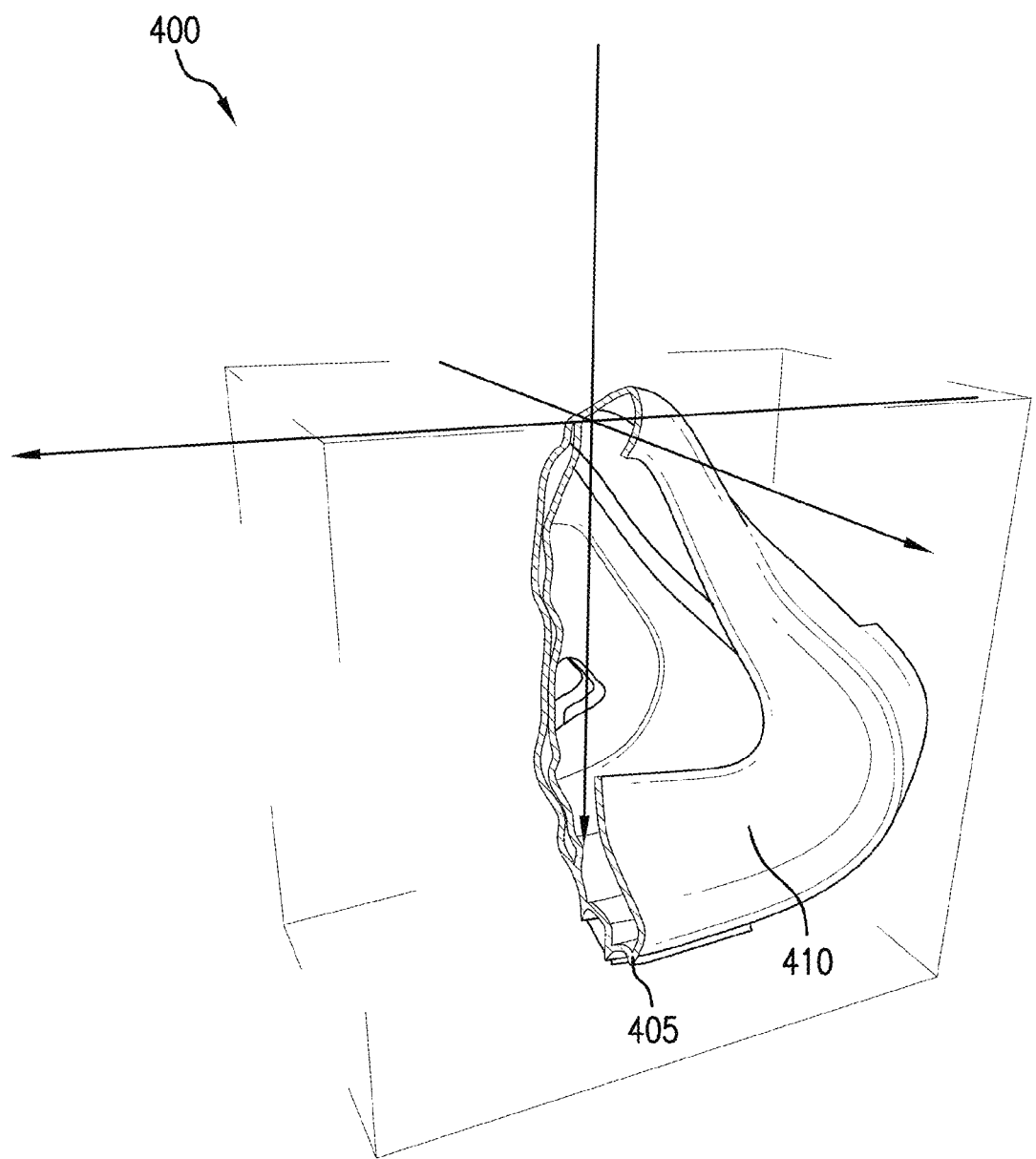
FIG. 4 depicts an exemplary breathing mask cross-sectioned along the mid-sagittal plane.

FIG. 4 depicts an exemplary breathing mask cross-sectioned along the mid-sagittal plane. In the FIG. 4 depiction, an exemplary virtual mask 400 is shown from a rear perspective view. The exemplary virtual mask 400 has been cross-sectioned along the mid-sagittal plane so that a mid-sagittal elevation profile 405 may be seen. A facial-contacting surface 410 of the depicted virtual mask 400 is shown. A real contacting surface of a corresponding real mask may be made of a soft and/or deformable material. Such a deformable material may facilitate conformity of the mask to a user's face when the mask is pressed into the face by a mask securing device. Such conformity with the user's face may provide an integrity seal of the mask to the face around a mouth/nose perimeter path. A facial contacting region of the mid-sagittal elevation profile 405 may be used for an initial locating of the virtual mask to the virtual face, for example. In some embodiments, the menton region of the facial contacting surface 410 may be used to initially locate the virtual mask to the virtual face. The facial contacting surface 410 may present a curvature region that is substantially complementary to a facial curvature feature. Masks may be designed to engage a facial feature having a large curvature. Some masks may have malleable engagement surfaces that may deform when pressed into a user's face. A virtual mask 400 may include indicia of malleability. These indicia of malleability may vary with position. For example. The malleability of a facial-engagement surface 410 may be a function of location along the facial-engagement surface 410. This malleability function may be used in determining a pressed position of a mask against a user's face, for example. Pressing a mask against a wearer's face may minimize or eliminate air gaps in the perimeter of the engagement-surface/user's-face interface.

Figure 5:
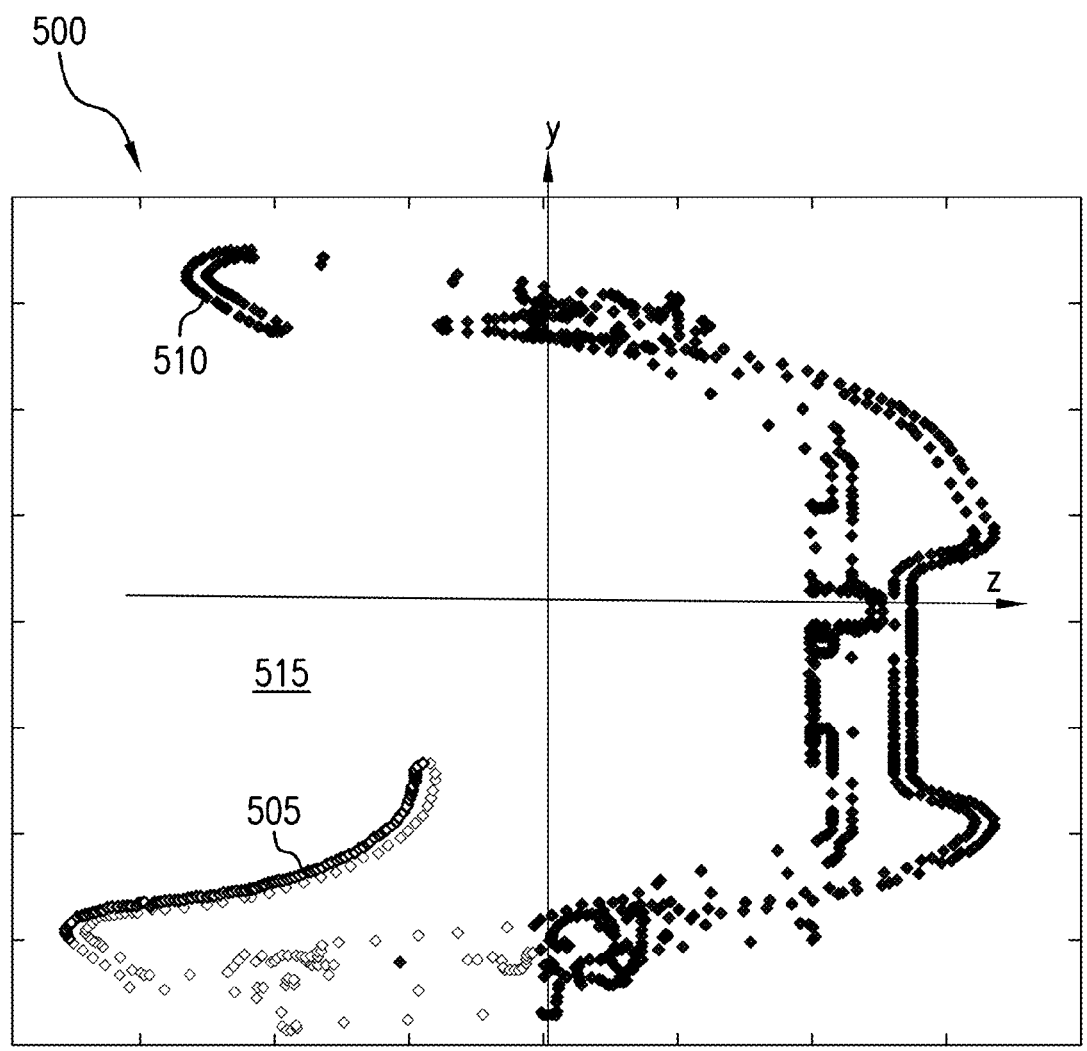
FIG. 5 depicts the surfaces of an exemplary breathing mask along the mid-sagittal plane of the mask.

FIG. 5 depicts the surfaces of an exemplary breathing mask along the mid-sagittal plane of the mask. In the FIG. 5 depiction, the virtual mask data 500 plotted in a Y-Z coordinate system. The virtual mask data 500 is the mid-sagittal profile of a virtual mask. The origin of the Y-Z coordinate system centers the mid-sagittal profile data 500 in the coordinate system. The mid-sagittal profile 500 includes a menton contacting surface 505 and a nose-bridge contacting surface 510. The menton contacting surface 505 is depicted with a curvature in the Y-Z plane. The menton contacting surface may be obtained by first extracting points in the third quadrant 515 of the depicted coordinate system, for example. The mid-sagittal profile data 500 in the third quadrant 505 may include both a menton contacting surface 505 and non-contacting surfaces 520. This menton contacting surface 505 may be extracted by selecting a subset of the third quadrant data having the most negative Z-coordinates, for example. Then those data that are monotically increasing as their Y-coordinates increase (concave-up curvature) may be selected from this most negative Z-coordinate subset. This selected data may be used to fit the virtual mask to a virtual face at a menton region, for example. In some embodiments, the virtual mask may identify the menton contacting surface 505 as part of the model. In some exemplary embodiments, the selection of the menton contacting surface may need to be performed only once when a virtual mask model is being created. The selection of the nose-bridge contacting surface may be found in similar manners.

Figure 6A:
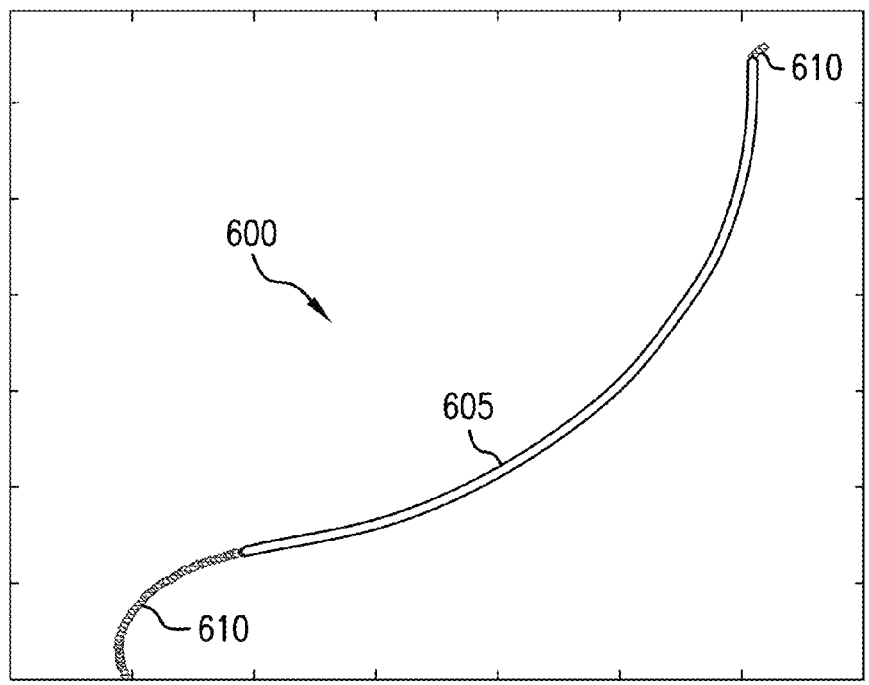
FIGS. 6A-6C depict the facial contacting menton region of an exemplary breathing mask and the corresponding menton region of a virtual face along the mid-sagittal plane.
Figures 6B, 6C:
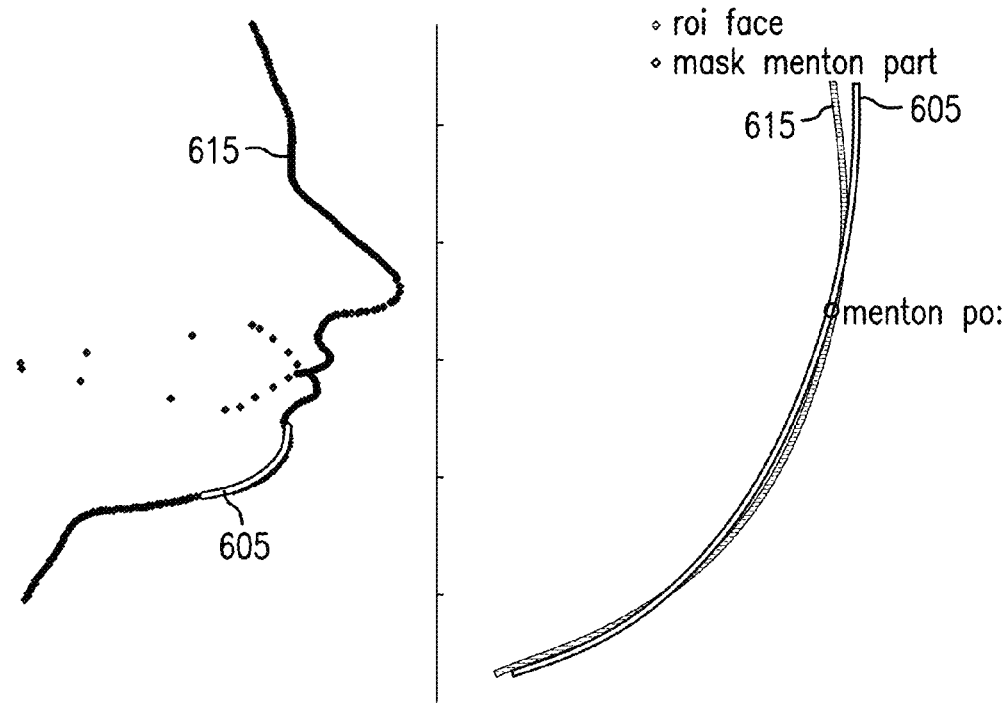

FIGS. 6A-6C depict the facial contacting menton region of an exemplary breathing mask and the corresponding menton region of a virtual face along the mid-sagittal plane. In FIG. 6A, third quadrant menton region data 600 is displayed. The third quadrant menton region data 600 includes a facial contacting surface 605 and non-contacting surfaces 610. In FIG. 6B, the facial contacting surface 605 has been aligned to a mid-sagittal facial profile 615 of a person. In some embodiments, a least-squared fitting method may be used to determine the optimal fit location of the facial contacting surface 605 to the mid-sagittal facial profile 615. In some embodiments a sliding window analysis may be used to determine an optimal fit location. In an illustrative embodiment, interpolation between adjacent data points may be used to increase the density of the data points to be fit. In some embodiments, interpolation may be used to provide a common coordinate system for data comparison and/or fit. In an illustrative embodiment, the optimal fit may be determined by aligning the points of maximum curvature of the virtual mask to that of the virtual face, for example. In an exemplary embodiment, elasticity values may be assigned to each data point of the menton region data facial contacting surface 605. The elasticity values may be a function of the location of each data point, for example. In some embodiments, the elasticity values may be used in determining the optimal fit location. For example, a weighting factor corresponding to the elasticity may be assigned to each data point. A highly elastic data point may be assigned a low weighting value. This may permit the data point to fit more poorly to the face than a data point with a high weighting value corresponding to a low elasticity. FIG. 6C depicts a close-up view of the facial contacting surface 600 positioned in the optimal fit location with respect to the mid-sagittal facial profile 615 of the person.

Figure 7:
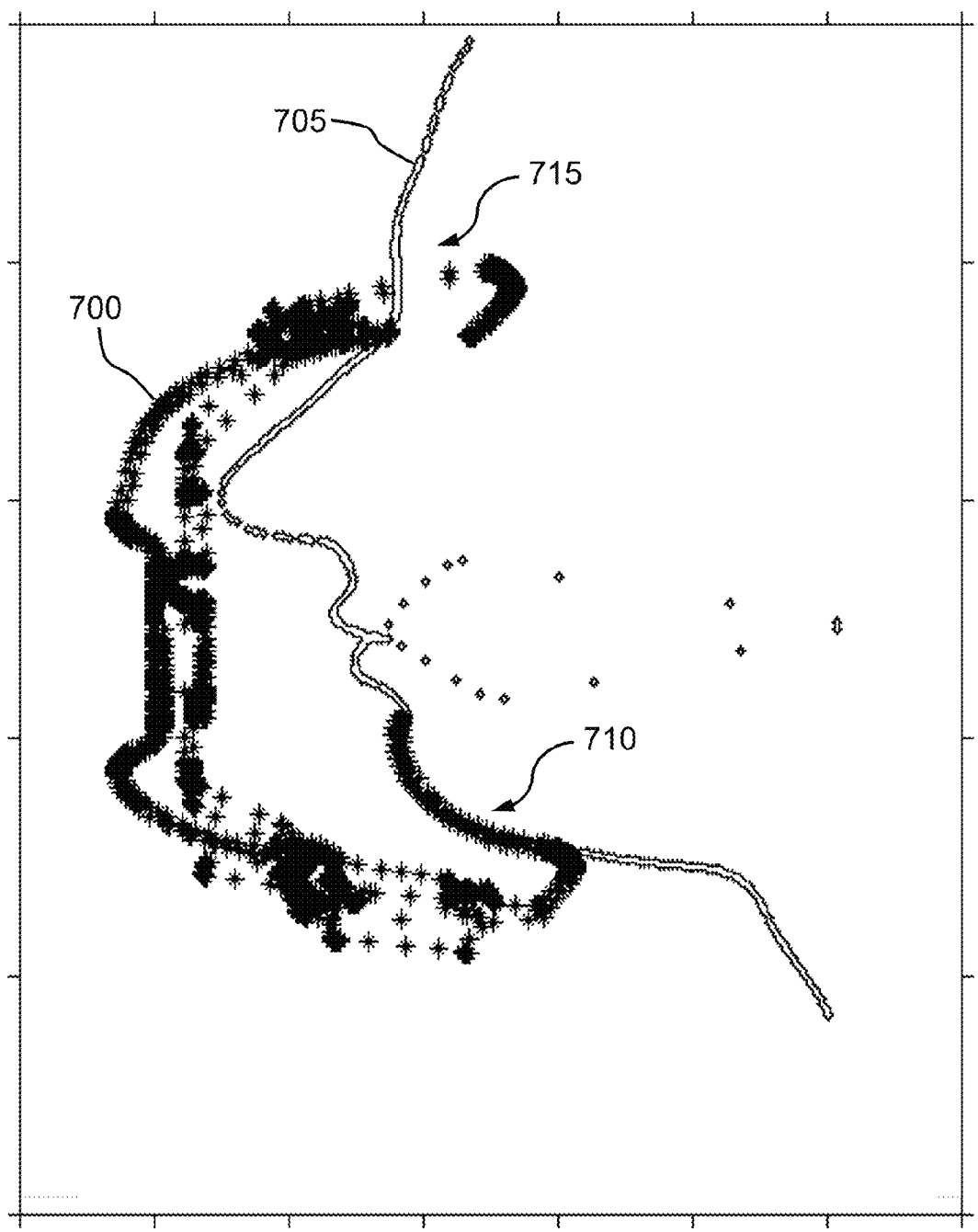
FIG. 7 depicts the juxtaposition of a virtual mask on a virtual face, aligned to the best fit of the menton region.

FIG. 7 depicts the juxtaposition of a virtual mask on a virtual face, aligned to the best fit of the menton region. In FIG. 7 a virtual mask 700 has been translated to a virtual face 705. The translation may have aligned a previously determined optimal fit position of the menton region 710 of the virtual mask 700 to that of virtual face 705. In the depicted alignment, a sellion region 715 of the virtual mask 700 may be poorly aligned relative to a sellion region 715 of the virtual face 705. The virtual mask 705 may be rotated such that the sellion region 715 of the virtual mask 700 is pressed into the virtual face 705. Such a rotational position would likely be uncomfortable or even impossible, even with consideration of a mask's elasticity. Thus the virtual mask 700 may need rotation away from the sellion region 715 of the virtual face 705 to obtain a better quality fit. In some embodiments the virtual face 705 may be rotated to accommodate any rotational mismatch between a virtual mask 700 and a virtual face 705.

Figure 8:
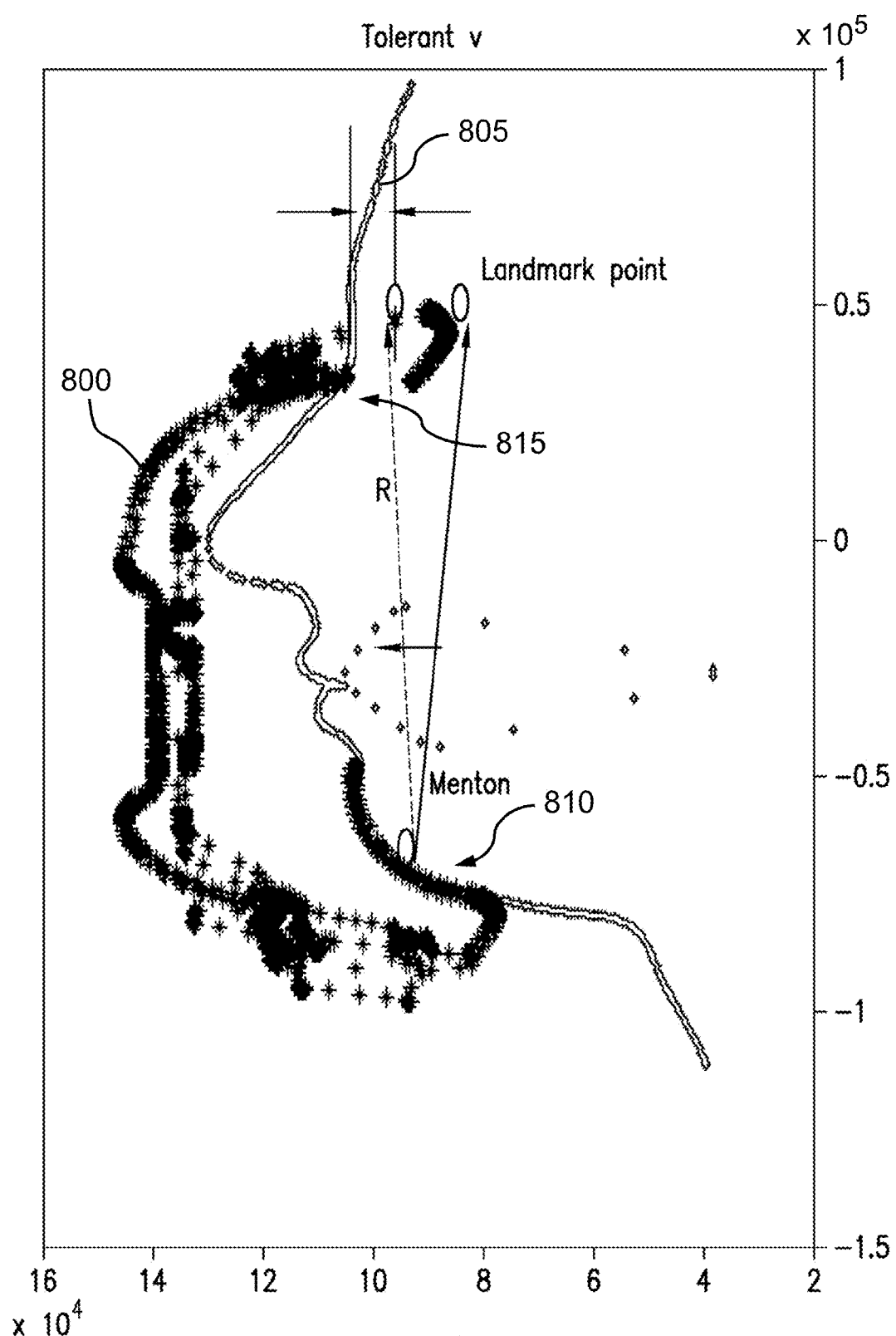
FIG. 8 depicts a schematic of a virtual mask being rotated into an optimal fit position on a user's virtual face.

FIG. 8 depicts a schematic of a virtual mask being rotated into an optimal fit position on a user's virtual face. In the FIG. 8 depiction, a user's virtual face 800 has a virtual mask 805 superimposed onto it at an initial alignment position. A chin region 810 has been fit, but a nose-bridge region 815 requires fit modification. The angle between the virtual mask 805 and the virtual face 800 may require modification. A determination of an optimal angle may include a determination of an optimal nose-bridge mask/face alignment, for example. A point of rotation may be selected near the chin region 810, for example. The point of rotation may be selected at the central point of a menton contacting surface, for example. In some embodiments, a point near a forward chin-bone location of the virtual face 800 may be selected as the point of rotation. In some embodiments, a least squares rotation operation may be performed. In an exemplary embodiment the optimum rotation may be performed using weighted data corresponding to elasticities of the mask at various locations along a facial-contacting surface. In some embodiments, a fit metric corresponding to each data point may be based upon the difference in a Z-direction between the virtual mask 800 and the virtual face 805. In some embodiments, a fit metric corresponding to each data point may be based upon the distance between the virtual mask 800 and the virtual face 805 normal to a surface of the virtual mask 800 and/or the virtual face 805.

Figure 9:
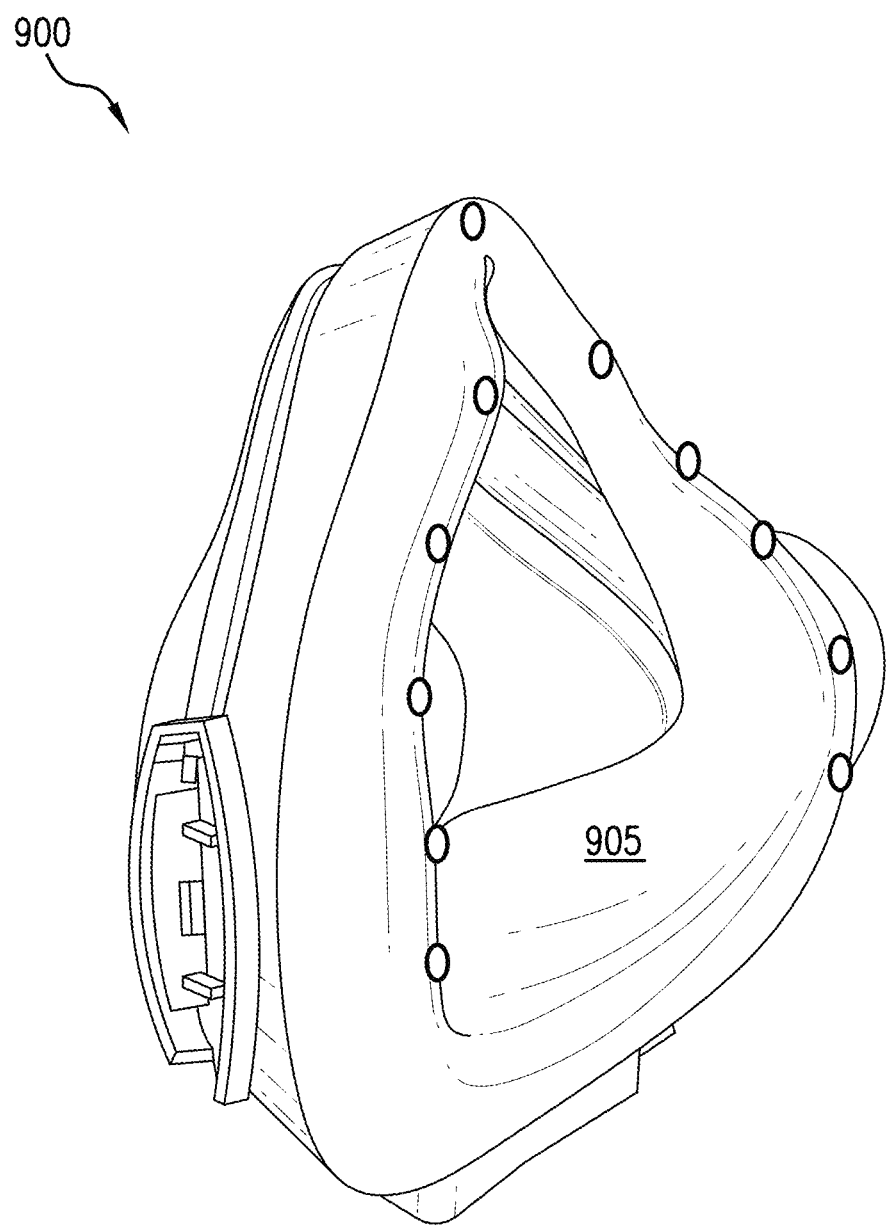
FIG. 9 depicts an exemplary breathing mask with exemplary landmark points identified around a sealing periphery.

FIG. 9 depicts an exemplary breathing mask with exemplary landmark points identified around a sealing periphery. In the FIG. 9 embodiment, an exemplary virtual mask 900 has a contacting surface 905 configured to peripherally seal the virtual mask 900 to a virtual face around a nose and mouth region. After fitting a virtual mask 900 to a virtual face, some embodiments press the virtual mask 900 into the virtual face. This pressing operation may simulate a real force imparted by a real mask onto a real face by a real mask securing device. In some embodiments, an elastic band may serve as a mask securing device. In some embodiments a tightening strap may serve as a mask securing device. A real mask securing device may force a mask into a face to provide an integrity seal between the mask and the face of a wearer. In an exemplary embodiment, a functional relationship may be defined between a deformability parameter and a location of the contacting surface 905. For example, each location of the contacting surface may have a corresponding deformability value. The virtual mask 900 may be translated in the direction of a virtual face in response to a virtual force. The translation may proceed until the virtual force required for such a translation exceeds a predetermined threshold, for example. In some embodiments, the virtual force may be calculated by integrating the force required for deformation around the periphery of the contacting surface 905 of the virtual mask 900. For example, the initial position of the mask may contact the user at three distinct points before the translation begins. The mask may be incrementally translated in the facial direction. After each translation, an integrated force may be calculated around the sealing periphery. The translation may be terminated when the calculated force exceeds a predetermined threshold. In some embodiments the translation may be terminated when a maximum force at any discrete location exceeds a predetermined threshold. In some embodiments, the mask may be further rotated after a force has been calculated. For example, an integrated force on an upper region of the mask may be much greater than an integrated force on a lower region of the mask. To balance the upper and the lower force, the mask may be rotated, for example. Further translation may again be resumed after the mask forces have been equilibrated, for example.

In some embodiments, an integration may be approximated by a summation of discrete landmark points around a mask periphery. Many landmark points may be evaluated, in some embodiments. For example, landmark points may be selected around a sealing surface that may circumferentially seal around a user's mouth and nose. Each landmark point may be assigned a toleration value, a component of which may represent a flexion value of the mask at that landmark point location, and a component of which may represent a reasonable tolerance of tissue deformation at a facial position associated with the landmark point location. Various numerical means of determining an optimal rotation may be used. For example, such techniques as least-squared fit methods may be used in determining the optimal rotation of the virtual mask. In some examples, weighted regression techniques may be used to determine the optimal rotation.

Figure 10:
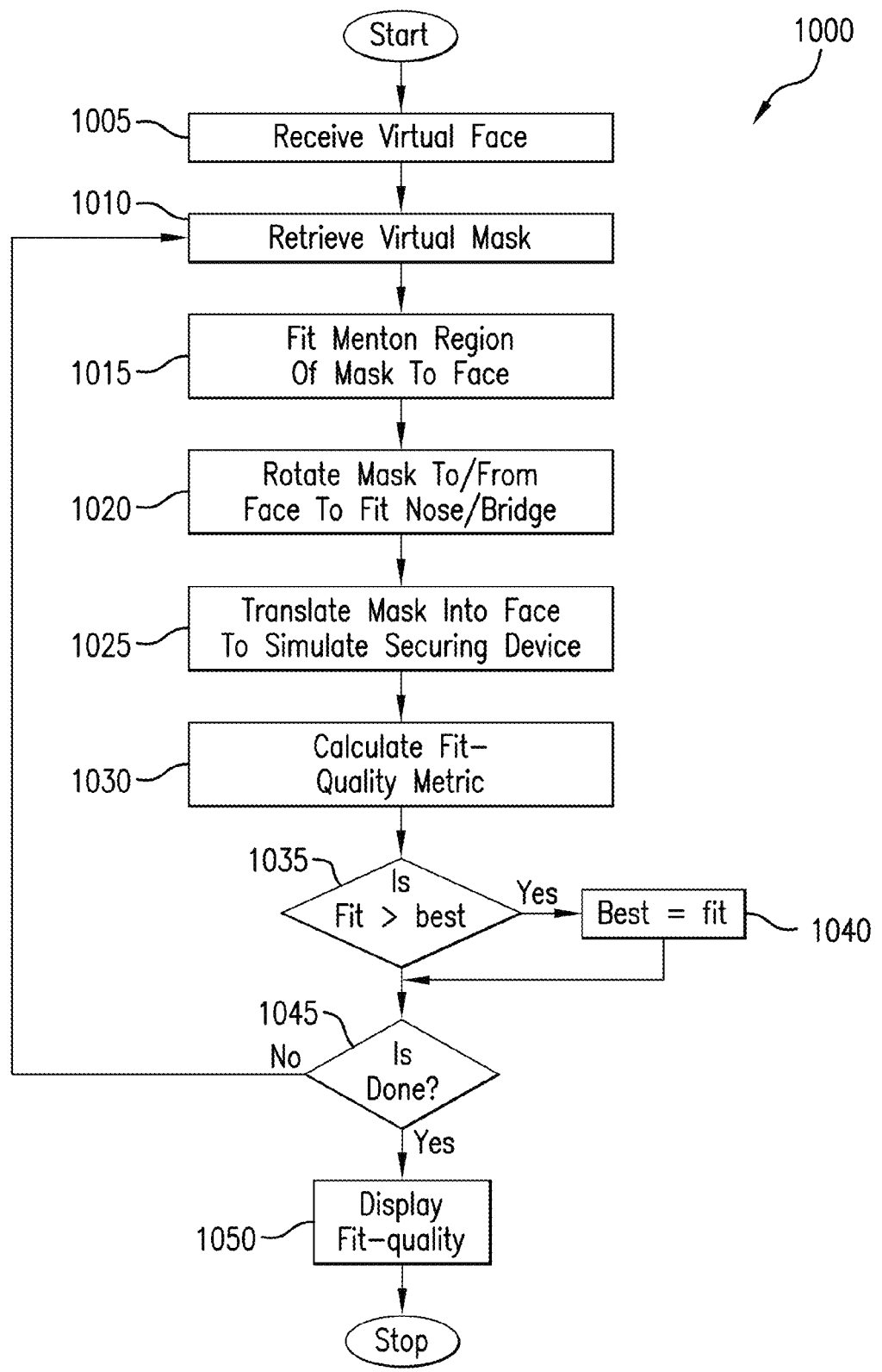
FIG. 10 depicts an exemplary method for predicting the fit of a virtual mask to a virtual face.

FIG. 10 depicts an exemplary method for predicting the fit of a virtual mask to a virtual face. In FIG. 10 an exemplary virtual fitting method 1000 is described from a vantage point of the processor 165 depicted in FIG. 1. The virtual fitting method 1000 begins with the processor 165 receiving a 3D virtual face of a person 1005. The 3D virtual face may be obtained by a 3D scanner 105, for example, and then communicated to the processor 165. In some embodiments, the 3D virtual face may have been previously obtained and retrieved by the processor 165 from a storage device. The processor 165 then retrieves a virtual mask from a database of virtual masks 1010. Then the processor 165 determines an optimal chin alignment between the virtual mask and the virtual face 1015. The processor 165 then determines an optimal nose-bridge fit by rotating the virtual mask toward or away from the virtual face about the optimal chin location 1020. The processor 165 then translates the virtual mask, as aligned at the chin and rotated to the nose-bridge, into the virtual face 1025. This translation may simulate the translation of a real mask into a real face in response to an applied force. In some embodiments, a mask securing device may produce the force that secures a mask to a face, for example. The processor 165 may then calculate a fit-quality metric and associate the fit-quality metric with the virtual face-mask combination 1030. The processor 165 may test whether this fit-quality metric is the best one associated with the virtual face 1035. If the fit-quality metric is better than the previous best fit-quality metric associated with the virtual face, the fit-quality metric is assigned as the best fit-quality metric 1040. If, however, the fit-quality metric is not the best fit-quality metric associated with the virtual face, the previous best fit-quality metric remains. Regardless of the outcome of the best fit-quality metric test, the processor then determines whether all of the virtual masks have been evaluated for this virtual face 1045. If not, the processor returns to step 1010. If, however, all of the virtual masks have been evaluated for this virtual face, then the list of fit metrics is displayed in descending order of fit quality and the method ends 1050.

Figure 11:
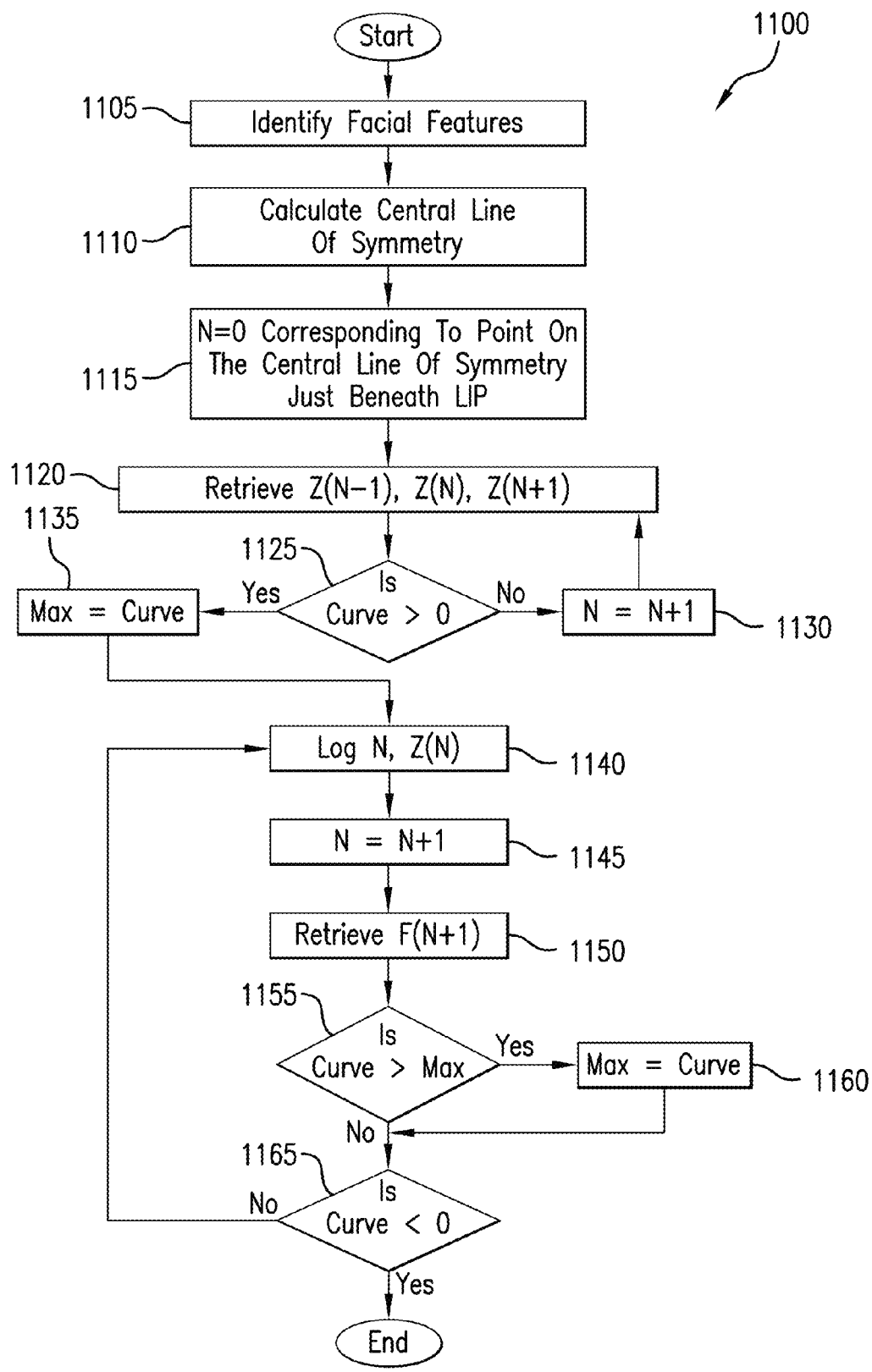
FIG. 11 depicts an exemplary method for aligning a menton region of a virtual mask to a menton region of a virtual face.

FIG. 11 depicts an exemplary method for identifying a menton region of a virtual face. In FIG. 11, an exemplary menton locating method 1100 is described from a vantage point of the processor 165 depicted in FIG. 1. The exemplary menton locating method 1100 may be performed as part of the fit menton region step 1015 of the fit prediction method 1000, for example. The menton locating method 1100 begins by identifying facial features in a virtual face 1105. For example, eyes, nose and a mouth may be identified by characteristics that are unique to each of these features. A nose-tip, for example, may be located by locating the highest Z-elevation location in the virtual face. Then the processor 165 calculates a mid-sagittal plane of symmetry 1110. The processor may, for example, convolve a mirror image of the virtual face with the non-mirrored virtual face. The translated location where the mirrored image best matches the non-mirrored image may then be used to find a line of symmetry. A line of symmetry may be determined by finding the image locations where the mirrored image aligns with the non-mirrored image. Then the processor 165 initializes an index N 1115. The index may correspond to starting location on the line of symmetry from which the processor will begin its search for the menton region of the virtual face. The starting location may, for example, begin just beneath the location of the nose-tip. The processor then retrieves the first three facial elevation points, $Z_{N-1}$, $Z_N$ and $Z_{N+1}$, along the line of symmetry going from the starting point down toward the lower face 1020. A Y-Z curvature value may be calculated from these the three facial elevation points. For example, the following equation may be used as a relative curvature metric:

$$C = -Z_{N-1} + 2Z_N - Z_{N+1}$$

Here, C is a measure of the curvature. The processor then compares the calculated value of curvature with zero 1125.

Figure 12:
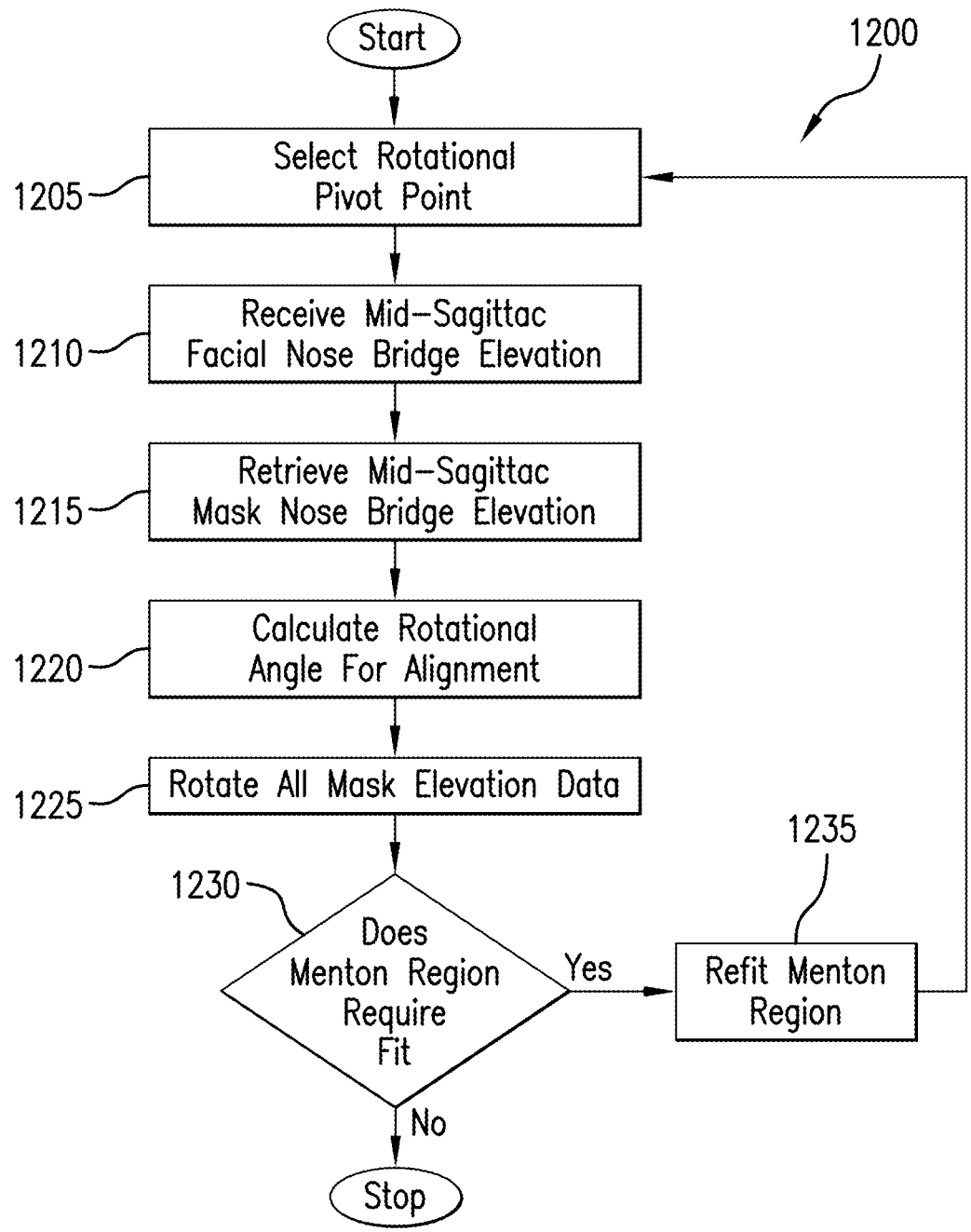
FIG. 12 depicts an exemplary method for determining a rotation angle between a virtual mask to a virtual face.

FIG. 12 depicts an exemplary method for identifying a menton region of a virtual face. In FIG. 12, an exemplary angular alignment method 1200 is described from a vantage point of the processor 165 depicted in FIG. 1. The exemplary angular alignment method 1200 may be performed as part of the rotate mask step 1020 of the fit prediction method 1000, for example. The angular mask alignment method 1200 begins by the processor 165 selecting a pivot point about which the mask may be rotated 1205. The location of the pivot point may be selected to minimize the change in the fit quality of the menton region, for example. In some embodiments, the pivot point may be located substantially at a central location of the fit menton region. The processor 165 then receives mid-sagittal facial nose-bridge elevation data of a virtual face 1210. The processor 165 then retrieves mid-sagittal mask nose-bridge elevation data of a virtual mask 1215. The processor 165 then calculates a rotational angle for aligning the received facial nose-bridge elevation data to the retrieved nose-bridge mask elevation data 1220. The processor 165 then virtually rotates the virtual mask. For example, the processor 165 may calculate new coordinates for each of the virtual mask surfaces based upon the calculated rotational angle for aligning the nose-bridge regions of the virtual mask and the virtual face. These new coordinates may include those for the menton region, in some examples. The processor 165 then determines if the menton region requires being refit 1230. For example, the processor 165 may assess whether the rotated facial contacting surface of the virtual mask remains well-fitted to the menton region of the virtual face after rotation. If the processor 165 determines that refitting the menton region is required, the processor 165 will again fit the menton region of the rotated virtual mask to the menton region of the virtual face 1235. The method will then return to step 1205 and repeat the rotation of the mask by again selecting a pivot point. If, however, at step 1230, the processor determines that the menton region does not require refitting, the method ends.

Figure 13:
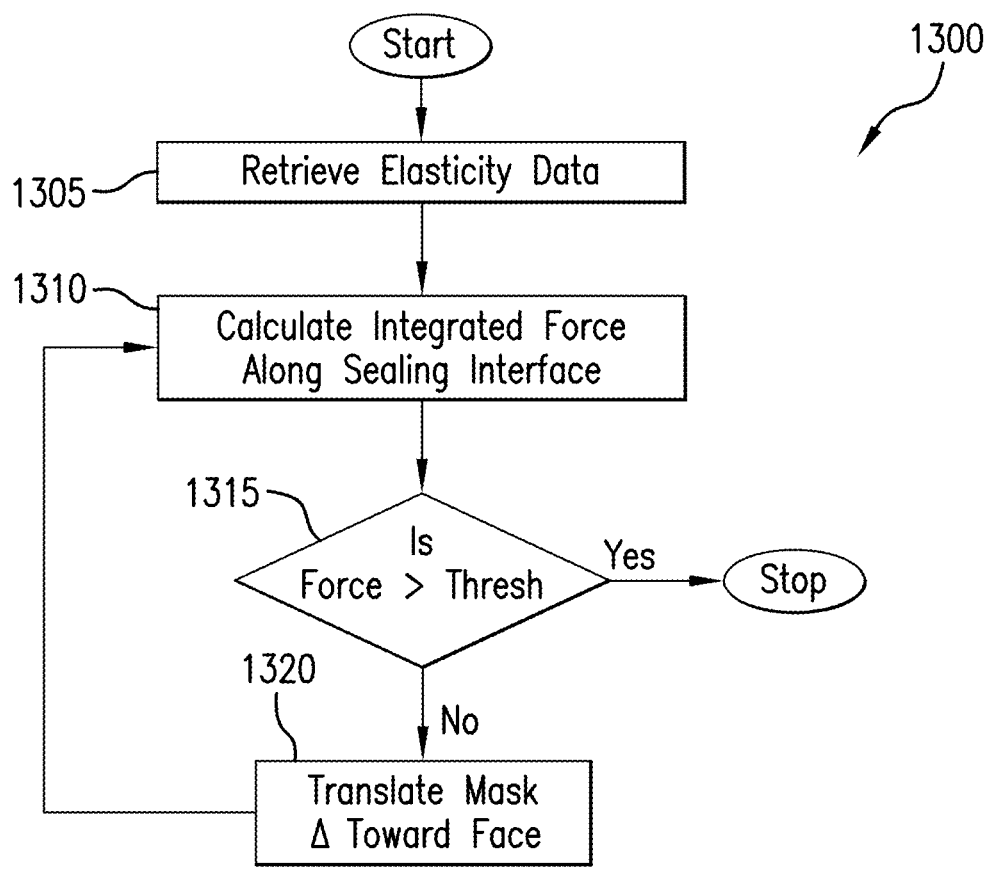
FIG. 13 depicts an exemplary method for pressing a virtual mask into a virtual face.

FIG. 13 depicts an exemplary method for tightening a virtual mask. In FIG. 13, an exemplary mask tightening method 1300 is described from a vantage point of the processor 165 depicted in FIG. 1. The exemplary mask tightening method 1300 may be performed as part of the translate mask step 1025 of the fit prediction method 1000, for example. The mask tightening method 1300 begins with the processor 165 retrieving elasticity data associated with a facial-contacting surface of a virtual mask 1305. In some embodiments, the elasticity data may correspond to a physical parameter of the mask. In some examples, the elasticity data may be a function of the facial-contacting surface location. In an exemplary embodiment, the elasticity data may correspond to a facial skin thickness that varies as a function of facial location. In an exemplary embodiment, the elasticity data represents a combination of physical mask materials and physiological facial statistics. The processor 165 then calculates an integrated force along the sealing interface between the virtual mask and the virtual face 1310. For example, the processor 165 may calculate an integrated force at the mask position aligned at a menton region and rotated to align a nose-bridge region. The processor 165 then determines if the calculated force exceeds a predetermined threshold 1315. If the forced does exceed the predetermined threshold, then the processor translates the virtual mask toward the virtual face by an incremental amount 1320. The direction of translation may be in a fixed Z direction, for example. In some embodiments, the direction of translation may be in a substantially normal direction to the general plane of the sealing interface. In some embodiments, the direction of translation may be determined by the relative forces calculated around the periphery of the sealing interface. The processor then returns to step 1310 and recalculates the integrated force in the translated mask position. If, however, at step 1315, the calculated force exceeds the predetermined threshold, then the method ends.

Figure 14:
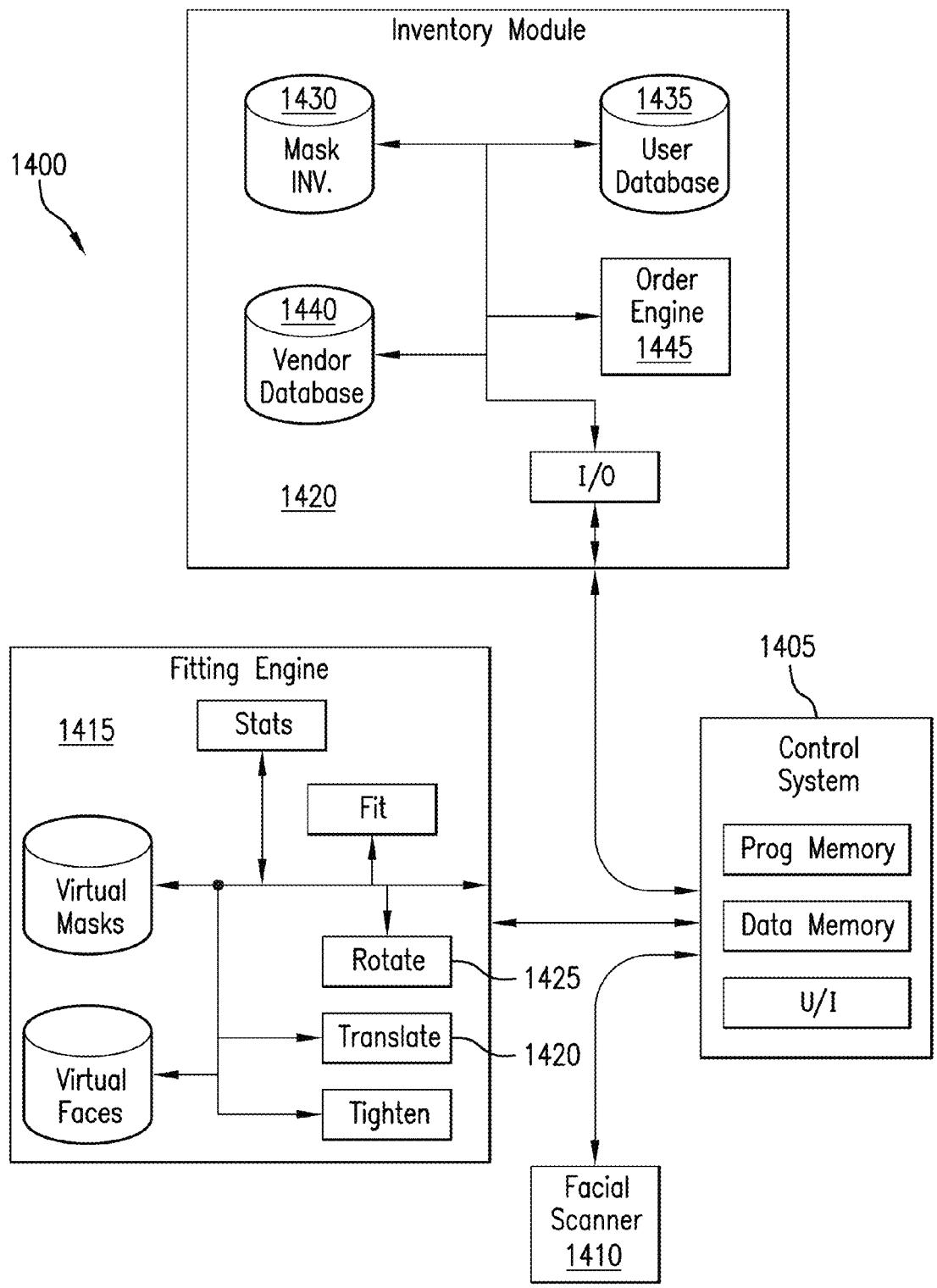
FIG. 14 depicts a block diagram of an exemplary virtual fitting system.

FIG. 14 depicts a block diagram of an exemplary virtual fitting system. In the FIG. 14 depiction, an exemplary virtual fitting system 1400 includes a control system 1405 and a 3D facial scanner 1410. The control system 1405 is in communication with a virtual fitting engine 1415 and an inventory module 1420. The control system 1405 may be running a GUI program retrieved from program memory 1425. The GUI program may contain instructions that, when executed, may coordinate the acquisition of a 3D face, the virtual fitting of a 3D mask to the 3D face, ordering masks from venders, as well as many other PPE related activities, for example. The fitting engine 1415 may perform various alignment operations to align a virtual mask to a virtual face. For example, the fitting engine 1415 may have a rotation module 1425. In some embodiments, the fitting engine 1415 may have a translation module. Some embodiments may have rotation and/or translation modules that operate in more than one dimension. For example, a rotation may be performed about an X-axis, a Y-axis or a Z-axis, or a combination thereof. The fitting engine 1415 may keep statistics for use in future product development activities. The inventory module 1420 may have databases of masks 1430, users 1435, and/or venders 1440, for example. The inventory module 1420 may generate orders using an ordering engine 1445.

Figure 15:
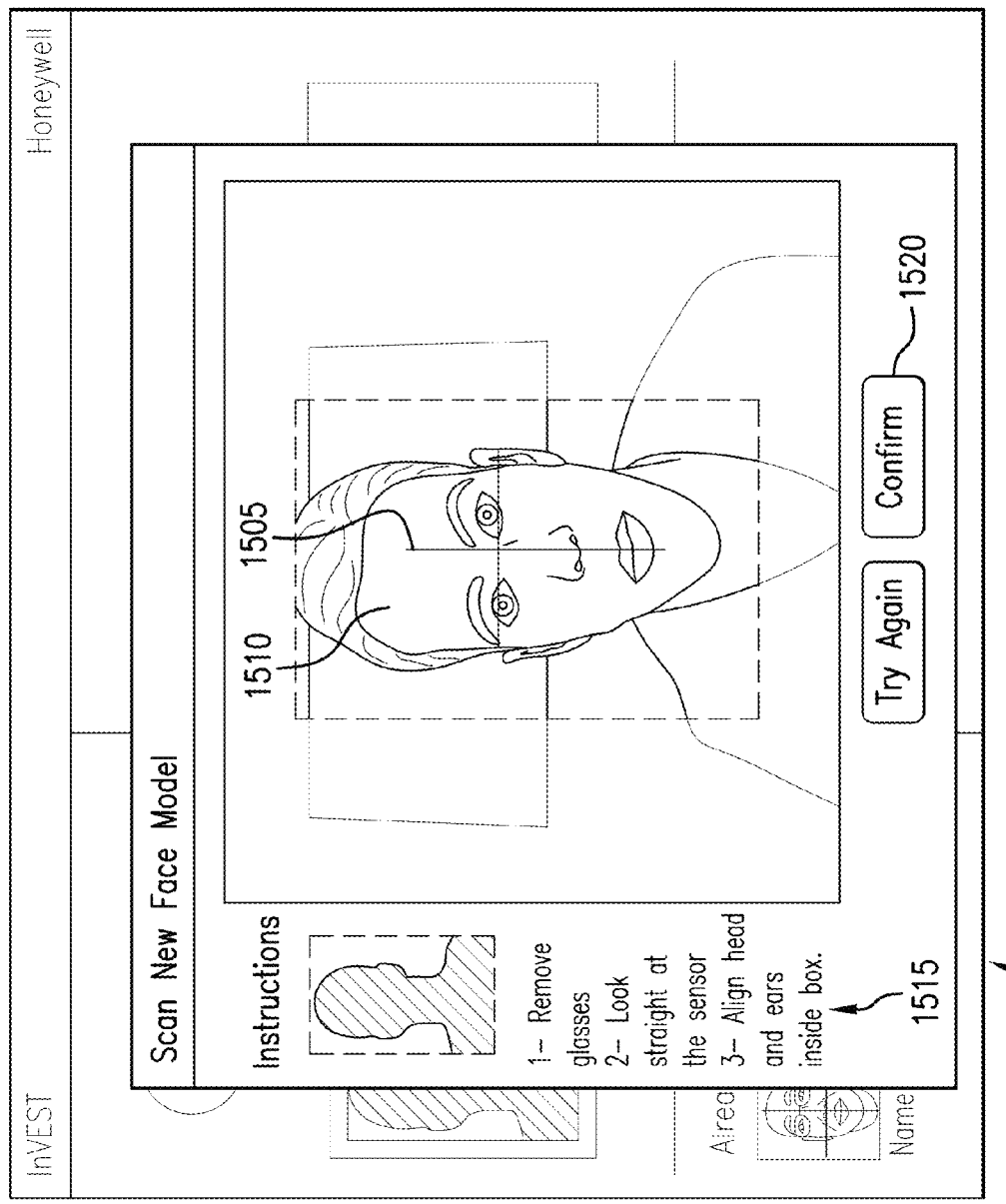
FIG. 15 depicts an exemplary GUI screenshot during a three-dimensional facial acquisition.

FIG. 15 depicts an exemplary GUI screenshot during a three-dimensional facial acquisition. In the FIG. 2 exemplary GUI screenshot 1500, an alignment cross-hair 1505 is superimposed upon a user's real time image 1510. Instructions 1515 are presented to the user on the left-hand side of the screen. The user may be instructed to center the user's face upon the cross-hair and to push a "confirm" button 1520 when ready. The exemplary virtual fitting station may then perform a 3D scan of the user's face 1510. In some embodiments, the user may be instructed to change positions for an additional 3D facial scan. For example, the user may be asked to open the user's mouth. The system may use this information to determine the quality of fit, when the user may be talking, for example. In some embodiments a user's actual body movement may be used to generate a dynamic facial model. Exemplary dynamic modeling systems are described, for example, with reference to at least FIG. 3 in U.S. patent application Ser. No. 13/839,056, entitled "System and Method for Selecting a Respirator," filed on Mar. 15, 2013, the entire disclosure of which is incorporated herein by reference.

Figure 16:
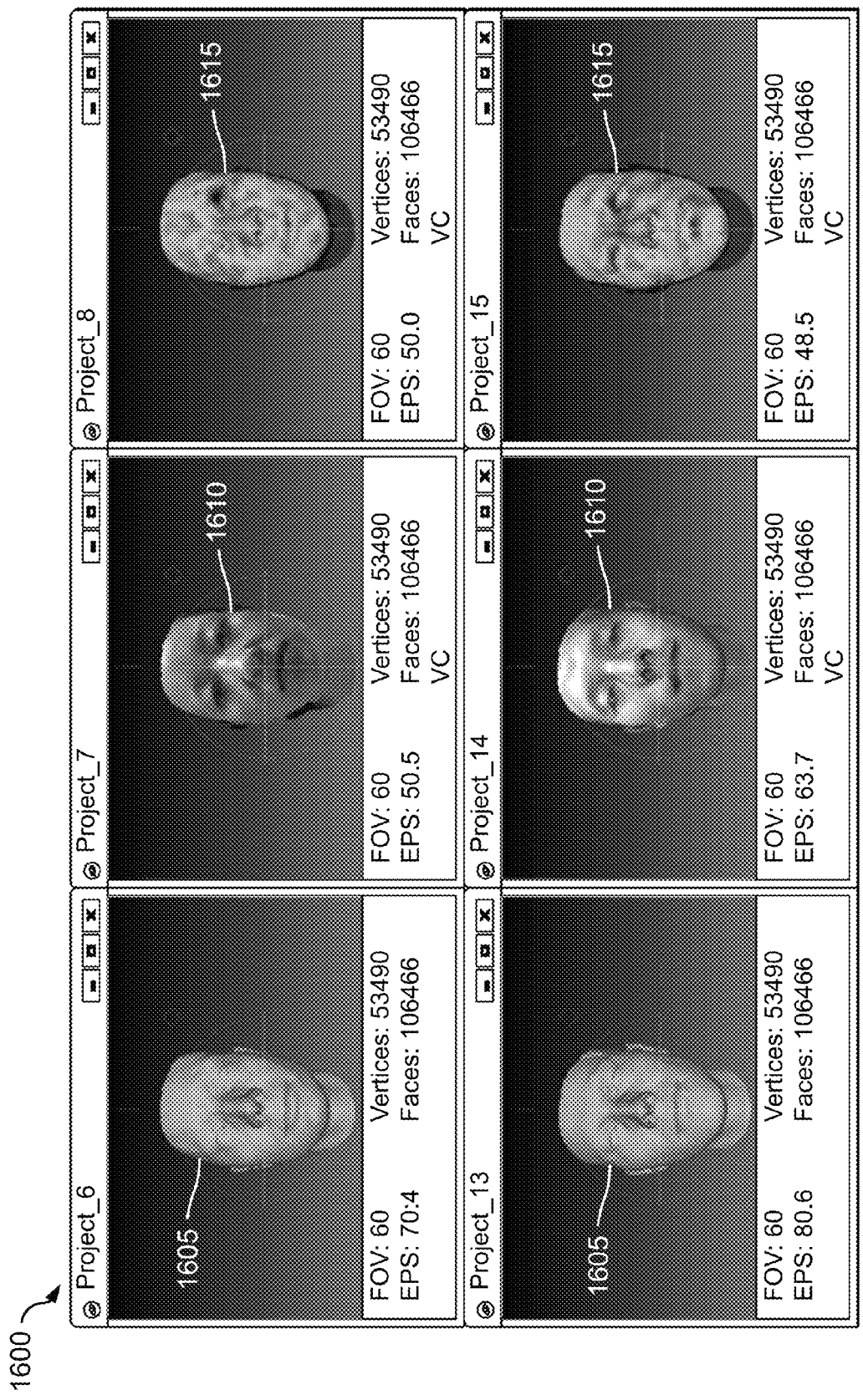
FIG. 16 depicts an exemplary depiction of the facial model compared with a user's face.

FIG. 16 depicts an exemplary depiction of the facial model compared with a user's face. In this figure, an exemplary GUI screenshot 1600 is depicted comparing the computer facial model 1605 of two users to an exemplary virtual fitting system. The screenshot 1600 depicts a capture image 1610 of each user's face and depicts the captured image 1610 alongside the facial model 1605. The system may also compute an error assessment image 1615. The error assessment image 1615 may show the uncertainty of the model as a function of facial position. In some embodiments, the virtual fitting system may permit the user to reject the model and return to a 3D facial scanning stage depicted in FIGS. 15-15. A new 3D facial model may be acquired by a 3D facial scanner, for example.

The user may then be queried as to the type of PPE device the user wishes to fit. The virtual fitting system may then retrieve, from a previously created database, all PPE devices that match the user's criteria. In some embodiments, the virtual fitting station may proceed to computationally determine fitting metrics for each of the matched PPE devices. The station may then sort the matched PPE devices according the computed fitting metrics. For example, the virtual fitting station may present to the user, a screen display depicting the matched PPE device having the best fitting metrics.

Figure 17:
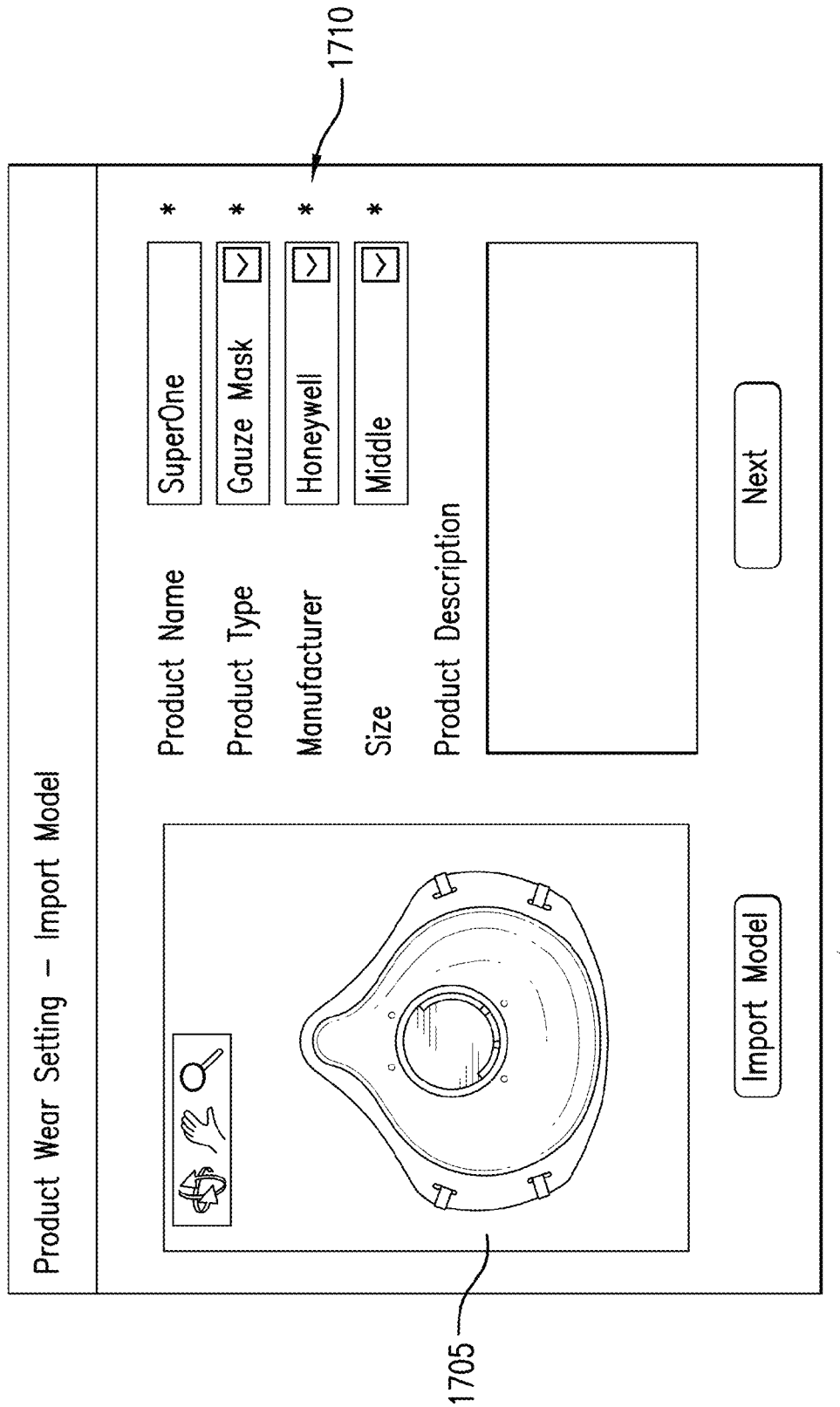
FIG. 17 depicts an exemplary GUI screenshot of a PPE device presentation to a user.

FIG. 17 depicts an exemplary GUI screenshot of a PPE device presentation to a user. In this figure, an exemplary screenshot 1700 depicting a PPE device 1705 along with certain product information 1710. In some embodiments, a virtual fitting device may first ask the user to select from among the matched fitting devices before computing fitting metrics on that device. In some embodiments, a virtual fitting system may present a screenshot containing all the matched devices along with the computed fitting metrics associated with each device. In some embodiments, the screenshot may present all matching devices sorted in decreasing order of a computed fitting metric.

Figure 18:
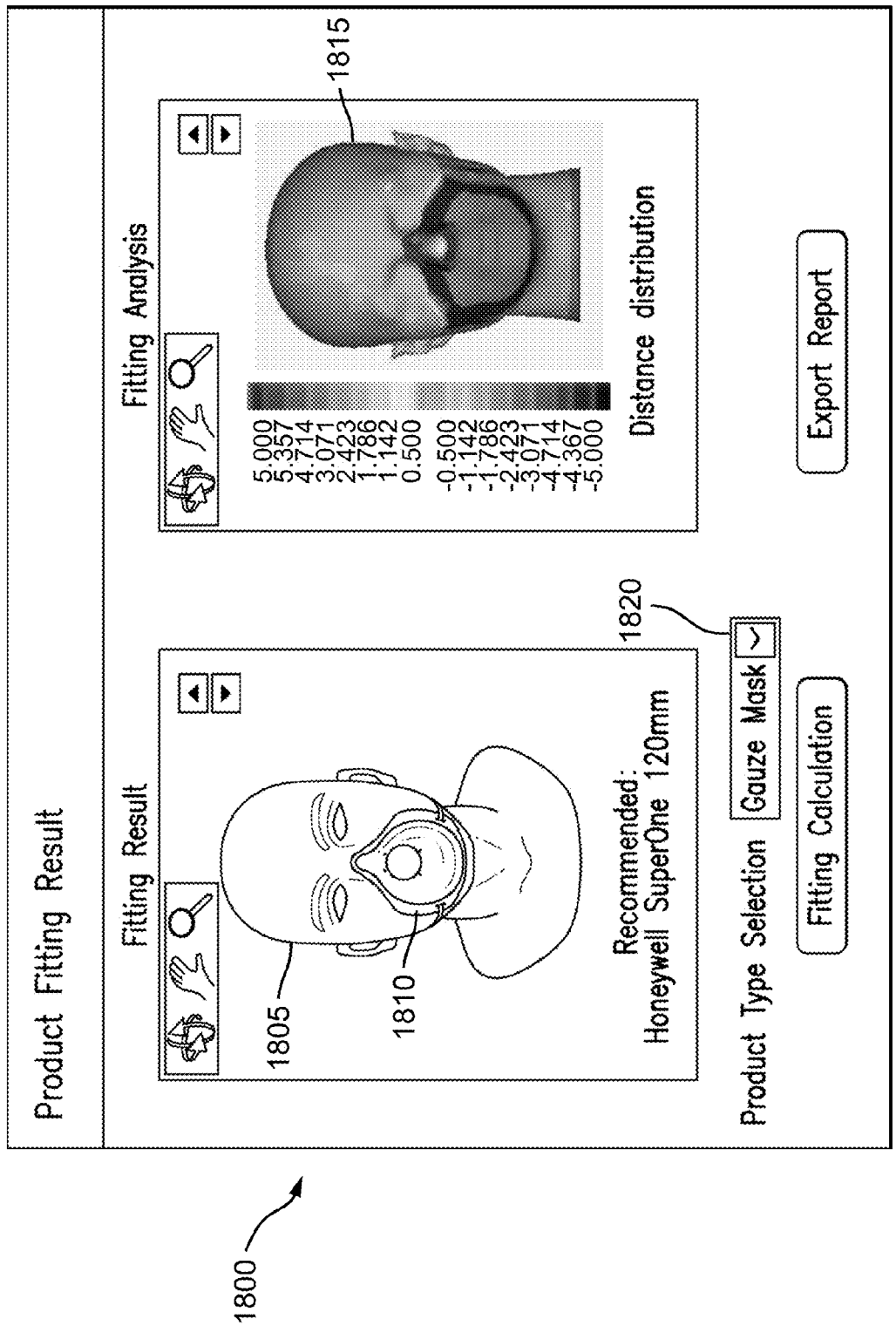
FIG. 18 depicts an exemplary GUI screenshot of the presentation of a fitting metric resulting from the computation of a virtual fit.

FIG. 18 depicts an exemplary GUI screenshot of the presentation of a fitting metric resulting from the computation of a virtual fit. This figure depicts an exemplary GUI screenshot 1800 displaying a representation of the facial model 1805 wearing a selected PPE device 1810. The screenshot 1800 also depicts a graphic 1815 demonstration one of the computed fitting metrics. In this figure, the fitting metric displayed is the distance of the PPE device from the face, when worn. In some embodiments, the metric displayed may be user selected via a radio button, for example. In some embodiments, the metric displayed may be user selectable via a drop-down menu. In some embodiments, the user may select a different PPE device from a drop-down menu 1820 on this display screen 1800. In some embodiments, the user may change the vantage point of the display metric. For example, the user may want to see the fitting metric display from a close-up perspective. Or perhaps the user may want to see the chin fit of the PPE device, and therefore may rotate the display so as to better see the chin. In some embodiments, the user may be able to control the coloration of the displayed metric. For example, the use may change the distance range of coloration from zero inches to 3 inches. A user may want to color only those regions that the PPE device fits between one-quarter of an inch to one-half of an inch, for example. Exemplary methods of computing fitting metrics are described, for example, with reference to at least FIG. 3 in U.S. patent application Ser. No. 61/814,897, entitled "System and Method for Selecting PPE," filed on Apr. 23, 2013, the entire disclosure of which is incorporated herein by reference.

Figure 19:
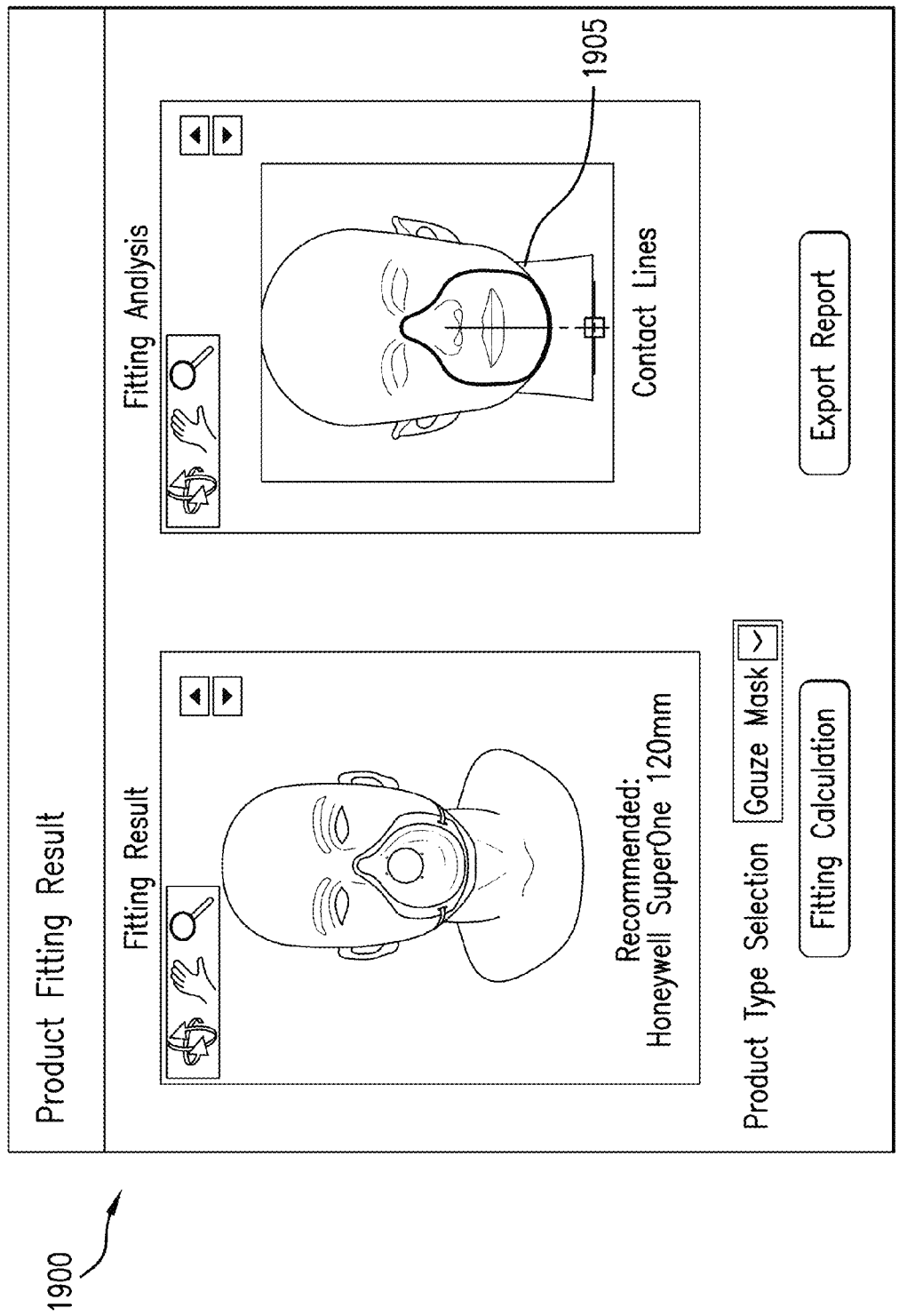
FIG. 19 depicts an exemplary GUI screenshot of the presentation of a facial sealing location of a PPE device as computed during a virtual fit.

FIG. 19 depicts an exemplary GUI screenshot of the presentation of a facial sealing location of a PPE device as computed during a virtual fit. The exemplary FIG. 19 screenshot 600 depicts another exemplary fitting metric. In this figure, the contact line 605 between the PPE device and the user's face is shown. In some embodiments, the virtual fitting station may depict a graphic depicting a predicted comfort level for each contacted location of a user's face, for example. In some embodiments, a virtual fitting station may compute the expected level of heat a user might expect to experience wearing a particular PPE device. In one exemplary embodiment, a virtual fitting station may compute a seal quality for a virtually-fit PPE device. For example, a virtual fitting station may present a graphic in which the contact line is color-coded indicating the quality of fit at the various contact locations. Exemplary methods of computing a PPE-facial seal metric are described, for example, with reference to at least FIG. 5 in U.S. patent application 61/814,905 titled "System and Method for Selecting PPE Fit," filed on Apr. 23, 2013, the entire disclosure of which is herein incorporated by reference.

Figure 20:
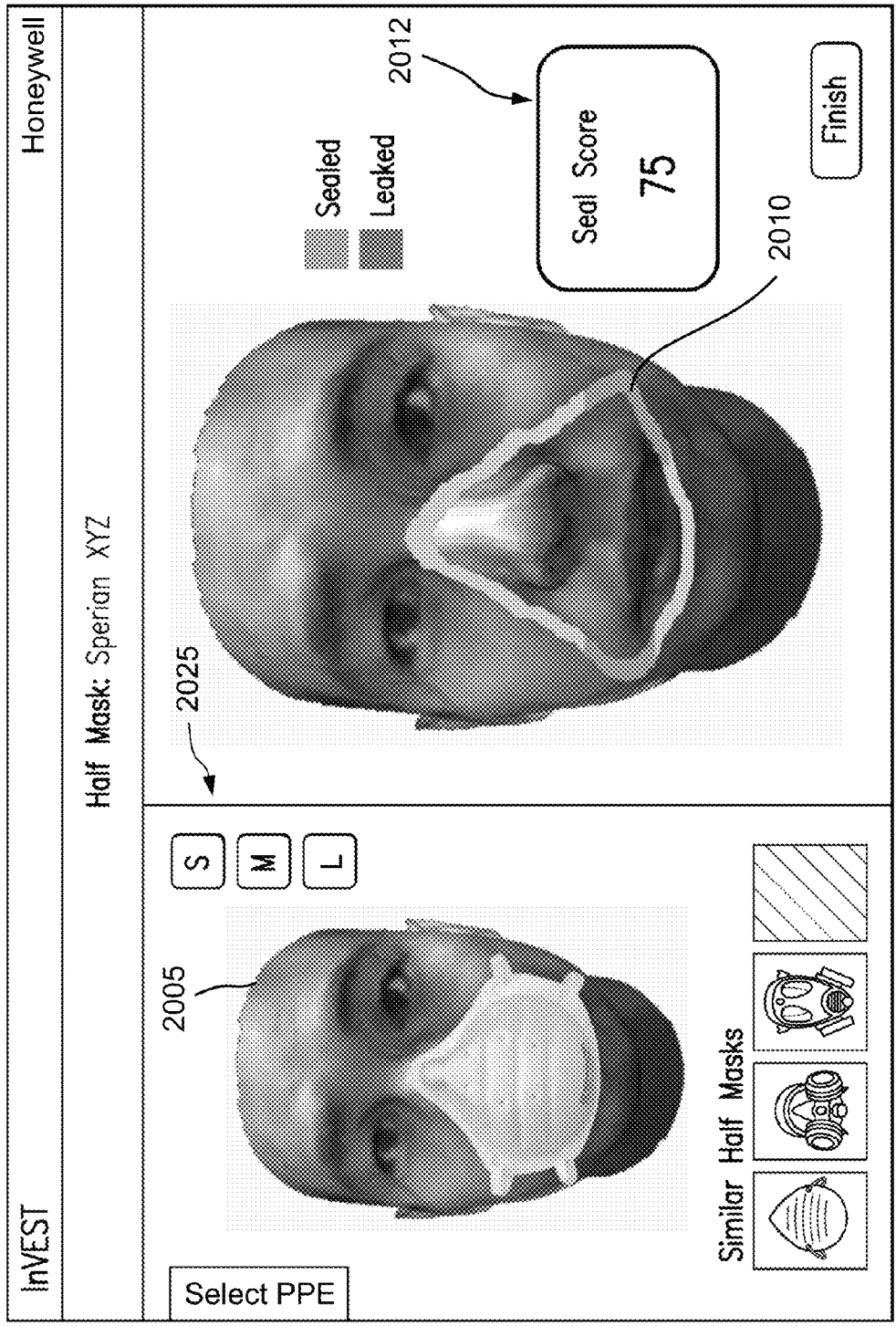
FIG. 20 depicts an exemplary GUI screenshot of a sealing metric of a PPE device as computed during a virtual fit.

FIG. 20 depicts an exemplary GUI screenshot of a sealing metric of a PPE device as computed during a virtual fit. In this figure, an exemplary GUI screenshot 2000 shows a user virtually wearing a PPE device 2005. The screenshot 2000 also depicts a computed fitting metric, in this example, the quality of a PPE-facial seal 2010. The quality of the PPE-facial seal 2000 may be color coded, as depicted here. The quality of the PPE-facial seal may be indicated by a single numerical metric 2012, for example. The screenshot may permit the user to select from a list of PPE devices via a graphical selection area 715. These PPE devices may be have been selected by the virtual fitting station based upon matching criteria. The matching criteria may have been supplied by the user. The matching criteria may have been predetermined by the user's employer, for example. The user may be able to select a different size of the PPE device by selecting among a series of size buttons 2025. In some embodiments, the user may be able to navigate forward and backwards through the various user screens using navigation buttons, for example.

Figure 21:
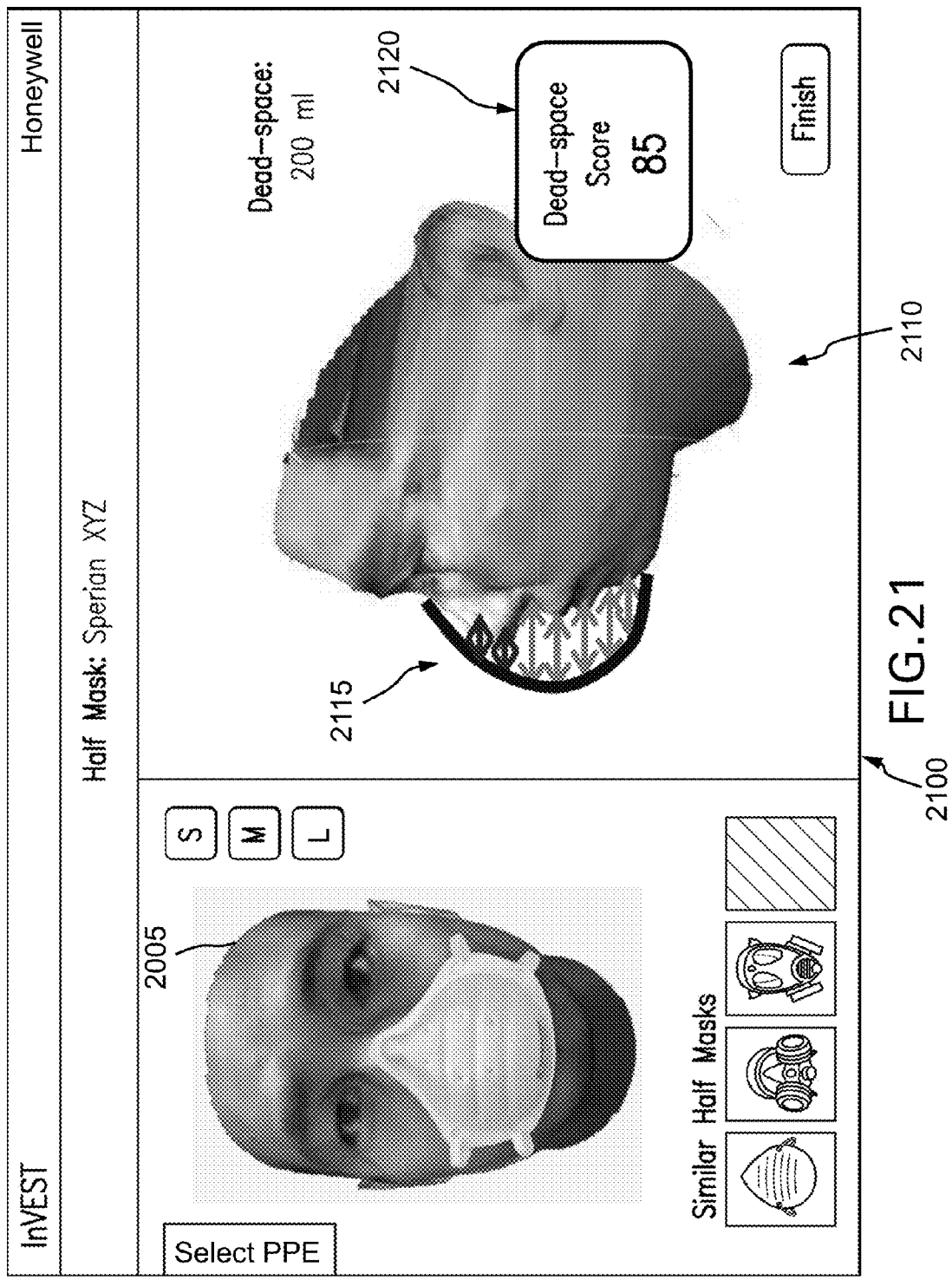
FIG. 21 depicts an exemplary GUI screenshot of a deadspace metric of a PPE device as computed during a virtual fit.

FIG. 21 depicts an exemplary GUI screenshot of a dead-space metric of a PPE device as computed during a virtual fit. In this figure, a screenshot 2100 includes an image of a user wearing a PPE device 2105, and a graphic 2110 displaying a computed fitting metric. In this exemplary figure, the displayed fitting metric is a dead-space score 2115. The dead-space score may be displayed both graphically 2115 and using a single numeric metric 2120 as depicted here. In some embodiments, only the graphical display may be presented. In some embodiments, only a numeric metric will be presented. In some embodiments, more than one metric may simultaneously be presented to the user via a display screen. In some embodiments, if too little dead-space results from a virtual PPE-facial fit, the dead-space score may be low. But in some embodiments, if too much dead-space results from a virtual PPE-facial fit, the dead-space score may also be low. For some PPE devices, too much dead-space may not be considered problematic, for example. But for other PPE device, too much dead-space may facilitate mask collapse during inhalation, for example. Exemplary dead-space metric methods are described, for example, with reference to at least FIG. 8 in U.S. patent application Ser. No. 13/839,186, entitled "System and Method for Selecting a Respirator," filed on Mar. 15, 2013, the entire disclosure of which is incorporated herein by reference.

Figure 22:
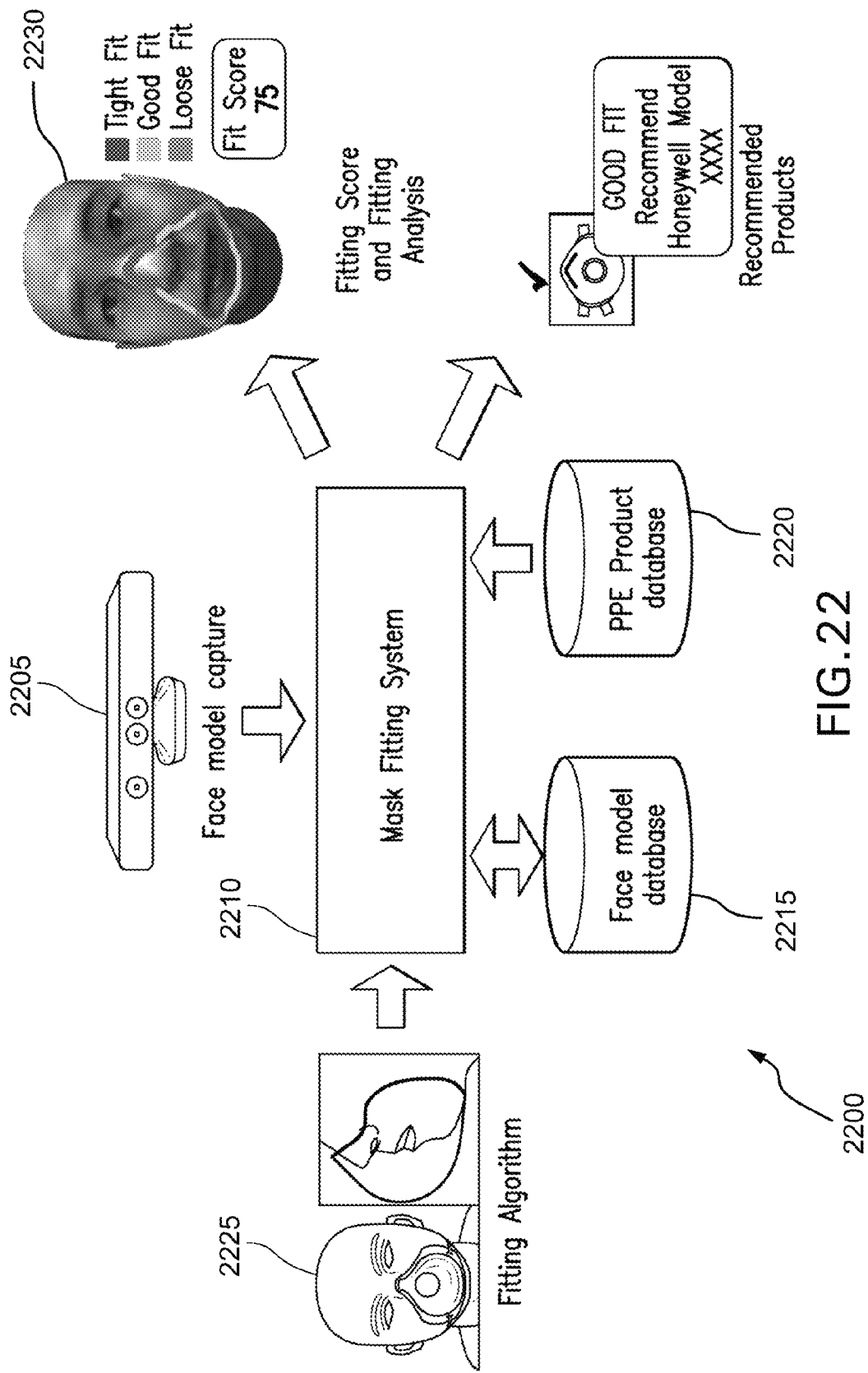
FIG. 22 depicts a block diagram of an exemplary virtual fitting system.

FIG. 22 depicts a block diagram of an exemplary virtual fitting system. In FIG. 22, a block diagram 2200 of an exemplary virtual PPE device fitting includes a face capture module 2205. The face capture module may be used to capture users' 3D topological information. The topological information may then be imported a mask fitting system 2210. The mask fitting system may have a processor that may generate a 3D facial model and store such 3D facial models in a face model database 2215. An employer may keep facial models of its employees in such a database, for example, so that employees' faces need not be reacquired. A PPE product database 2220 may also be maintained by the exemplary virtual fitting station 2200. The mask fitting system 2210 may retrieve both a facial model from the face model database 2215 and a PPE device model from the PPE product database 2220, for example. The mask fitting system may then use a fitting algorithm 2225 to compute fitting metrics for the facial model-PPE configuration. A fitting score 2230 may be output for a user's review. The mask fitting system 2210 may also compute a recommendation 2225 for the employee.

Figure 23:
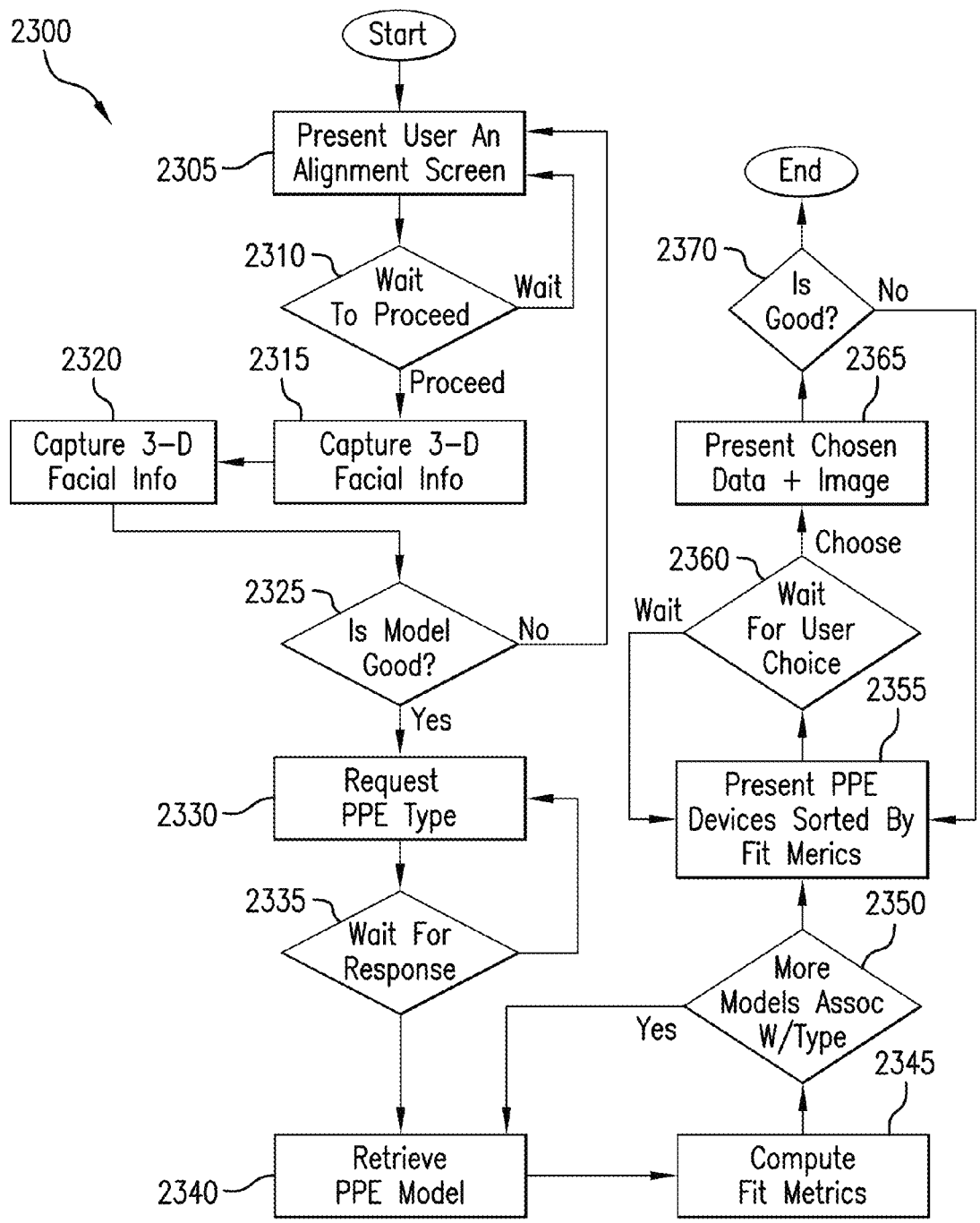
FIG. 23 depicts a flow chart of an exemplary virtual fitting system.

FIG. 23 depicts a flow chart of an exemplary virtual fitting system. FIG. 23 depicts an exemplary virtual mask-fitting method 2300 from the vantage point of a processor in the mask fitting system 2210. The processor begins by presenting to an alignment image for the user to align his live image to an alignment mark 2305. The processor then waits until the user hits a "proceed" button 2310. If the user does not push the proceed button the processor continues to present the alignment screen 2305. If the user does push the "proceed" button, the processor then instructs the 3D scan tool to acquire the user's facial topological information 2315. The processor then creates a 3D facial model using the acquired 3D facial information 2320. The computer then evaluates whether the model is acceptable 2325. If the model is not acceptable, the processor returns to step 2305 and presents the user an alignment screen. If the processor determines that the model is acceptable, however, the processor then requests the PPE criteria from the user 2330. The processor then waits for the user to input the PPE criteria 2335. When the processor receives the user input PPE criteria, the processor retrieves the first matching PPE device model 2340.

The computer then fits the PPE device model to the acquired 3D facial model 2345. The processor computes fitting metrics during this step. The computer then assesses whether any more matching PPE models have yet to be virtually fit 2350. If more matching PPE device models have yet to be virtually fit, the processor returns to step 1040 and retrieves the next matching PPE device model. If all of the matching PPE devices have already been virtually fit, however, the processor then presents the PPE devices to the user 2355. The PPE device devices may be presented in an order of decreasing computed fit metric, for example. The processor then waits for a user to select a PPE device from the presented list 2360. When the user selects a PPE device, the processor then presents the user with a display of the computed data for the selected PPE device along with an image of the user wearing the selected PPE device 2365. The processor then asks the user if the user is satisfied with the selected PPE device 2370. If the user is not satisfied with the selected PPE device, the processor returns to step 2355 and again presents to the user the sorted list of all matching devices. If, however, the user is satisfied with the selected device, the processor finishes the exemplary method.

Although various embodiments have been described with reference to the figures, other embodiments are possible. For example, an exemplary virtually PPE fitting system may be performed on the cloud as a System as a Service (SaaS). A virtual fitting system GUI may run remotely over the internet, for example. In some embodiments, the GUI may operate locally, while the processor computes the fitting metrics remotely. In some embodiments the virtual PPE fitting system may fit a human body part, such as for example a hand. Some embodiments, may project the users actual real-time face upon the computed facial model. For example, the user may be moving in real time, and the selected PPE device may be superimposed upon the user's face creating a real-time virtual fit. The Appendix details many various additional GUI aspects of an exemplary virtual fitting system.

Various embodiments may use more or less menton area elevation data from both the virtual masks and the virtual faces to optimally fit the menton region. In some embodiments, after determining the optimal fit of a virtual mask to a virtual face based upon a menton fit and a sellion rotation, a fit-quality metric may be determined using the sealing surface periphery data. For example, the sealing surface data that may circumscribe the mouth and nose may be used to determine a fit-quality metric. In some embodiments, a dead-space volume, that volume between the virtual facial elevations and the virtual mask interior elevations may be used in determining a quality metric.

In an illustrative embodiment, a computer program product (CPP) tangibly embodied in a computer readable medium and containing instructions that, when executed, cause a processor to perform operations to determine the fit of a virtual mask to a virtual face, the operations may include receiving facial elevation data corresponding to a face of a person. In some embodiments, operations may include retrieving from data memory locations mask elevation data corresponding to a facial mating surface of a mask model. In an exemplary embodiment, operations may include fitting a chin position of the retrieved mask elevation data to a chin region of the received facial elevation data. In some embodiments, operations may include rotating the retrieved mask elevation data toward or away from the received facial elevation data to a nose-bridge region of the received facial elevation data, while maintaining the fitted chin position. In some embodiments, operations may include calculating a quality of a fit between the retrieved mask elevation data and the received facial elevation data at the rotated position.

Personal Protection Equipment (PPE), such as for example respirators, are widely used by persons working in extreme environments. For example, some workplaces require employees to work in hazardous atmospheres. A hazardous atmosphere may be one with excessive dust or particulate contamination, for example. A hazardous atmosphere may be one with chemical vapors present. Some nuclear facilities may have radioactive gas in the working atmosphere. Hospitals may present biological contaminants in the atmosphere. To provide safety for the worker, respirators may be used by the workers who are exposed to such atmospheres. Some employers may require certain employees to wear personal protection equipment to protect the employees from exposure to the hazards.

The quality of fit of personal protection equipment affects the level of protection that may be provided by the equipment. For example, if a respirator fits improperly, the employee wearing the respirator may be exposed to the hazard. If the quality of fit is poor, a respirator may be uncomfortable to wear. Many different types of respirators or other PPE devices are available in the marketplace. And each different piece of equipment may have a different presentation to the wearer. It can be a time consuming job to evaluate the many different equipment devices for the purpose of finding one with a good seal, and yet still is comfortable to wear.

Apparatus and associated methods may relate to a system for predicting a respirator fit by comparing a respirator model in a deformed state to a specific facial model. In an illustrative example, an internal measurement may be calculated between an inside part of the respirator model and the facial model. The internal measurement may be compared against a predetermined threshold to determine a fit of the respirator model, for example. In various implementations, the internal measurement may be a distance and/or a volume between the respirator and facial model. In some implementations, a 3D representation of the respirator model may be displayed upon a 3D representation of the facial model. In some implementations, a color-coded facial display may characterize areas of comfort and discomfort with respect to the respirator model. For example, areas of comfort and discomfort may be objectively determined in view of an applied pressure by the respirator.

In accordance with an exemplary embodiment, an image capture device may generate point cloud data of a body part model and a PPE model. For example, an image capture device may generate point cloud data of a facial area and a respirator. In an exemplary embodiment, point cloud data may be used to overlay a respirator model on a facial model to determine a virtual placement of the respirator model on the facial model. For example, a rigid registration method may be used to align point clouds of the facial model and the respirator model. In some implementations, identifying feature points of the body part model (e.g., nose, mouth) may be correlated with the generated point cloud. In some implementations, a contact line may be determined upon the facial area. Determination of the contact line may provide identification of a portion of a facial area that aligns with the inside part of the respirator.

Various embodiments may achieve one or more advantages. For example, some embodiments may objectively determine whether the hidden, inside part of the respirator will make contact with a portion of the facial area. In accordance with an exemplary embodiment, a predetermined deformation parameter of an outside part (e.g., outside surface) of the respirator may be attributed to a corresponding inside part (e.g., inside surface) of the respirator. The deformation parameter may be determined at each of the vertices or point cloud of the outside and inside parts of the respirator. In an exemplary embodiment, internal measurements may be made between each deformed point cloud or each of the vertices and an aligned part of the facial area to determine a respirator fit.

Apparatus and associated methods may relate to a system for predicting a respirator fit by comparing a specific respirator model to a specific facial model in a dynamic position. In an illustrative example, one or more dynamic positions may be generated by actual user movement and/or simulated user movement. For example, a facial model may be generated by altering a static model in view of actual and/or simulated movements. In various implementations, a facial model may be compared against a variety of respirator models from a respirator model database. In some implementations, a 3D representation of the respirator model may be displayed upon a 3D representation of the facial model.

Some embodiments may predict a realistic fit of a respirator to a facial area by modeling the facial area in one or more dynamic positions. For example, the dynamic positions may be characteristic of facial movements that a user may undergo while wearing the respective PPE, such as for example an open mouth, a raising head, or a bowing head. In an exemplary embodiment, the dynamic positions may be extreme facial movements.

Figure 24:
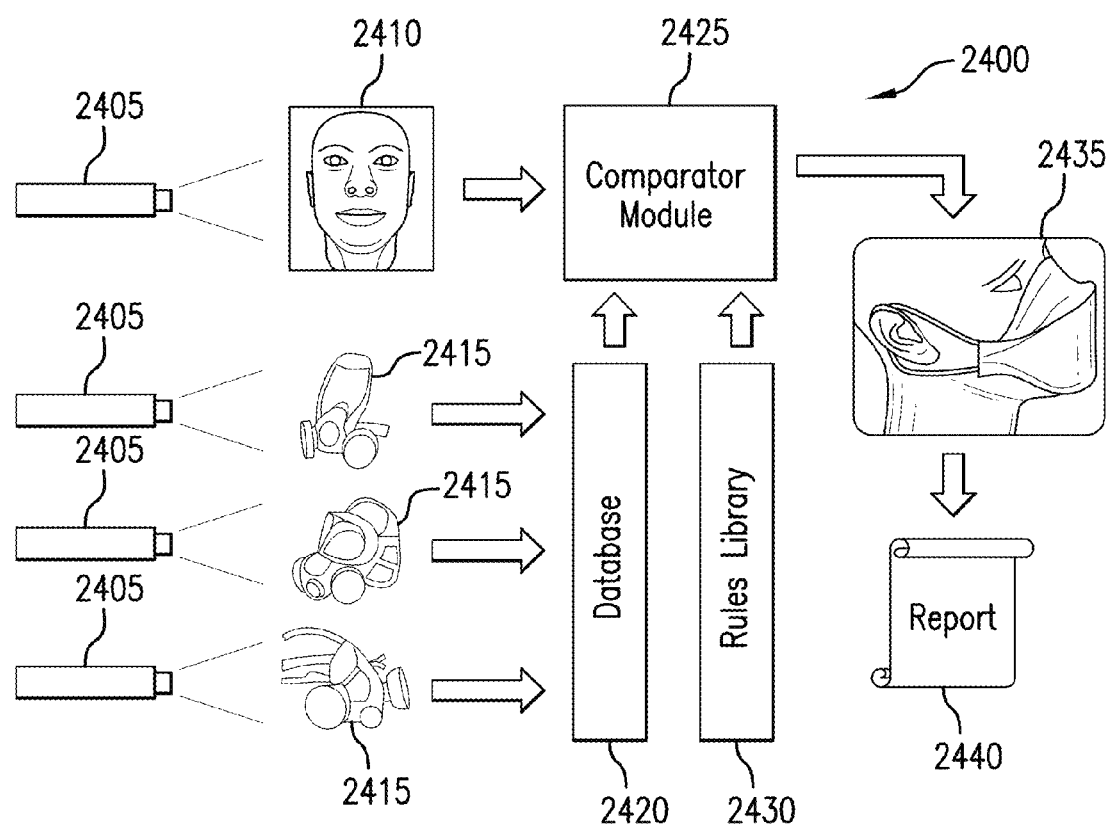
FIG. 24 depicts an overview of an exemplary respirator selection system.

FIG. 24 depicts an overview of an exemplary respirator selection system. A system 2400 for selecting a PPE is illustrated, where the system 2400 may provide recommendations to a user on which PPE will provide an optimal fit, or provide a best fit among available PPE. A fit level of the PPE upon the user may be determined by a variety of factors determined by the user, employee, and/or manufacturer. For example, an amount of predicted leakage of ambient air through a sealing edge of the respirator may be a determined factor for determining a fit level of the respirator on a facial area of the user. In an exemplary embodiment, if a respirator were to permit a leakage at a rate beyond a predetermined threshold, the respective respirator may be given a low score and/or a non recommendation. In another exemplary embodiment, a force applied by the respirator upon a facial area of the user may be a determinant factor on a recommendation of a particular respirator type of size. If the respirator is predicted to apply pressure to the facial area at a rate or force exceeding a threshold, the respirator may be given a low score and/or a non recommendation because of a possible low comfort level provided to the user by the respirator, for example.

The system 2400 may provide fit recommendations or scores based upon captured and analyzed images of the user body part (e.g., facial area) and PPE (e.g., respirator). In the depicted example, the system 2400 include one or more image capture devices 2405 for capturing representations of a user body part 2410 and/or a type of PPE 2415. In the depicted example, the user body part 2410 is a user facial area. The PPE 2415 may be a respirator, for example. In an exemplary embodiment, a series of two-dimensional (2D) images may be captured by the image capture device 2405 from which a three-dimensional (3D) image may be assembled. In other exemplary embodiments, a 2D image may be used to determine a PPE fit. In other exemplary embodiments, the image capture device may capture a 3D representation of the body part 2410 and/or the PPE 2415. In some examples, facial coordinate data representative of a shape of a facial area and respirator coordinate data representative of a respirator shape may be analyzed to provide a fit recommendation. In an exemplary embodiment, the system 2400 may load previously captured and/or generated body parts 2410 and/or PPE 2415.

The system 2400 may be used for selecting a variety of PPE 2415 to be worn on the intended body part 2410. For example, in certain embodiments the system 2400 may predictively choose an optimal fitting glove to fit a user hand. In other exemplary embodiments, the system may choose an optimally fitting helmet to fit a head of a user. In an exemplary embodiment, several respirator point cloud data sets each indicative of a specific size and shape respirator 2415 may be stored in a database 2420. For example, each respirator that an employer offers to employees may be analyzed with associated representative point cloud data, where the representative point cloud data may be stored in a database 2420. In an exemplary embodiment, the point cloud data may include x, y, z coordinates which may be assembled to form a 3D image of the intended PPE 2415 and/or user body part 2410. In an exemplary embodiment, the database 2420 may be accessible over a wide-area network (e.g., Internet) to permit a wide selection of PPE 2415 to users without the need to personally capture data representative of each eligible PPE 2415.

A comparator module 2425 compares the PPE 2415 with the body part 2410 to determine whether the PPE 2415 will properly fit the respective body part 2410. In an exemplary embodiment, the PPE 2415 is overlaid upon the body part 2410. For example, a point cloud and/or vertices may be aligned between the PPE 2415 and the body part 2410. In an exemplary embodiment, the comparator module 2425 uses a set of predetermined rules from a rules library 2430 to determine whether the PPE 2415 properly fits the body part 2410. For example, the rules may require the sealing edge of a respirator not to be in contact with the mouth of the user. In another exemplary embodiment, the rules may require the respirator to have a surface area as large as the respirator-receiving portion of the facial area of the user. In another exemplary embodiment, the rules may identify a captured body part, such as for example a facial area, and direct the comparator module to only compare respirators from the database with the body part. In another exemplary embodiment, the rules may identify a captured body part, such as for example a hand, and direct the comparator module to only compare gloves from the database with the body part and not to compare respirators with the captured body part (e.g., hand).

After a fit of the evaluated PPE 2415 and body part 2410 has been determined, a simulator module 2435 may display the fit. For example, the simulator module 2435 may display a representation of the respirator worn by the specific facial area of the user. In some examples, a predicted tightness or looseness of the PPE 2415 relative the body part 2410 may be emphasized in the simulator module 2435. For example, a predicted leakage between the sealing edge of the respirator and the facial area may be emphasized. A report 2440 may be outputted to the user to assist in providing a recommendation on fit levels of each compared PPE 2415. In some examples, a list of evaluated PPE 2415 may be included in the report 2440 with each of the evaluated PPE 2415 having a score or fit level assigned. In some examples, only recommended PPE 2415 may be provided in the report 2440. In some examples, only the highest scoring three or five PPE 2415 may be provided in the report 2440.

Figure 25:
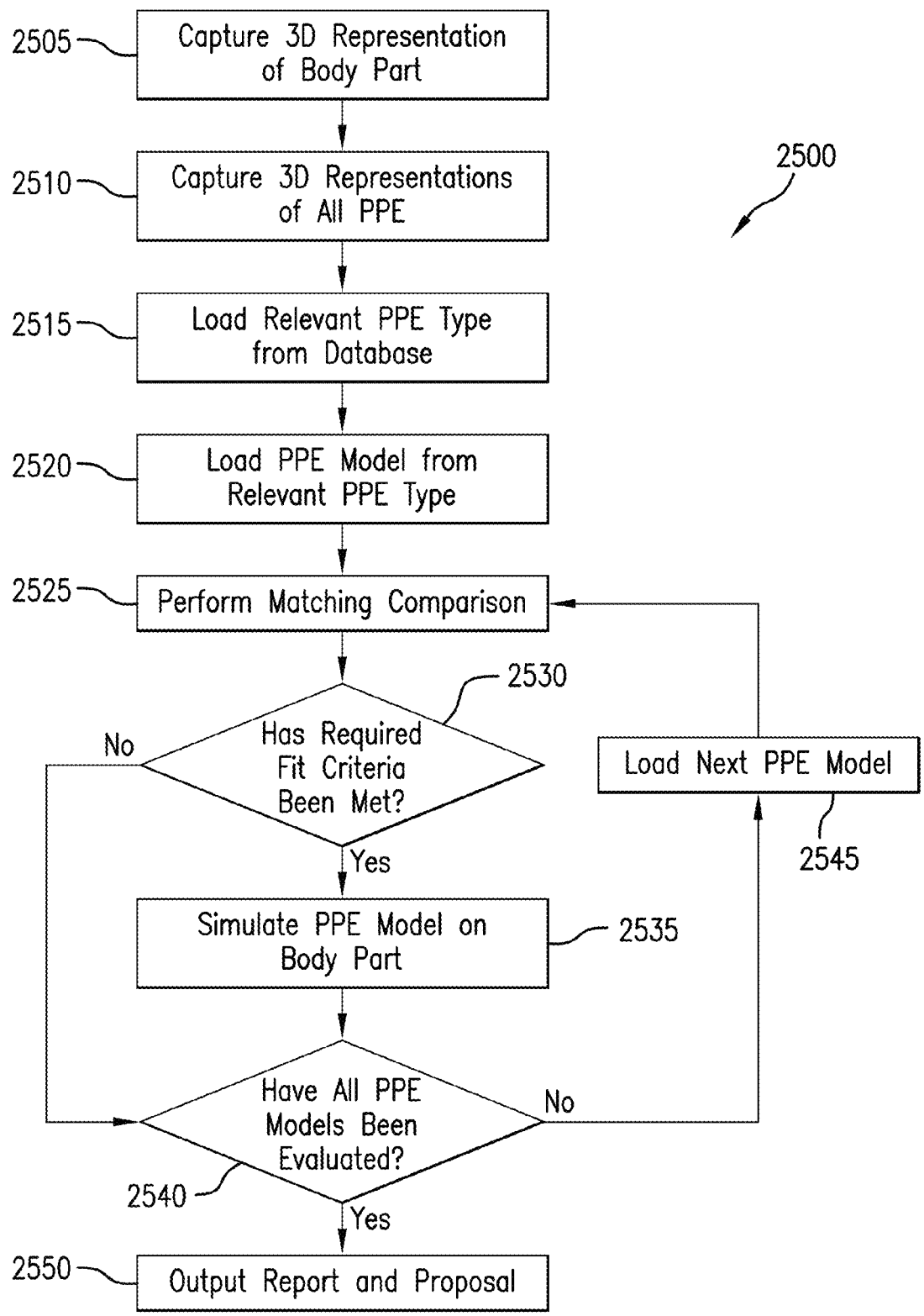
FIG. 25 depicts a flowchart of an exemplary PPE selection system.

FIG. 25 depicts a flowchart of an exemplary PPE selection system. In an exemplary PPE selection system 2500, a determination may be made of whether one or more PPE models fit a specific body part. In an exemplary embodiment, the determination may be made by software operated on a processor module. For example, the software may determine which respirator of a plurality of respirator models from a respirator type database fits a specific facial area of a user and output a recommendation to a user.

More specifically, data representing an exemplary body part may be captured as in step 2505. In an exemplary embodiment, the data may be captured by an image capture device. For example, an image capture device may scan a body part to build a 3D representation of the body part. In another exemplary embodiment, data representing the body part may be retrieved or computationally loaded. In an exemplary embodiment, the body part data may be retrieved from a body part database having specific body part shapes stored at an earlier date. In other exemplary embodiments, the data representative of a body part may be a generic body part computationally generated or morphed from one or more models. In an exemplary embodiment, the representative body part may be a facial area of a user.

Additionally, data representing one or more types of PPE (e.g., helmets, gloves, PPE) may be captured as in step 2510. In an exemplary embodiment, the data may be captured by an image capture device. For example, an image capture device may scan PPE to build a 3D representation of the PPE. In another exemplary embodiment, data representing the PPE may be retrieved or computationally loaded. In an exemplary embodiment, the PPE data may be retrieved from a PPE database having specific PPE shapes stored at an earlier date. In an exemplary embodiment, the representative PPE may be a respirator.

A particular type of PPE (e.g., helmets, gloves, PPE) to be worn over or upon the loaded body part may be retrieved or computationally loaded as in step 2515. For example, a PPE type including respirator models may be loaded if the intended body part may be a facial area. In another exemplary embodiment, a PPE type having gloves may be loaded if the intended body part may be a hand.

A first PPE model from the loaded relevant PPE type may be retrieved as in step 2520 to be compared via a comparator module with the captured body part as in step 2525. Each PPE model may be distinguishable because of a size, shape, or other criteria which may affect the fit of the PPE on the user body part. The comparison may determine whether the PPE model has a shape that will permit an acceptable fit over the shape of the body part. For example, the PPE model may be required to meet or exceed one or more thresholds or rules previously determined as indicative of proper or optimal fitting criteria. In some exemplary embodiments, the PPE model may be required to fit the body part in both static and dynamic states of the body part.

If the PPE model is determined to fit the body part as illustrated in step 2530, the PPE model may be simulated on the body part as in step 2535. In an exemplary embodiment, the PPE model and body part may be displayed to the user in a 3D representation. In some exemplary embodiments, the user may rotate and pan a 3D representation of the simulated body part and PPE model. In some exemplary embodiments, the simulated representation may provide visual feedback to the user detailing areas of the PPE model that are not predicted or determined to fit the respective body part. For example, one or more colors may be overlaid upon the representation to indicate areas upon the body part that are predicted to be uncomfortable as a result of wearing the PPE model. In other examples, a blinking or flashing area may indicate an area of the PPE model that does not conform to a minimum threshold determined to be required to provide a proper and/or comfortable fit. For example, a portion of a sealing edge of a respirator may blink if a leak is predicted to be present in the respective portion.

After the first PPE model is determined to fit and simulated to the user, the software may determine if there are any other PPE models in the chosen PPE type group that are to be evaluated against the respective body part as illustrated by step 2540. If so, the software cycles to a second PPE model as illustrated by step 2545 and repeats the process of steps 2525-2540. If there are no more PPE models from the PPE type group, a report and proposal may be generated for output to the user as illustrated in step 2550. In some exemplary embodiments, the report and proposal may include the top three PPE models that have the best fit with respect to the specific body part. In some exemplary embodiments, the top PPE models or all of the PPE models evaluated may be provided with a fit score to the user. In some exemplary embodiments, a different PPE type group may require comparison with the body part, in which case some or all of the process may be repeated.

Figure 26:
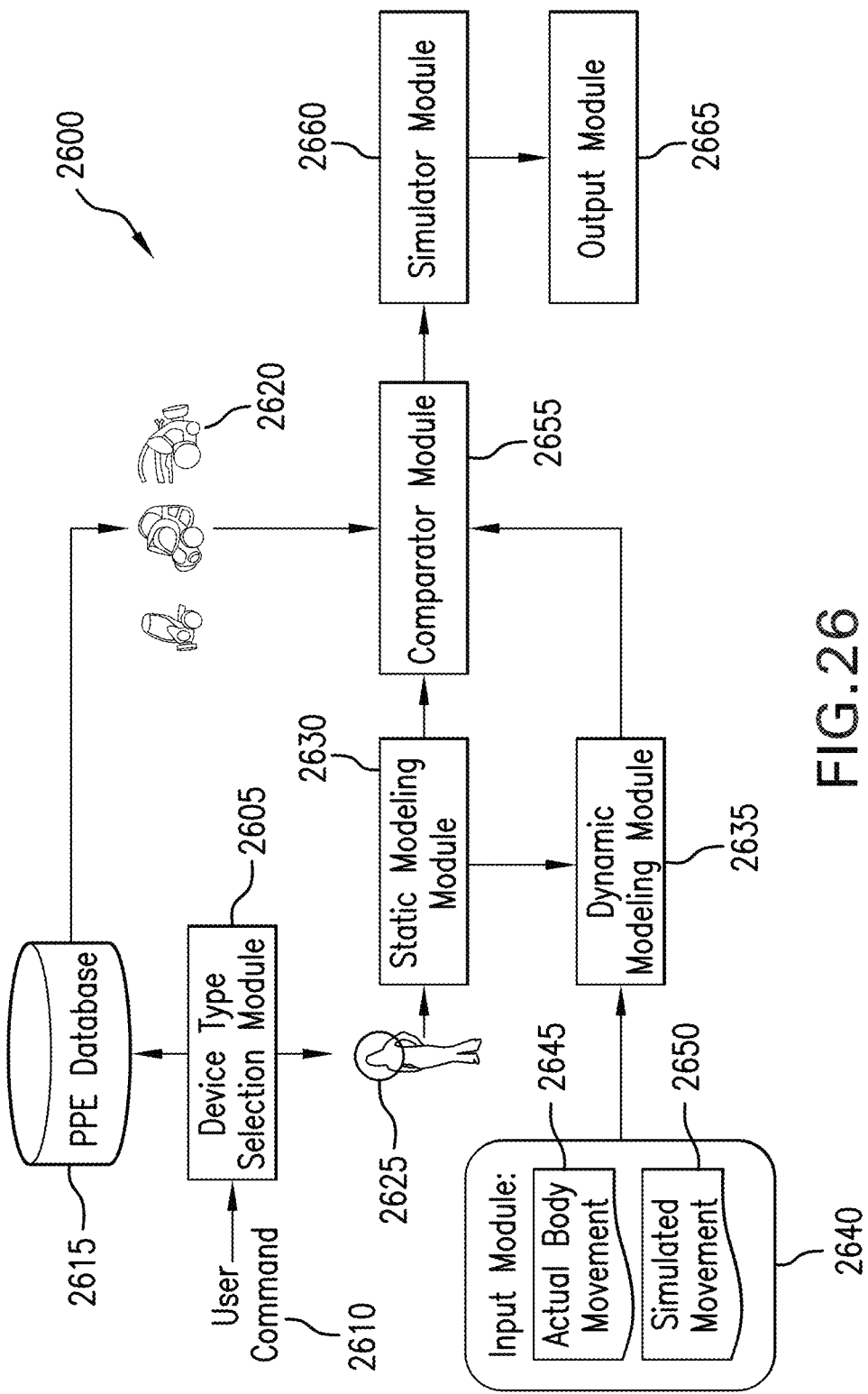
FIG. 26 depicts an overview of an exemplary PPE selection system.

FIG. 26 depicts an overview of an exemplary PPE selection system. A PPE selection system 2600 may be used to select an optimal fit PPE for a user body part during dynamic conditions of the user body part. The PPE selection system 2600 includes a device type selection module 2605 for receiving a command from a user 2610. In an exemplary embodiment, the device type selection module 2605 sends commands to a PPE database 2615. The PPE database 2615 may include a variety of types of PPE 2620, such as for example gloves, respirators, and helmets. In an exemplary embodiment, the device type selection module 2610 may relay a command 2610 indicative of a particular type of PPE 2620, such as for example a facial respirator. In an exemplary embodiment, the command 2610 may be indicative of a particular user body part 2625 to be matched with the PPE 2620 from the PPE database 2615.

In some exemplary embodiments, the device type selection module 2605 may direct an image capture device (not shown) to capture a 2D or 3D image of the selected body part 2625. In some embodiments, the PPE 2620 may be modeled in a corresponding 3D shape. In some exemplary embodiments, one or more device range rules may define a capture range of the body part 2625 for the corresponding PPE 2620. For example, with half-mask respirators, the device range rules may define a capture range as the user face. In an exemplary embodiment of multiple PPE candidates, a capture range computing step may calculate a maximum facial area range that may accommodate the PPE and then correlate the range with each PPE to determine whether the respective PPE fits within the facial area range.

Once the user body part is captured or retrieved, such as for example from a database, the user body part may be modeled using a static modeling module 2630. The static modeling module generates a 3D model of the user body part to be used by a dynamic modeling module 2635. The dynamic modeling module 2635 communicates with an input module 2640 for generating dynamic models of the user body part 2625. In one exemplary embodiment, the input module 2640 communicates actual body movement 2645 to the dynamic modeling module 2635 for generating a dynamic model using actual movement from the user. In another exemplary embodiment, the input module 2640 communicates simulated movement 2650 to the dynamic modeling module 2635 to generate a dynamic model based upon a simulated body part movement.

By using a dynamic model, a more realistic fit may be realized between the user body part and the PPE, since a user generally undergoes some movement while wearing the PPE. The dynamic model may then be compared with the PPE models 2620 from the PPE database 2615 by a comparator module 2655. The comparator module 2655 may determine a fit level of the PPE model 2620 with the dynamic model from the dynamic modeling module 2635 based on a variety of predetermined criteria or rules. For example, the comparator module 2655 may evaluate a size of the PPE model 2620 with the dynamic model in an extreme position (e.g., open mouth) to determine whether the PPE (e.g., respirator) will fit the user body part (e.g., facial area) in the extreme position. The calculated results of the comparator module 2655 may be summarized for output and visualization.

In an exemplary embodiment, the comparator module 2655 may fit the PPE model candidate 2620 to the dynamic model set according to mapping rules. The comparator module 2655 may then calculate the difference between the PPE model candidate 2620 and dynamic model outputted from the dynamic modeling module 2635. According to a set of predetermined evaluation rules, a fit score of each PPE model 2620 may be provided relative the dynamic model. Lastly, the comparator module 2655 may output an optimal fit PPE 2620 based on simulated comfort and fit. In an exemplary embodiment, a respective fit of the PPE 2620 may be visualized by color coding for user.

In an exemplary embodiment, the result from the comparator module 2655 may be outputted to a simulator module 2660 for display to a user through an output module. In an exemplary embodiment, the simulator module may graphically overlay the 3D PPE model 2620 upon a 3D representation of the user body part 2625 to illustrate to the user the PPE model 2620 being virtually worn on the user body part 2625. In some exemplary embodiments, a fit level, score, or color may accompany the graphical illustration for ease in interpreting the results.

In an exemplary embodiment, the output module 2665 may comprise a display module. In some exemplary embodiments, the output module 2665 may comprise a printed report. In some exemplary embodiments, the report may provide 3D visual representations of the PPE virtually worn by the user. In some exemplary embodiments, the report may provide a detailed list of a fit level or score of each evaluated PPE with respect to a region of interest of the user. In some exemplary embodiments, the report may provide a color-coded graphical representation of a PPE virtual fit on the user. In some exemplary embodiments the color-coded graphical representation may illustrate, through color-coding, different levels of pressure as applied to the user by the PPE when virtually worn.

Figure 27:
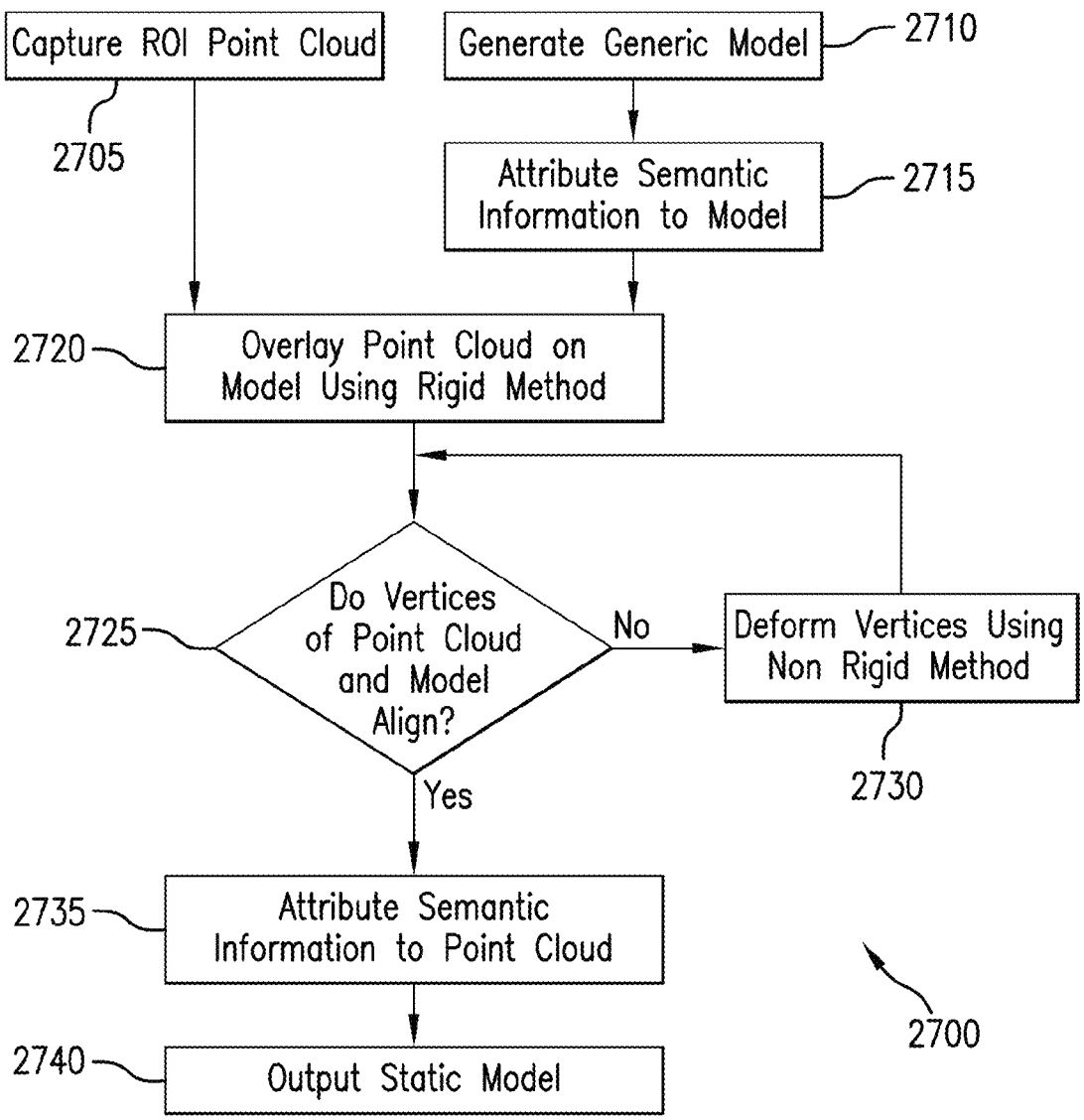
FIG. 27 depicts a flowchart of an exemplary process of a static modeling module.

FIG. 27 depicts a flowchart of an exemplary process of a static modeling module. A static modeling module 2700 may be used to generate an objective static 3D model of a body part. The static model may be used in dynamic modeling processes. In some exemplary embodiments, the PPE may be compared directly to the static model if dynamic comparison is not necessary. In an exemplary embodiment, a static model of a facial area may be generated with the static modeling module 2700. In some exemplary embodiments, the generated static model may be in 2D form.

When generating the static model, the module 2700 first captures a region of interest (ROI) point cloud of a user as in step 2705. The ROI may be the portion of the body that corresponds to the evaluated PPE. For example, when evaluating respirator fit, the ROI may be a facial area of the user. In an exemplary embodiment, the point cloud may include x, y, z coordinates assembled to form a 3D image of the respective body part.

A generic model may also generated as illustrated in step 2710 to generically match the body portion captured by the point cloud as in step 2705. For example, if a facial area is the ROI, the generic model may be representative of a generic user face. In exemplary embodiments, the generic model may be retrieved from a database of generic models. In some exemplary embodiments, a preliminary screening process may be completed to find a generic model being close in shape to the captured ROI. Predetermined semantic information is attributed to the generic model as in step 2715. The semantic information may be distinguishable body feature points of the corresponding body part. For example, a facial area may include semantic information associated with the eyes, ears, mouth corners, and a nose tip. The semantic information may be attributed to the vertices of the generic model, for example. In an exemplary embodiment, a set of rules which define the semantic information may include MPEG4 format definition rules.

The point cloud of the ROI is then overlaid on the generic face model by a rigid method as in step 2720. In an exemplary embodiment, the rigid method may include a rigid registration or alignment of vertices of the ROI and vertices of the generic model. In an exemplary embodiment, the aligned vertices may correspond to proximally similar or equivalent locations on the modeled body part. For example, the nose portion of the point cloud of the ROI may be aligned with nose portion of the generic model.

The module 2700 then determines whether the vertices of the point cloud align or match to an acceptable level or threshold as illustrated in step 2725. For example, if the vertices of the point cloud do not exactly align as determined by a predetermined threshold, the vertices of the point cloud and the generic model are deemed not to align to an acceptable level. If the vertices do not align to an acceptable level, the vertices of the generic model may be deformed to fit the overlaid point cloud by a non-rigid registration method. In an exemplary embodiment, a non-rigid registration method may include blending the non-aligning vertices of the generic model with neighboring vertices. In another exemplary embodiment, certain vertices of the generic model may be moved a predetermined allowable distance to reach an alignment with the point cloud of the ROI.

Once alignment is reached with the vertices of the point cloud and vertices of the generic model, the semantic information of each vertex on the generic face model may be attributed to the point cloud. For example, the vertices of the point cloud may receive the semantic information and be stored within the properties of the point cloud such that each of the points in the point cloud may include identification properties corresponding to a location of the point in the point cloud. For example a point of the point cloud located at a position corresponding to a nose tip may include semantic information identifying the point as "nose tip". The static model having the point cloud with semantic information may then be outputted as in step 2740. In an exemplary embodiment, the static model may be outputted to the dynamic modeling module. In another exemplary embodiment, the static model may be outputted to a comparator module. In yet another exemplary embodiment, the static model may be outputted to a simulator module. In an exemplary embodiment, the static model may be a 3D representation.

Figure 28A:
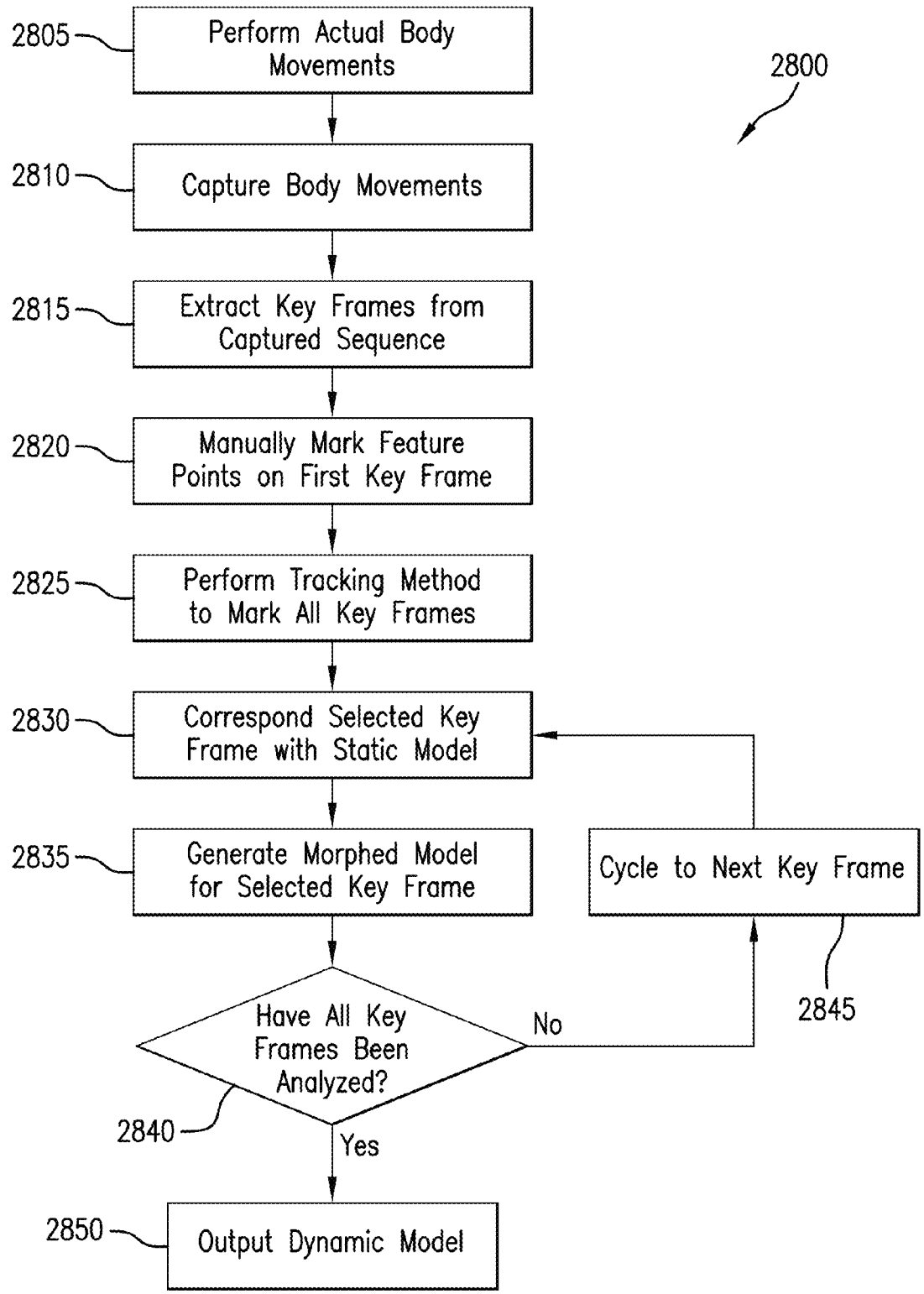
FIG. 28A depicts a flowchart of an exemplary dynamic modeling module using actual body movement.

FIG. 28A depicts a flowchart of an exemplary dynamic modeling module using actual body movement. A dynamic modeling module 2800 uses actual body movement to generate a dynamic model as described with reference to FIG. 26. In an exemplary embodiment, the dynamic model may be generated in 3D form. In the depicted example, a user performs actual body movement as in step 2805 and an image capture device captures the body movement as in step 2810. In some exemplary embodiments, the body movement performed may correlate with body movement commonly performed while wearing associated PPE. For example, the user may speak a variety of phrases when fitting a user with a respirator since it may be common for a user to speak or move their mouth while wearing the respirator.

Once a series of movements are captured, such as for example by video or a plurality of images, a key frame may be extracted from the captured sequence as in step 2815. The key frame may be an image reflecting a particular user movement, for example. In an exemplary embodiment, the key frame may simply be a generic reference or starting image. In an exemplary embodiment, the user may then manually mark feature points on the selected, first key frame as in step 2820. The feature points may correspond with distinguishable features on the body part captured. For example, a nose or mouth may be feature points for a captured facial area. In some exemplary embodiments, the user manually selects the feature points by visually selecting the feature points on a computer display. In some exemplary embodiments, the user manually selects the feature points by selecting body coordinates predetermined to be associated with the respective feature point. In some exemplary embodiments, the selection of the feature points may be automated via an image recognition software or device. In some exemplary embodiments, the feature points may be appointed identifying information, such as for example semantic information.

Once the feature points of the first key frame are identified and selected, a tracking method may be performed to identify and mark feature points on all key frames based on the selected feature points of the first key frame as in step 2825. In an exemplary embodiment, the tracking method may track the feature points via proximity of similar vertices in neighboring key frames. In some exemplary embodiments, the tracking method may be automatically performed by the dynamic module 2800.

One of the key frames having feature points may then be selected and the feature points corresponded to a static 3D model as in step 2830. In an exemplary embodiment, the static 3D model may be generated according to the detailed process exemplified in FIG. 27. The feature points may be linked to similarly located points from the point cloud of the static model such that properties of the points from the point cloud of the static model may be transferred to the feature points of the key frame, for example.

In an exemplary embodiment, a morphed model may then be generated by morphing the static model to a facial position of the key frame. For example, the point cloud of the static model may be altered to a proximal location of the feature points. If the key frame illustrates a user having an open mouth, the static model and associated point cloud may be altered to reflect an open mouth morphed static model. In an exemplary embodiment, the morphable model may be generated by performing rigid and/or non-rigid registration methods with vertices or points between the key frame and the static model.

In step 2840, the module 2800 determines whether there are additional key frames to analyze. If there are more key frames to analyze, then the module cycles to the next key frame as in step 2845 and returns to step 2830. If there are no more key frames to analyze, then a dynamic model may be outputted as in step 2850. In an exemplary embodiment, the dynamic model may be outputted to a comparator module for comparing the PPE model with the dynamic model to determine whether the PPE model fits the dynamic model. In an exemplary embodiment, the dynamic model may be outputted as a 3D model set for all captured key frames.

Figure 28B:
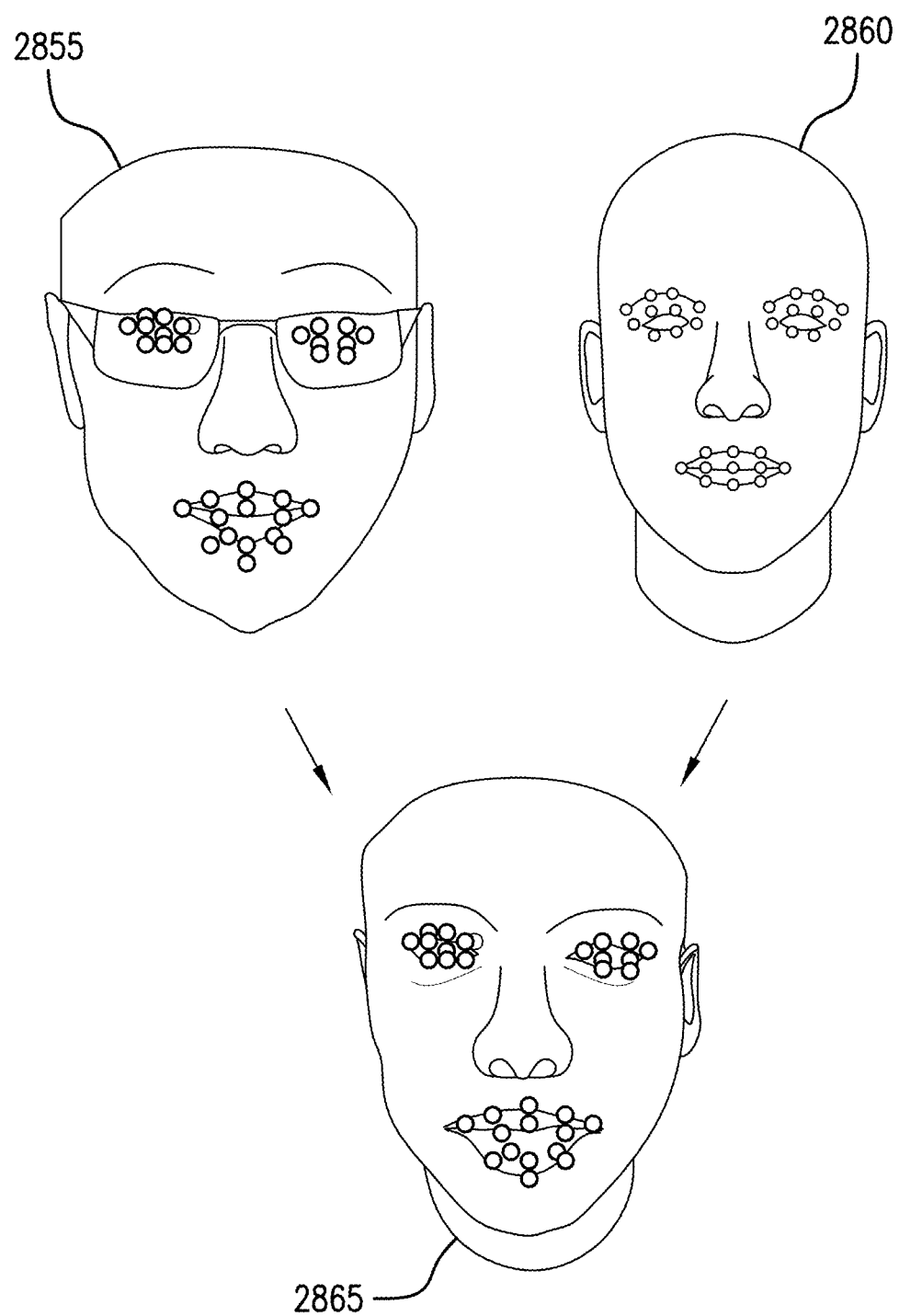
FIG. 28B depicts an exemplary graphical view of the dynamic modeling module of FIG. 28A.

FIG. 28B depicts an exemplary graphical view of the dynamic modeling module of FIG. 28A. As illustrated, a key frame 2855 having feature points manually marked on the key frame as described with reference to step 2820 of FIG. 28A. The static model 2860 may be generated by the static modeling module as described with reference to FIG. 27. As exemplified the point cloud of the static model may be located along similar facial features as the feature points of the key frame. A morphable model 2865 may be generated by combining the key frame and the static model as described with reference to step 2835 of FIG. 28A.

Figure 29A:
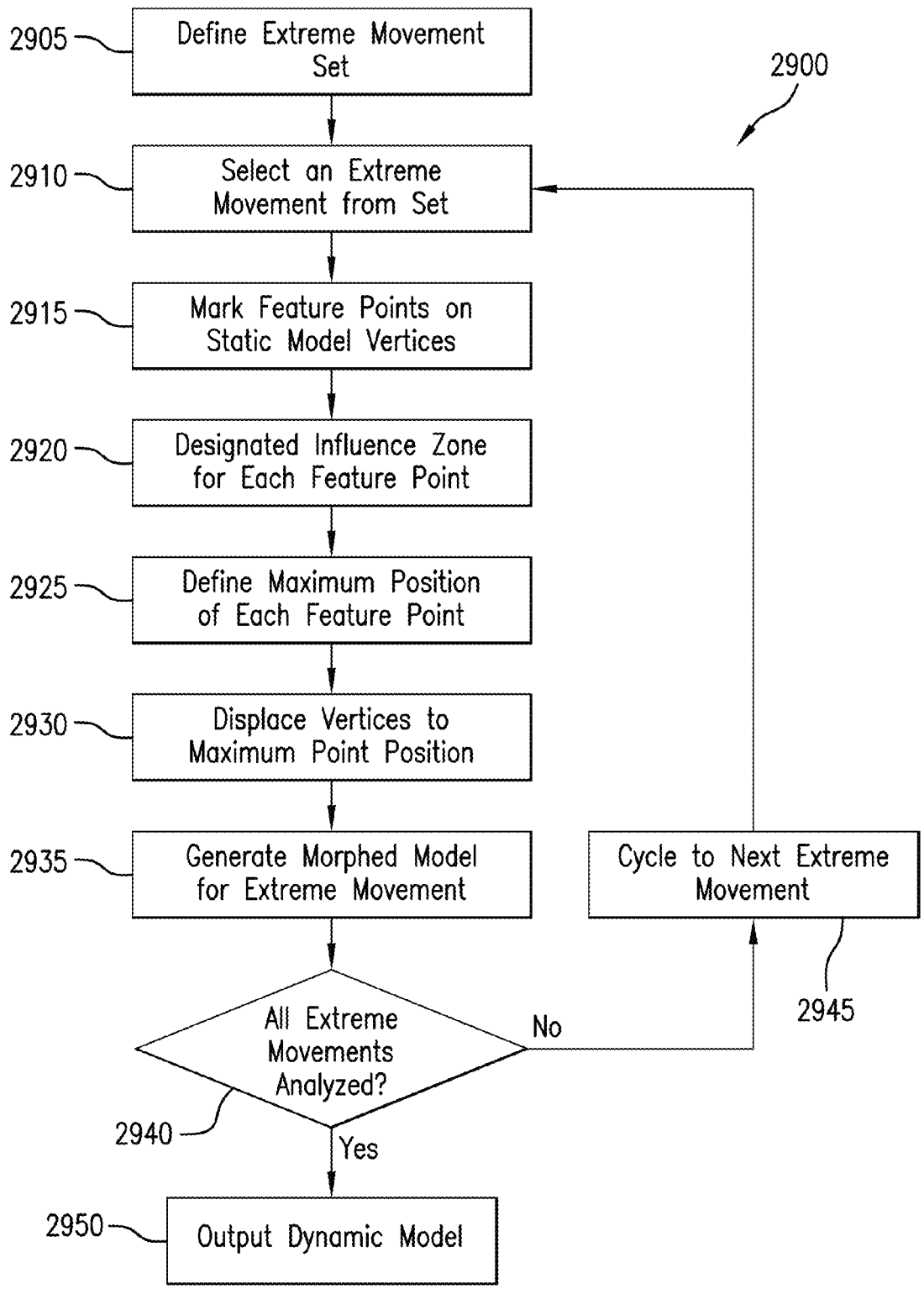
FIG. 29A depicts a flowchart of an exemplary dynamic modeling module using simulated body movement.

FIG. 29A depicts a flowchart of an exemplary dynamic modeling module using simulated body movement. A dynamic modeling module 2900 uses simulated body movement to generate a dynamic model as described with reference to FIG. 26. In an exemplary embodiment, the dynamic model may be generated in 3D form. In an exemplary embodiment, an extreme movement set is defined as in step 2905. The extreme movement set may be defined by a user in an exemplary embodiment. In other exemplary embodiments, the extreme movement set may be defined by the PPE manufacturer, regulatory agency, and/or employer. In an exemplary embodiment of a respirator, extreme movements may include raising the head, bowing the head, speaking, and/or opening the mouth. In an exemplary embodiment, the extreme movement set may be defined according to actions a user may typically undergo while wearing the respective PPE.

Once the extreme movement set is defined, a first extreme movement may be selected from the set as in step 2910. Feature points affected by the selected extreme movement are marked or identified on a static model. For example, if the extreme movement selected mimics an open mouth, feature points surrounding a mouth of the static model may be marked or identified. In an exemplary embodiment, the feature points are linked to corresponding proximal vertices. The static model may be generated by a process as exemplified with reference to FIG. 27, for example.

An influence zone of each feature point may also be defined on the static model as illustrated by step 2920. In an exemplary embodiment, the influence zone may be a proximal area of each feature point that may be affected by movement of the respective vertex. In an exemplary embodiment, the feature points and/or feature point influence area may correspond to predetermined data points of an MPEG 4 standard. In an exemplary embodiment, the feature points may include semantic information.

In some exemplary embodiments, the user manually selects the feature points by selecting body coordinates predetermined to be associated with the respective feature point. In some exemplary embodiments, the selection of the feature points may be automated via an image recognition software or device. In some exemplary embodiments, the feature points may be appointed identifying information, such as for example semantic information.

The maximum feature point position is also defined as in step 2925. The maximum feature point may correspond to a maximum distance and x, y, z coordinate location of the feature point away from a normal or current location of the feature point on the static model. The vertices and linked feature points are then displaced to the maximum position as defined by the extreme movement as in step 2930 and a morphed model is formed as in step 2935. Under a prior defined deformation function affect, neighbor related points on static model are displaced to a new position. In an exemplary embodiment, the displacement position of neighbor points can be calculated by:

$$D_{vertex} = D_{FP} * H(vertex, FP)$$

where $D_{vertex}$ may be the displacement position of neighbors, $D_{FP}$ is displacement of feature points, H is the deformation function. The influence zone of each feature point may also be blended or altered according to linked feature point movement. In an exemplary embodiment, if a vertex is affected by more than one feature point, neighboring vertices may be blended by a weighted sum.

A deformation function may be defined as:

$$H(f) = \begin{cases} T & |f| \leq \frac{1-\beta}{2T} \\ \frac{T}{2}\left[1 + \cos\left(\frac{\pi T}{\beta}\left[|f| - \frac{1-\beta}{2T}\right]\right)\right], & \frac{1-\beta}{2T} < |f| \leq \frac{1+\beta}{2T} \\ 0 & \text{otherwise} \end{cases}$$

where T is the radius of the area that applies the deformation, and β with the scope of (0, 1) is a parameter to adjust the deformation degree; if β is close to 1, the deformation will be smooth, and if β is close to 0, the deformation will be sharp.

In step 2940, the module 2900 determines whether there are additional key frames to analyze. If there are more extreme movements to analyze, the module cycles to the next extreme movement as in step 2945 and returns to step 2910. If there are no more extreme movements to analyze, a dynamic model may be outputted as in step 2950. In an exemplary embodiment, the dynamic model may be outputted to a comparator module for comparing the PPE model with the dynamic model to determine whether the PPE model fits the dynamic model. In an exemplary embodiment, the dynamic model may be outputted as a 3D model set for all captured key frames.

Figure 29B:
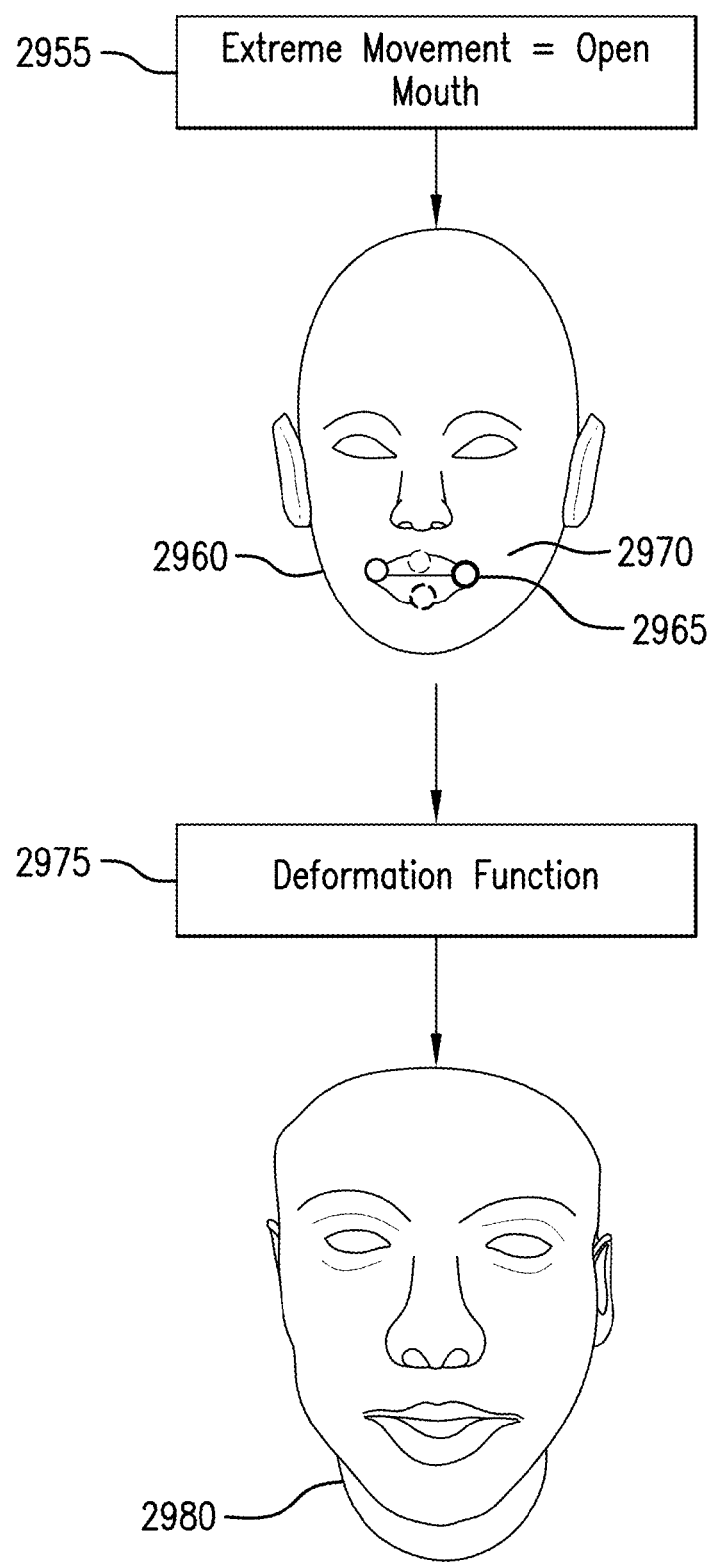
FIG. 29B depicts a graphical view of the exemplary dynamic modeling module of FIG. 29A.

FIG. 29B depicts a graphical view of the exemplary dynamic modeling module of FIG. 29A. The exemplary process includes a first defined extreme movement 2955, such as for example an open mouth. A static model 2960 may be imported, such as for example the static model generated by the static model module with reference to FIG. 27. The feature points 2965 and influence zones 2970 corresponding to the extreme movement 2955 are marked on the static model 2960. In an exemplary embodiment, the feature points may be located by correspondence with an MPEG 4 standard. A deformation function 2975 may be executed to morph the static model by displacing the feature points and influence zone according to the maximum position as defined by the extreme movement. Then, a morphed dynamic model 2980 is outputted. The dynamic model may be generated in 3D form. In an exemplary embodiment, the dynamic model has a body position correlating to the defined extreme movement.

Figure 30:
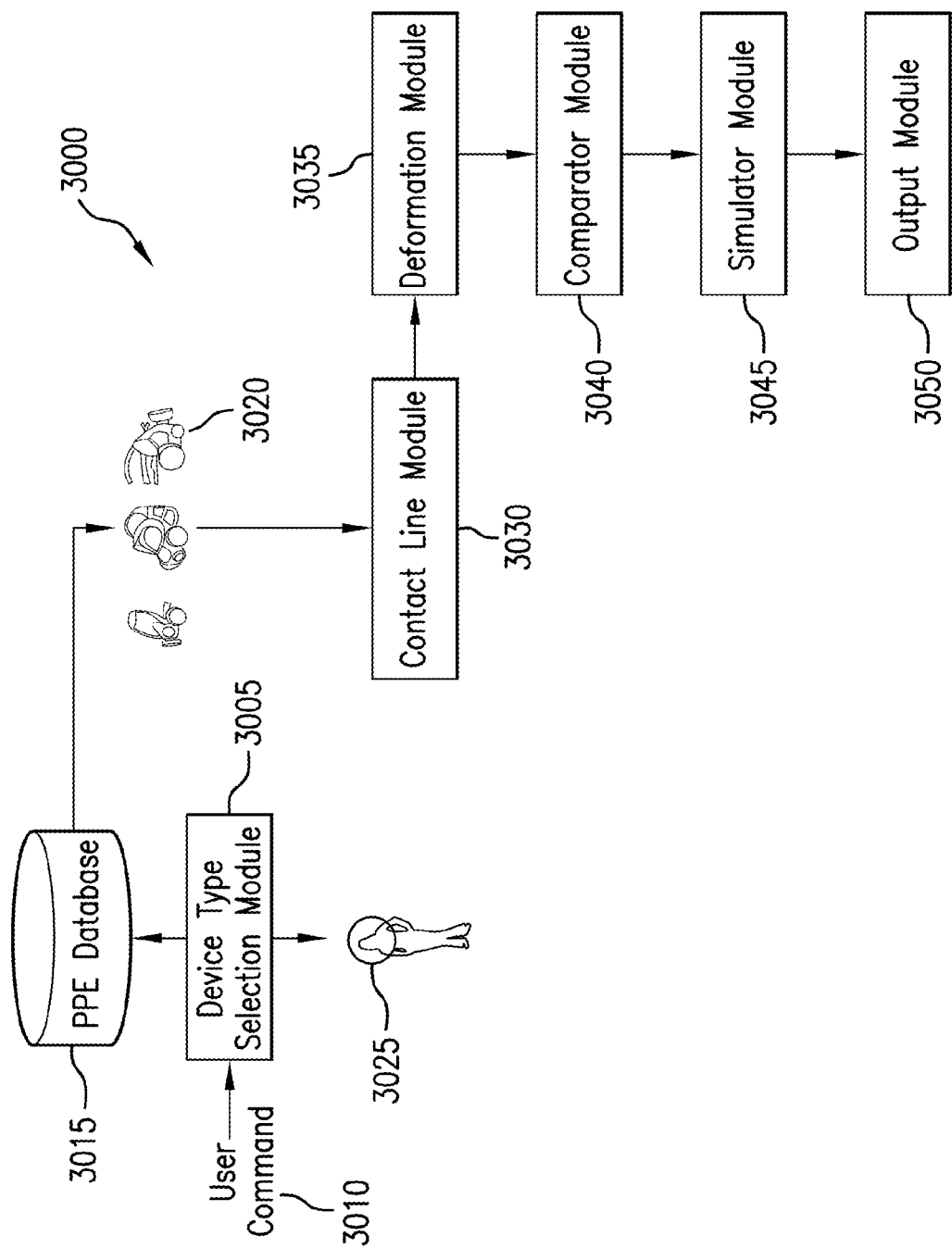
FIG. 30 depicts an overview of another exemplary PPE selection system.

FIG. 30 depicts an overview of another exemplary PPE selection system. A PPE selection system 3000 may be used to select an optimal fit PPE for a user body part based on an internal space measured between the PPE and the body part. In an exemplary embodiment, the internal space may be measured during a deformed state of the PPE. The PPE selection system 3000 includes a device type selection module 3005 for receiving a command from a user 3010. In the depicted example, the device type selection module 3005 sends commands to a PPE database 3015. The PPE database 3015 may include a variety of types of PPE 3020, such as for example gloves, respirators, and helmets. In an exemplary embodiment, the device type selection module 3010 may relay a command 3010 indicative of a particular type of PPE 3020, such as for example a facial respirator. In an exemplary embodiment, the command 3010 may be indicative of a particular user body part 3025 to be matched with the PPE 3020 from the PPE database 3015.

In some exemplary embodiments, the device type selection module 3005 may direct an image capture device (not shown) to capture a 2D or 3D image of the selected body part 3025. In some embodiments, the PPE 3020 may be modeled in a corresponding 3D shape. In some exemplary embodiments, one or more device range rules may define a capture range of the body part 3025 for the corresponding PPE 3020. For example, with half-mask respirators, the device range rules may define a capture range as the user face. In an exemplary embodiment of multiple PPE candidates 3020, a capture range computing step may calculate a maximum facial area range that may accommodate the PPE 3020 and then correlate the range with each PPE 3020 to determine whether the respective PPE 3020 fits within the facial area range.

Once the user body part 3025 is captured or retrieved, such as for example from a database, the user body part 3025 may be modeled using a contact line module 3030. The contact line module 3030 determines a contact line of the edge of the PPE 3020 on the body part 3025 of the user. For example, a respirator sealing edge may be defined as the contact line since the sealing edge may be the primary portion of the respirator that makes contact with the user facial area. The contact line may be determined by capturing an image of the user wearing the PPE 3020 and not wearing the PPE 3020, and then using a subtractive function to find the contact line. In an exemplary embodiment, the contact line may be found by capturing a 2D or 3D image of the user wearing and not wearing the PPE 3020. In another exemplary embodiment, the contact line may be determined using previously captured models of users and/or PPE 3020. For example, the previously captured models may be aligned using a rigid or non-rigid registration method to calculate a contact line. Once the contact line is found or calculated, the portion of the body part 3025 confined by the contact line may be determined. For example, a portion of a face confined and within the contact line of a respirator may include a portion of a nose and a mouth.

A deformation module 3035 may then be used to deform the PPE 3020. The PPE 3020 may be deformed according to a set of predetermined rules. For example, if a respirator is known to partially collapse inwards a certain percentage during wear, the PPE 3020 model may be deformed an amount or distance equivalent to a calculated standard collapse of an in-use respirator. In another exemplary embodiment, the degree of deformation may be determined by a maximum flex permissible by the construction of the PPE 3020. In an exemplary embodiment, a deformation of an inside surface or part of the PPE 3020 may be determined or calculated from a deformation of an outside surface or part of the PPE 3020. In another exemplary embodiment, a deformation of an outside part of the PPE 3020 may be computed by comparing the outside part of the PPE 3020 to a deformation of the inside part of the PPE 3020.

A comparator module 3055 may determine a fit level of the deformed PPE 3020 model 3020 with respect to the portion of the body part 3025 internal or confined by the contact line. In comparison, an internal measurement may be made between the internal surface of the PPE 3020 and the portion of the body part 3025 confined or internal to the contact line. For example, a distance between an inside surface of a respirator and a portion of a user face perpendicular to the inside surface may be calculated while the respirator is in the deformed state. In an exemplary embodiment, the internal measurement may be a distance between the PPE 3020 and the body part 3025. In another exemplary embodiment, the internal measurement may be an internal volume confined between the inside of the PPE 3020 and the corresponding body part 3025. In some exemplary embodiments, the internal measurement may be compared against a predetermined threshold to determine whether the PPE 3020 meets predetermined fit criteria. For example, if the predetermined threshold is not large enough, the PPE 3020 may be disqualified from an acceptable fit category of PPE 3020. The calculated results of the comparator module 3040 may be summarized for output and visualization.

In an exemplary embodiment, the internal measurement may use an implicit function to calculate a distance between the inside part of the PPE 3020 and the corresponding body part 3025. A Gaussian smooth function may then be applied to the distance calculation, for example. In some exemplary embodiments, a color-coded result of the internal measurement may be outputted to a user.

In an exemplary embodiment, the comparator module 3040 may fit the PPE 3020 model candidate 3020 to the user body part 3025 set according to mapping rules. According to a set of predetermined evaluation rules, a fit score of each PPE 3020 model 3020 may be provided relative the user body part 3025. Lastly, the comparator module 3040 may output an optimal fit PPE 3020 based on simulated comfort and fit. In an exemplary embodiment, a respective fit of the PPE 3020 may be visualized by color coding for user.

In an exemplary embodiment, the result from the comparator module 3040 may be outputted to a simulator module 3045 for display to a user through an output module. In an exemplary embodiment, the simulator module may graphically overlay the 3D PPE 3020 model 3020 upon a 3D representation of the user body part 3025 to illustrate to the user the PPE 3020 model 3020 being virtually worn on the user body part 3025. In some exemplary embodiments, a fit level, score, or color may accompany the graphical illustration for ease in interpreting the results.

In an exemplary embodiment, the output module 3050 may comprise a display module. In some exemplary embodiments, the output module 3050 may comprise a printed report. In some exemplary embodiments, the report may provide 3D visual representations of the PPE 3020 device virtually worn by the user. In some exemplary embodiments, the report may provide a detailed list of a fit level or score of each evaluated PPE 3020 device with respect to a region of interest of the user. In some exemplary embodiments, the report may provide a color-coded graphical representation of a PPE 3020 device virtual fit on the user. In some exemplary embodiments the color-coded graphical representation may illustrate, through color-coding, different levels of pressure as applied to the user by the PPE 3020 device when virtually worn.

Figure 31:
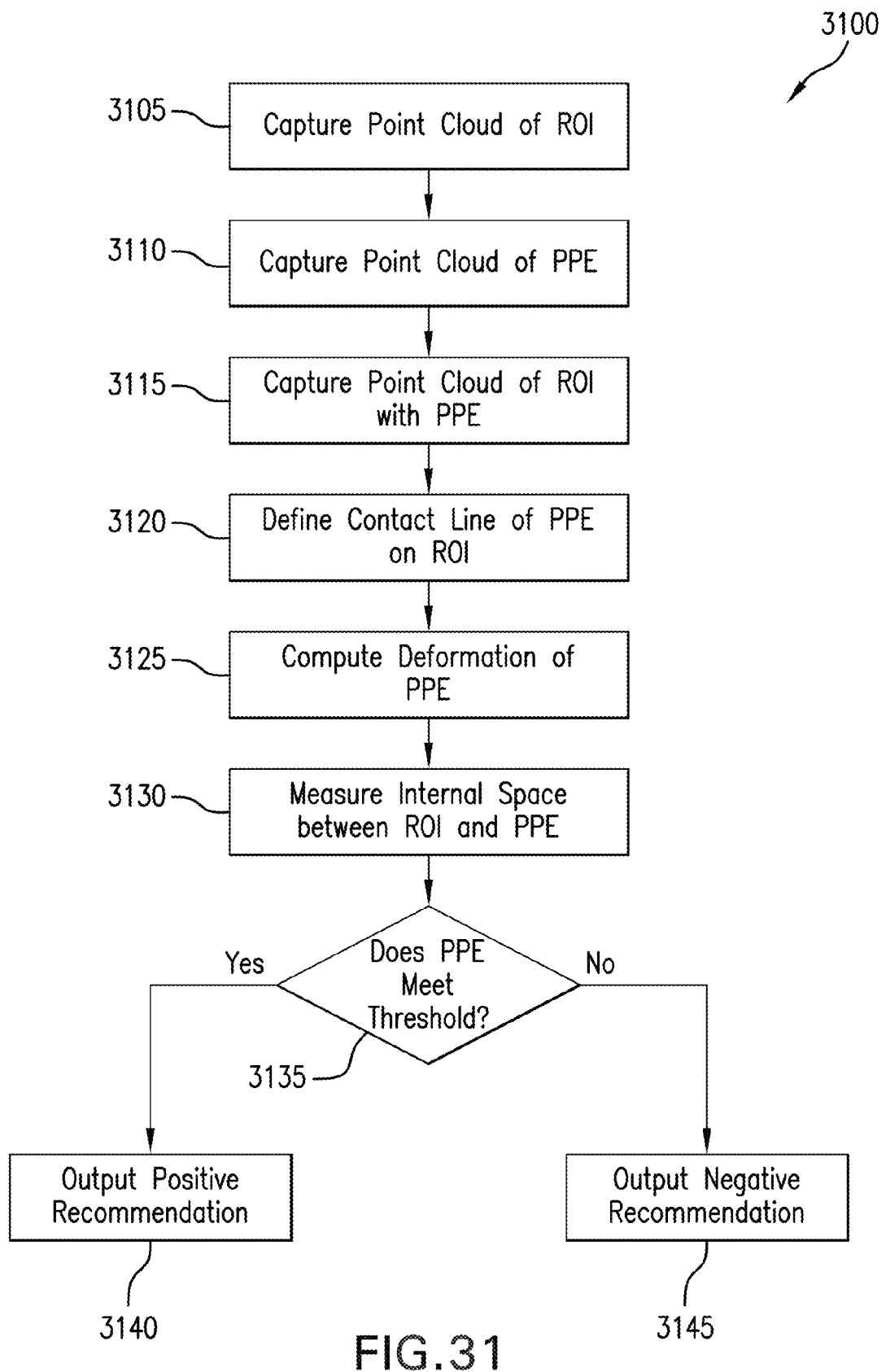
FIG. 31 depicts a flowchart of an exemplary PPE selection system.

FIG. 31 depicts a flowchart of another exemplary PPE selection system. In the exemplary system 3100, an optimal fit PPE for a user body part based on an internal space measured between the PPE and the body part. The system provides a method of measuring an internal or hidden space between a PPE and an associated body part to generate an objective fit of the PPE on the body part. For example, a point cloud of an outside part of a PPE may be captured during a deformed and non deformed state to determine a position or shape of an inside part of a PPE. In the depicted example, a point cloud may be captured of a region of interest (ROI) of a body part of the user as in step 3105. For example, a point cloud may be captured of a facial area of the user. A point cloud may be captured of a PPE as in step 3110, such as for example a respirator. In an exemplary embodiment, a point cloud may be captured both of the outside part (e.g., outside surface) and the inside part (e.g., inside surface) of the PPE. A point cloud may also be captured of the ROI with the PPE being worn as in step 3115.

In an exemplary embodiment, the point cloud data may include x, y, z coordinates which may be assembled to form a 3D image of the intended PPE and/or user body part. In an exemplary embodiment, a point cloud may include semantic information or other identifying feature points of the user body part and/or PPE. In some exemplary embodiments, an image capture device may directly capture a 2D or 3D image of the selected body part ROI and/or PPE. In some exemplary embodiments, previously captured 2D or 3D images of body part ROI and/or PPE may be used. In an exemplary embodiment, when there is not a 3D PPE model, captured point cloud of people with and without device may be retrieved independently and compared to get placement information for the outside part of PPE. An estimate of placement and fit of the inside part of PPE may be made, for example.

A contact line may also be defined as in step 3120. The contact line may be the point or edge that the PPE makes contact with the user ROI, such as for example a sealing edge of a respirator on a face of a user. Once the contact line is determined a portion of the ROI that is confined or within the contact line may be determined as will be described.

A deformation of the PPE may also be calculated, measured, or determined as in step 3125. For example, a deformation of an inside or outside part of the PPE may be calculated or measured based on a deformation of a respective outside or inside part of the PPE. In an exemplary embodiment, a degree of deformation may be predetermined by a manufacturer. In another exemplary embodiment, a degree of deformation may be determined by an employer based on common workplace practices. In an exemplary embodiment, the inside or outside part of the PPE may be used to generate the deformed PPE structure, thus only one of the inside or the outside part of the PPE may be needed.

The internal space between the PPE and the portion of the ROI confined by the contact line may then be measured as in step 3130. In an exemplary embodiment, the internal space may be determined based on a perpendicular distance between the PPE and the ROI. In another exemplary embodiment, the internal space may be determined by a contained volume between the PPE and the ROI. In an exemplary embodiment, the internal space may be measured while the PPE is in a deformed state.

A comparator module may determine whether a threshold has been met by the measured internal space as in step 3135. If a predetermined threshold has been met, then a positive recommendation may be outputted to a user as in step 3140. In an exemplary embodiment, a 3D visual representation of the PPE on the ROI may be displayed to the user. In another exemplary embodiment, the internal measurement may be displayed on the 3D visual representation. If a predetermined threshold has not been met, then a negative recommendation may be outputted to a user as in step 3145. For example, if the distance between an internal surface of a respirator and the beneath facial area does not meet a predetermined length, then the respirator may fail a fit test.

Figure 32A:
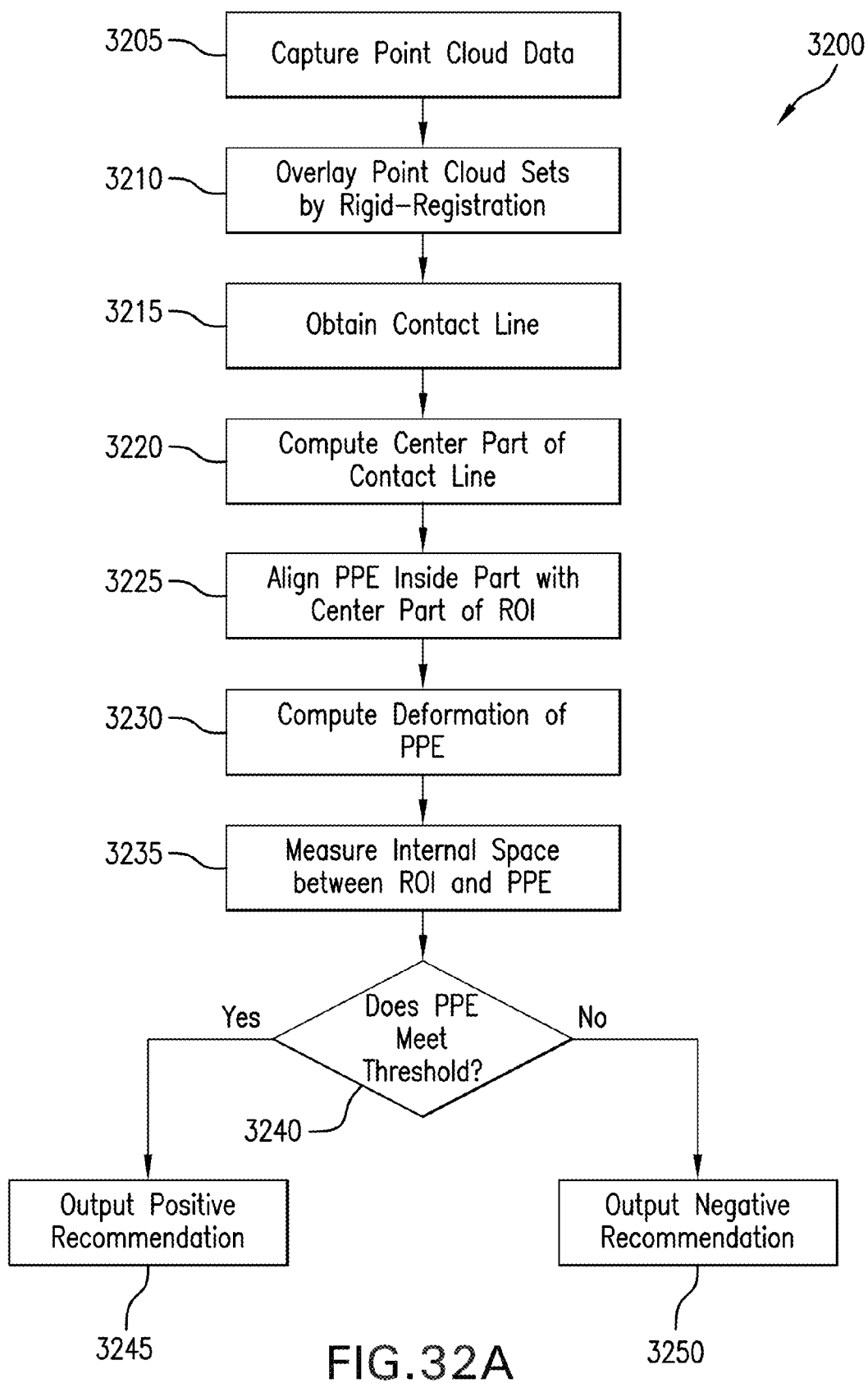
FIG. 32A depicts a flowchart of another exemplary PPE selection system.

FIG. 32A depicts a flowchart of another exemplary PPE selection system. In the exemplary system 3200, an optimal fit PPE for a user body part based on an internal space measured between the PPE and the body part. In the depicted example, the system 3200 may compute a fit of the PPE on the user body part based on previously captured point clouds of the PPE and/or body part. In an exemplary embodiment, point cloud data may be captured of the body part ROI (e.g., face) and the PPE (e.g., respirator) as in step 3205. In some exemplary embodiments, point cloud data may be captured of the ROI with the PPE being worn.

If the PPE is not presently available, previously captured and stored point cloud data may be used to determine placement of the PPE on the ROI. For example, point cloud data of the PPE may be overlaid upon point cloud data of the ROI as in step 3210. In an exemplary embodiment, the point cloud data may be aligned using a rigid-registration method. In an exemplary embodiment, the rigid-registration method aligns feature points of the PPE and ROI. In another exemplary embodiment, the rigid-registration method aligns semantic information of the PPE and ROI. In another exemplary embodiment, the rigid-registration method aligns corresponding vertices of the PPE and ROI.

In an exemplary embodiment, once the PPE is placed on the ROI, a contact line of the PPE on the ROI may be obtained as in step 3215. The contact line may be the point or edge that the PPE makes contact with the user ROI, such as for example a sealing edge of a respirator on a face of a user.

In an exemplary embodiment, the contact line may be visibly or computationally defined and such that a center part of the contact line may be determined. For example, the center part of the contact line may be the center of a medial axis of the contact line. In an exemplary embodiment, the medial axis may be vertically oriented and separate left and right sides of the space confined by the contact line. A center part of an inside part of the PPE may also be computationally determined and the center part of the PPE and the center part of the ROI are aligned. In an exemplary embodiment, rigid-registration methods may be used to obtain placement of the PPE on the ROI by aligning the center parts of the PPE and the ROI. Once the center parts of the ROI and PPE are aligned, corresponding points of the ROI and PPE may be determined and confirmed such as for making internal measurements.

A deformation of the PPE may be calculated, measured, or determined as in step 3230. For example, a deformation of an inside or outside part of the PPE may be calculated or measured based on a deformation of a respective outside or inside part of the PPE. In an exemplary embodiment, a degree of deformation may be predetermined by a manufacturer. In another exemplary embodiment, a degree of deformation may be determined by an employer based on common workplace practices. In an exemplary embodiment, the inside or outside part of the PPE may be used to generate the deformed PPE structure, thus only one of the inside or the outside part of the PPE may be needed.

The internal space between the PPE and the portion of the ROI confined by the contact line may then be measured as in step 3235. In an exemplary embodiment, the internal space may be determined based on a perpendicular distance between the PPE and the ROI. In another exemplary embodiment, the internal space may be determined by a contained volume between the PPE and the ROI. In an exemplary embodiment, the internal space may be measured while the PPE is in a deformed state.

A comparator module may determine whether a threshold has been met by the measured internal space as in step 3240. If a predetermined threshold has been met, then a positive recommendation may be outputted to a user as in step 3245. In an exemplary embodiment, a 3D visual representation of the PPE on the ROI may be displayed to the user. In another exemplary embodiment, the internal measurement may be displayed on the 3D visual representation. If a predetermined threshold has not been met, then a negative recommendation may be outputted to a user as in step 3250. For example, if the distance between an internal surface of a respirator and the beneath facial area does not meet a predetermined length, then the respirator may fail a fit test.

Figure 32B:
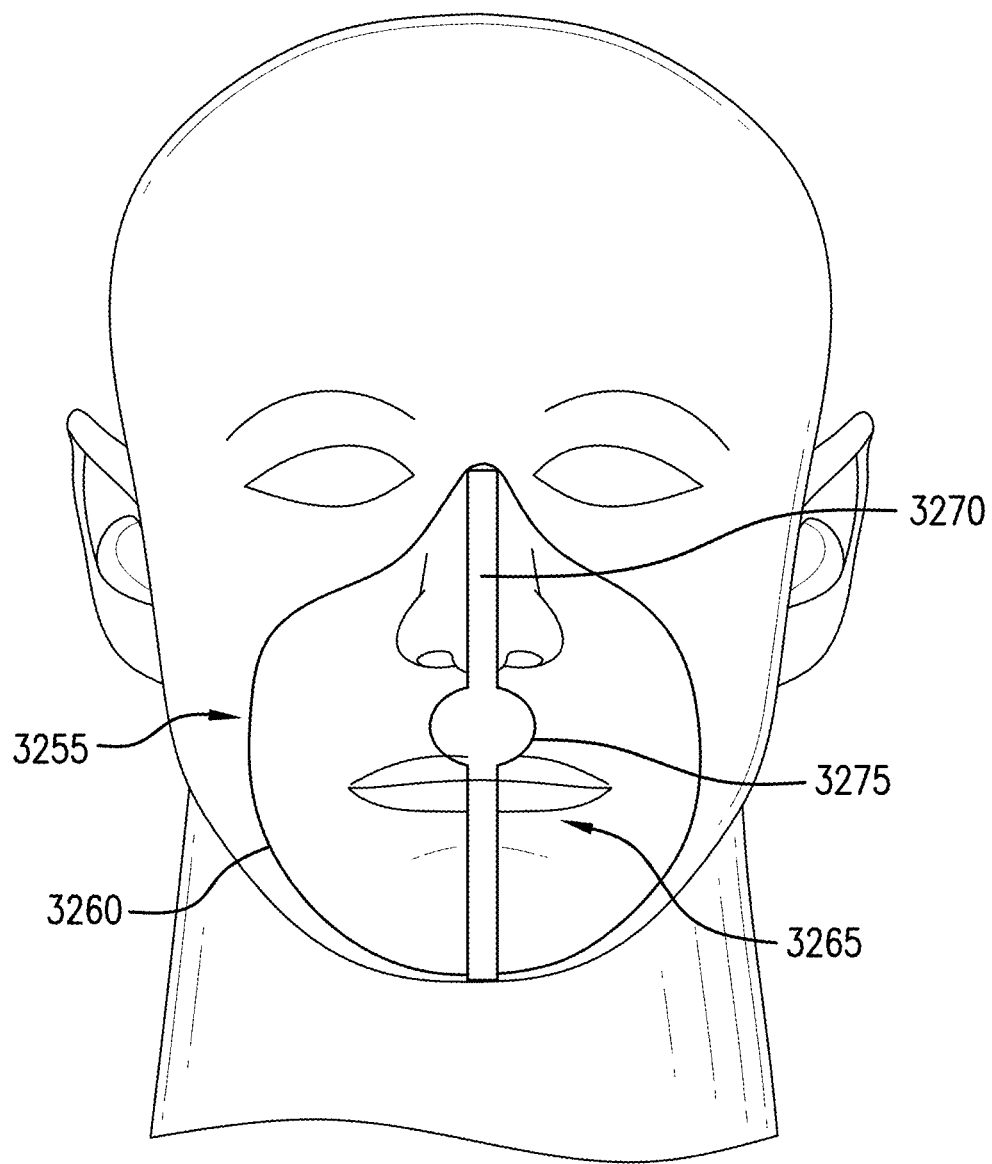
FIG. 32B depicts an exemplary center part on a ROI as defined with reference to FIG. 32A.

FIG. 32B depicts an exemplary center part on a ROI as defined with reference to FIG. 32A. A region of interest ROI 3255 may be a body part that is to be protected, such as by a corresponding PPE. In an exemplary embodiment, the ROI 3255 may be a facial area of a user. The ROI 3255 may be illustrated in a 3D form to a user. In an exemplary embodiment, the ROI 3255 includes point cloud data used in the construction of the 3D form and the fitting of the PPE.

In an exemplary embodiment, a contact line 3260 may be defined on the ROI 3255, as previously defined with reference to step 3215 of FIG. 32A. The contact line 3260 may be peripheral edge of the PPE that makes contact with the ROI 3255, such as for example a sealing edge of a respirator. In an exemplary embodiment, the contact line 3260 may be computationally determined by comparing a user ROI while wearing and while not wearing a PPE. In another exemplary embodiment, the contact line 3260 may be manually drawn on the ROI by tracing a peripheral edge of the PPE worn on the ROI.

A center part 3265 of the contact line 3260 may also be defined, as previously defined with reference to step 3220 of FIG. 32A. In an exemplary embodiment, the center part 3265 includes a medial axis 3270 and axis center 3275. The medial axis 3270 may separate two-halves of the area of the ROI 3255 defined by the contact line 3260. For example, the medial axis 3270 may separate left and right halves of the area of the ROI 3255 defined by the contact line 3260. In an exemplary embodiment, the axis center 3275 may be the lengthwise center of the medial axis 3270.

In an exemplary embodiment, a PPE center part including a PPE medial axis and PPE axis center are also defined on the PPE with reference to a contact edge (e.g., sealing edge of a respirator). The PPE medial axis and PPE axis center of the PPE are then aligned with the medial axis 3270 and axis center 3275 of the ROI to determine a placement of the PPE on the ROI, as previously defined with reference to step 3225 of FIG. 32A.

Figure 33:
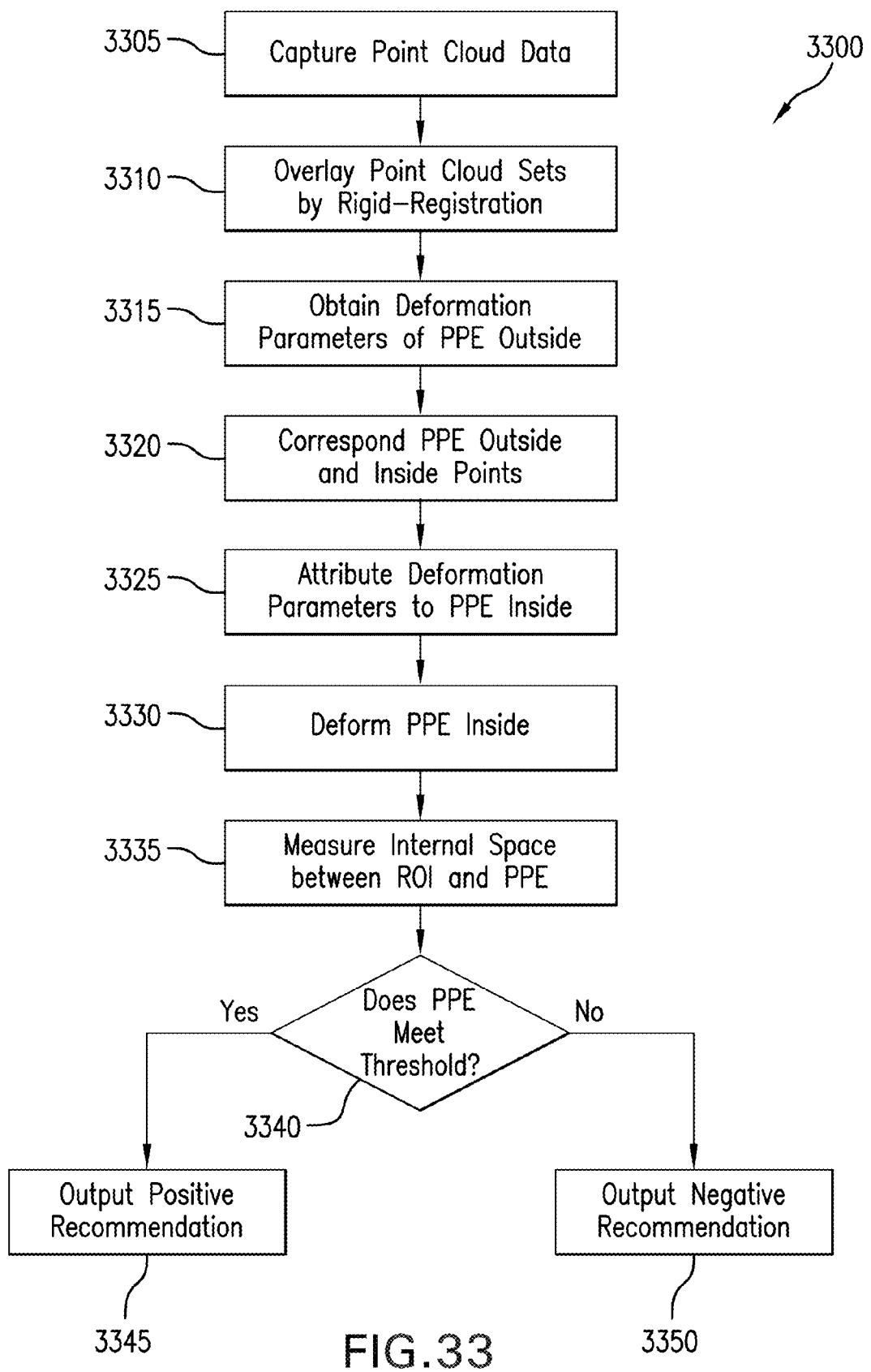
FIG. 33 depicts a flowchart of an exemplary deformation process.

FIG. 33 depicts a flowchart of an exemplary deformation process. A deformation module 3300 may determine a deformation of an inside part of PPE by correspondence with a deformation of an outside part of the PPE to obtain an internal measurement of the PPE and body part for determining whether the PPE fits the body part. The module 3300 first captures point cloud data of the body part and PPE as in step 3305. In some exemplary embodiments, the point cloud data may be captured earlier in the process and relayed to the deformation module 3300. The point cloud sets are overlaid upon each other as in step 3310 to fit the PPE to the body part. In some exemplary embodiments, the fitting process may be performed by other modules and the result relayed to the deformation module 3300.

The module 3300 may then obtain deformation parameters of the outside part of the PPE as in step 3315. In an exemplary embodiment, the outside part of the PPE may be an outside surface of the PPE with respect to the PPE being worn by a user. In an exemplary embodiment, the deformation parameters may be predetermined according to specific construction properties of the PPE. In another exemplary embodiment, the deformation parameters may be determined by functions, such as for example the deformation function described with reference to FIG. 29A.

The PPE outside part may then be corresponded to the PPE inside part as in step 3320. For example, corresponding inside and outside part points may be correlated based upon a nearest distance between inside points and outside mesh nodes. In another exemplary embodiment, inside points or vertices determined to be physically affected by specific outside points or vertices are linked. For example, moving a point A on an outside part may correspondingly move a point B on an inside part of the PPE, and thus point A may be linked to some degree to point B.

Once all necessary inside and outside part points of the PPE have been linked, the outside point deformation parameters previously defined in step 3315 are attributed to the respective inside points as in step 3325. The PPE inside part may then be computationally deformed as in step 3330. In an exemplary embodiment, the PPE inside part may be deformed according to the attributed deformation parameters linked to the respective inside part in step 3325.

The internal space between the inside part of the PPE and the portion of the ROI confined by the contact line may then be measured as in step 3335. In an exemplary embodiment, the internal space may be measured while the inside part of the PPE is in the deformed state. In an exemplary embodiment, the internal space may be determined based on a perpendicular distance between the PPE and the ROI. In another exemplary embodiment, the internal space may be determined by a contained volume between the PPE and the ROI.

A comparator module may determine whether a threshold has been met by the measured internal space as in step 3340. If a predetermined threshold has been met a positive recommendation may be outputted to a user as in step 3345. In an exemplary embodiment, a 3D visual representation of the PPE on the ROI may be displayed to the user. In another exemplary embodiment, the internal measurement may be displayed on the 3D visual representation. If a predetermined threshold has not been met, then a negative recommendation may be outputted to a user as in step 3350. For example, if the distance between an internal surface of a respirator and the beneath facial area does not meet a predetermined length, then the respirator may fail a fit test.

Figure 34:
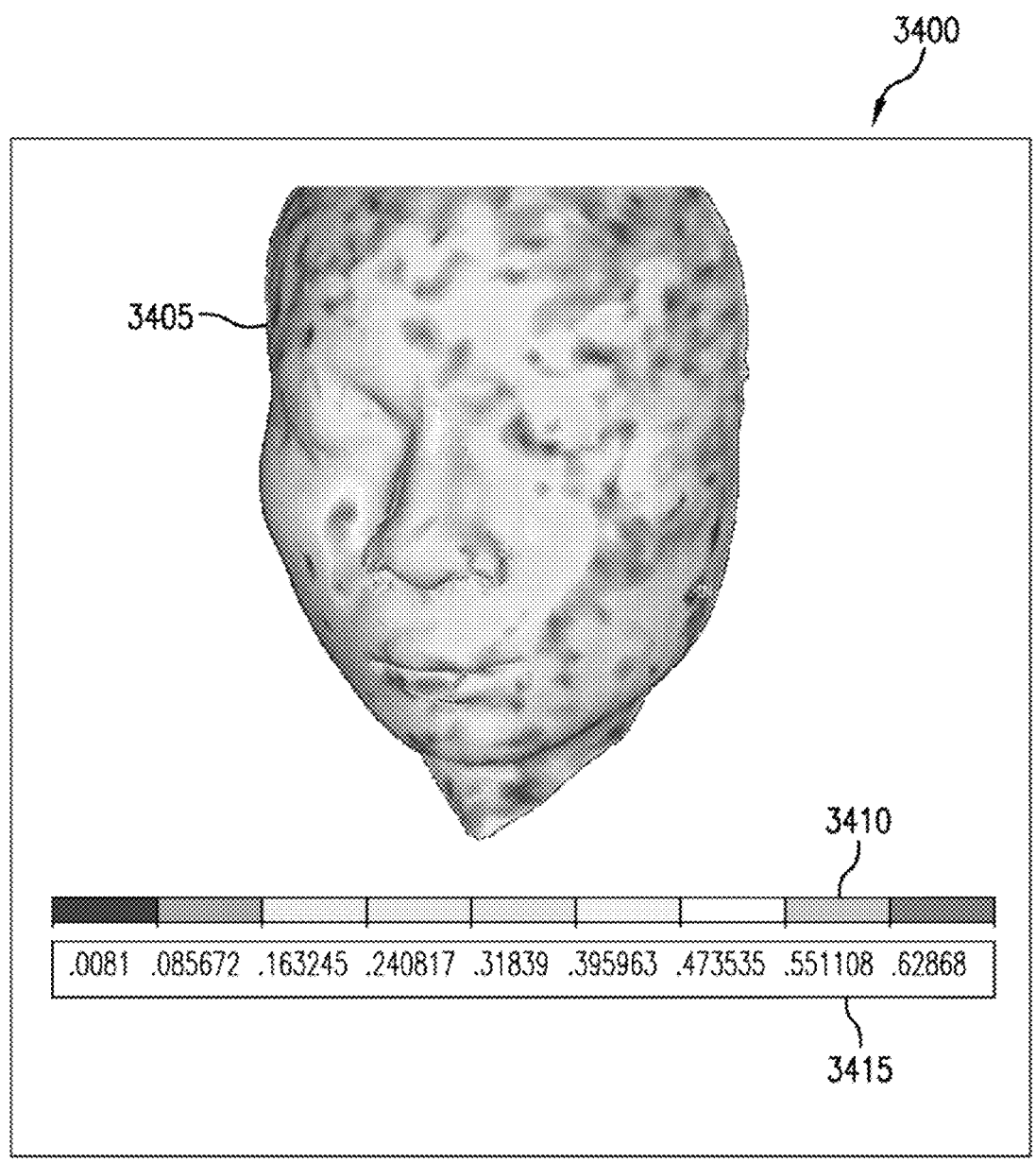
FIG. 34 depicts a graphical representation of an exemplary color-coded display of a PPE fit.

FIG. 34 depicts a graphical representation of an exemplary color-coded display of a PPE fit. A display 3400 may be outputted to a user by an output module for providing a visual recommendation of a PPE fit. In an exemplary embodiment, the display 3400 may be outputted on a computer screen. In another exemplary embodiment, the display 3400 may be outputted in a printable format.

The display 3400 includes a representation of the evaluated user body part 3405, for example a facial area. In an exemplary embodiment, the body part 3405 may be portrayed in 3D form. The body part 3405 may be colored according to pressure distribution as applied on the body part 3405 by the PPE. In an exemplary embodiment, the PPE may be shown with the body part 3405. In the depicted example, the display 3400 includes a reference chart 3410 of the colors illustrated on the body part 3405 and values 3415 associated with each of the colors on the color chart 3410. The values 3415 may represent ranges of pressure distribution, for example.

In an exemplary embodiment, a user may visually determine whether a PPE would provide an acceptable fit by visualizing whether any areas upon the body part 3405 are a certain color. For example, if an area of the body part 3405 were colored red, a high degree of applied pressure may be applied to the body part 3405 by the respective PPE. For example, a respirator may fit tightly against a face of a user in a certain area. In an exemplary embodiment, if a certain color were displayed on the body part 3405 which would represent a threshold being exceeded, the respective PPE may be disqualified from further consideration with respect to the specific user.

In another exemplary embodiment, shapes or symbols, rather than colors may be visually displayed on the body part 3405 to symbolize measured criteria. For example, a first shape may represent a first pressure applied to the body part 3405 by the PPE and a second color may represent a second pressure applied to the body part 3405 by the PPE. In another exemplary embodiment, a first color, shape, or pattern may be overlaid upon the body part 3405 to represent a first distance that the PPE is from the body part when virtually worn, and a second color, shape, or pattern may be overlaid upon the body part 3405 to represent a second distance that the PPE is from the body part when virtually worn.

Figure 35:
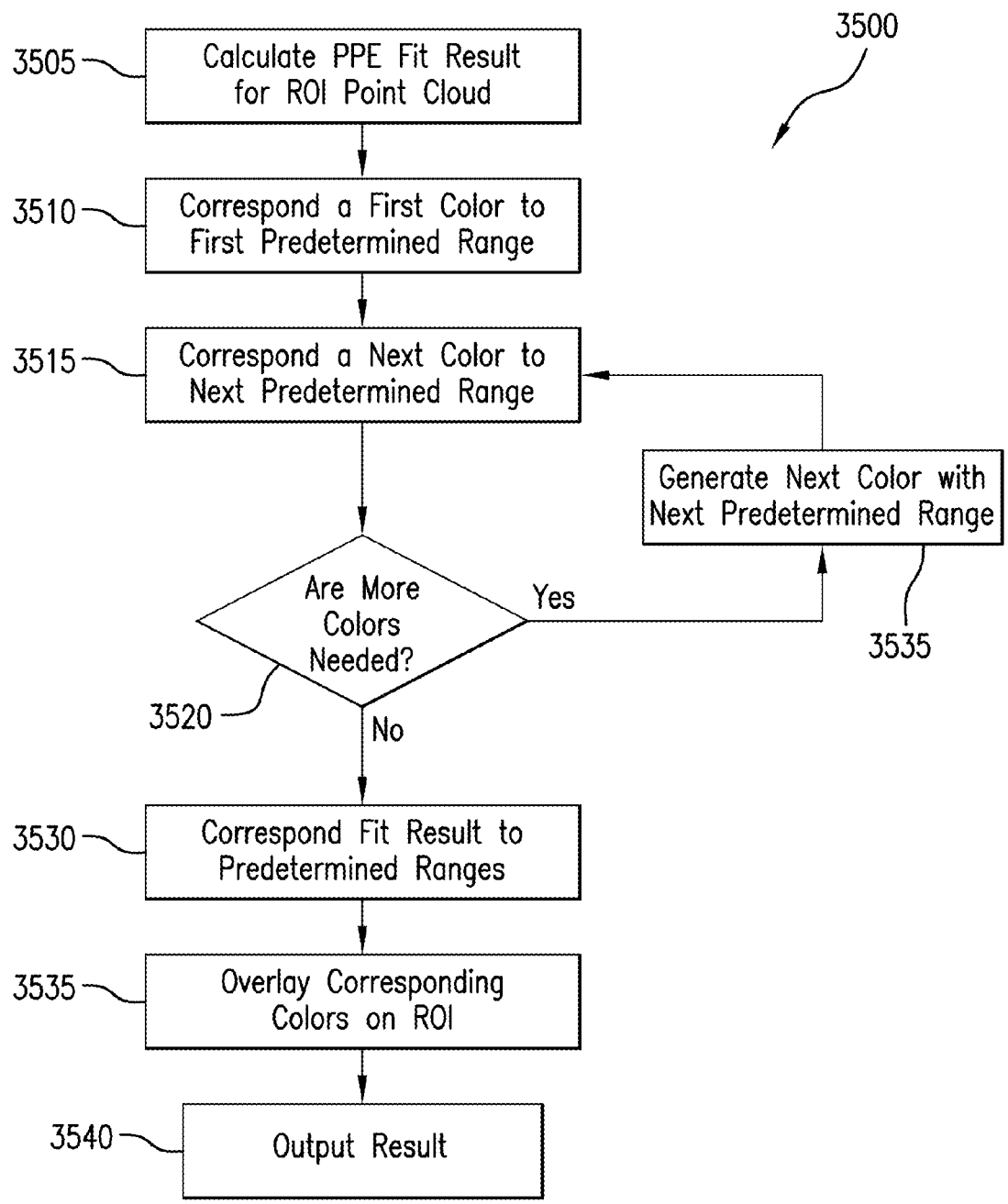
FIG. 35 depicts a flowchart of an exemplary color-coded result generator.

FIG. 35 depicts a flowchart of an exemplary color-coded result generator. A color-coded result generator 3500 may associated a set of fit results with one or more colors to provide a user with a quick method of determining whether a respective PPE would fit and/or be comfortable. The fit results may be calculated and assigned to each of the points on the point cloud, such that each point in the point cloud of the ROI may have an associated fit result as illustrated in step 3505. The result generator 3500 may calculate and assign the fit results or the fit results may be imported. In an exemplary embodiment, the fit results each include an applied pressure upon the body part by the PPE. For example, the fit results may include a pressure applied to a facial area by the respirator at each defined point or vertices.

The generator 3500 may correlate one or more colors to one or more predetermined ranges as in steps 3510 and 3515. For example, a first range of applied pressure values may be assigned a first color, for example a blue color. A second range of applied pressure values may be assigned a second color, for example a green color. The generator determines whether more colors are needed as in step 3520 and generates additional colors with assigned predetermined ranges as in step 3525. In another exemplary embodiment, a set of predetermined colors may be initially assigned that include all possible ranges, such as for example from $-\infty$ to $+\infty$.

The color ranges may then be corresponded to the fit results as in step 3530. For example, a green color overlay on the human body part may represent an optimal match and a red color overlay on the human body part may represent a non optimal match. In an exemplar embodiment, the colors may represent how tight or loose PPE may be relative the human body part, such as for example red being shown for an area of the body part where the PPE product fits too tightly and green may be shown for an area of the body part where the PPE product fits too loosely.

The colors may then be overlaid on a body part ROI representation as in step 3535 and the result may be outputted to the user as in step 3540. In an exemplary embodiment, the body part ROI representation may be in 3D form. An exemplary output is shown by display 3400 of FIG. 34.

Although various embodiments have been described with reference to the Figures, other embodiments are possible. For example, in some embodiments, the system and method for automatically selecting a respirator may comprise predictive software that may capture a facial image and match the facial image to the closest form of a respirator model, type, and/or size. In an exemplary embodiment, the software may use a dynamic set of images and match the images to the flexibility of a respirator shape to predict an interface between the respirator model and the facial model. For example, the software may predict whether the interface between the respirator and the facial area will result in separation thus permitting leakage or breach in the sealing surface.

In various embodiments, the image capture device may be a 3D digital scanner, such as for example one or more Kinect devices manufactured by Microsoft®. In some embodiments, the image capture device may be a still camera device. In some exemplary embodiments, the image capture device may be a video recorder device. In some exemplary embodiments, the image capture device may be a handheld unit. The image capture device may be wirelessly connected to a processing module for receiving a scanned image from the image capture device and determining whether a scanned or modeled PPE fits a scanned or modeled body part. In some exemplary embodiments, the image capture device may be a low-cost item.

In various embodiments, apparatus and methods may involve a digital image of a facial area of a user in a variety of facial positions. For example, a first facial position may be a grin or smile. A second facial position may be the user voicing specific letters and/or sounds. In an exemplary embodiment, software may digitize the facial shape of the user in each of the facial positions to create a flexible electronic file, for example. In an exemplary embodiment, software may also store files having contours of respirators in both a static state and in a flexed state for comparison to facial shape files. In an exemplary embodiment, the software may match up a negative cavity of the respirator model with a positive face form of the facial area model to determine a fit level of a respirator or best fit respirator. In some exemplary embodiments, software may match the respirator and the facial area in both static and dynamic positions of the facial area and/or respirator to determine whether a respirator will fit in a variety of facial positions and/or flexed positions of the respirator.

In an exemplary embodiment, an administrator may oversee a matching process of the respirator and a specific facial area. For example, an administrator at a workplace may oversee the matching process for each new employee. In some examples, each employee may undergo a matching process, such as for example via a pay per use web link. In some exemplary embodiments, a kiosk or vending machine may include software functionality to perform a matching process between one or more respirators and a specific facial shape. For example, a user may scan a user facial shape at a kiosk, and the kiosk may geometrically compare the facial shape of the user to a plurality of respirator models available for dispensing to find a respirator that most closely matches the facial shape of the user. Upon finding an optimal or best fit respirator, the kiosk may dispense the respective respirator or provide direction to the user on where the respirator may be available for pickup and/or purchase, for example.

In accordance with another embodiment, a population data gathering and storage system may be made available via scanning facial areas of users. In some examples, the facial shapes gathered and stored via the matching process may be used by respirator manufacturers to improve a respirator design such that newly manufactured respirators more closely match a common facial shape of persons commonly wearing the respirators. In some examples, the facial shapes gathered and stored via the matching process may be used by employers to provide insight on which respirators to stock in greater or less numbers. In some exemplary embodiments, a captured point cloud of a PPE and/or a user body part may be re-used in other PPE design.

In accordance with another embodiment, a variety of body parts may be scanned and captured for being matched with respective clothing or garments. For example, a hand of a user may be scanned and stored as a data set such that a variety of glove models, types, and/or sizes may be compared against the hand of the user to find an optimal or best fit glove. In another exemplary embodiment, a head of a user may be scanned and stored as a data set such that a variety of helmet models, types, and/or sizes may be compared against the head of the user to find an optimal or best fit helmet.

In accordance with an exemplary embodiment, a system and method for selecting a respirator may include a body modeling module for capturing an image(s) of a body part (e.g., facial area) of a user. In an exemplary embodiment, the image(s) may be used to generate a 3D model of the body part.

In some embodiments, the system and method for selecting a respirator may include one or more product databases of PPE 3D models. For example, each product database may include PPE to be worn on a specific body part. In an exemplary embodiment, a respirator database may be associated with facial areas, a glove database may be associated with hands, and a helmet database may be associated with heads. In some exemplary embodiments, the material properties of each specific PPE may also be stored with the specific PPE model.

In some embodiments, the system and method for selecting a respirator may include a rule library illustrating a method of mapping 3D PPE models to a 3D human body part. In an exemplary embodiment, a rule library may include three types of rules, such as for example association rules, mapping rules, and evaluation rules. For example, association rules may define which related PPE 3D models from the product database are associated to a target body part. For example, respiratory products from product database may be associated to face models, and footwear products from product databases may be associated to foot models. In an exemplary embodiment, mapping rules may define how the product model will be mounted to the body model, such as for example by mapping directions, forces, and/or deformations according to a material property. In an exemplary embodiment, evaluation rules may define how well the PPE fits the body part in accordance with a mapping result. For example, via dimensional comparison, a body dimension may be compared to a related product dimension range or pressure distribution during and after the product is mapped to the body part.

In some embodiments, the system and method for selecting a respirator may include a 3D geometry matching module. In an exemplary embodiment, the matching module may calculate all differences between the 3D PPE models and the 3D human body model. The geometry matching module may select a PPE part according to association rules, determine the difference with the mapping rules, summarize the difference according to the evaluation rules, and then propose a product model and/or size which may optimally fit a user. In an exemplary embodiment, a top three or top five best fitting products may be provided to the user.

In some embodiments, the system and method for selecting a respirator may include a simulator module. In an exemplary embodiment, a simulator module may visualize to a user how well the PPE model fits on the body part model. In some exemplary embodiments, the simulator may display the human body part and PPE product in 3D representations. In some exemplary embodiments, color coding may be used to illustrate how well the PPE fits a human body part. For example, a green color overlay on the human body part model may represent an optimal match and a red color overlay on the human body part model may represent a non optimal match. In some examples, the colors may represent how tight or loose the PPE may be relative the human body part, such as for example red being shown on an area of the body part model where the PPE fits too tightly and green shown on an area of the body part model where the PPE fits too loosely.

In accordance with an exemplary embodiment, the PPE selection system may output a comfort level based on a predetermined measurement scale, where the comfort level may reference a relative comfort of a PPE virtually worn by a user. In some embodiments, a comfort level may be determined by the amount of internal space measured between an inside part of a PPE and a corresponding body part. In some exemplary embodiments, a comfort level may be determined by a degree of permissible movement by a respective body part while a PPE is worn. For example, a comfort level may be determined for a respirator by determining whether the respirator maintains a seal with a facial area while the mouth of the user is being opened. In accordance with an exemplary embodiment, a user feeling may be determined by an objective comfort evaluation based on quantitative measurement. For example, a module may calculate a numeric pressure level upon the facial model as applied by the respirator model and compare the calculated pressure level with a set of predetermined pressure ranges each associated with a specific comfort level.

A PPE selection system may be used for predicting an optimal fitting PPE (e.g., respirator) for a specific user. The system may includes an offline phase and a selection phase. The offline phase may be performed during a fitting process of the PPE to the user in some exemplary embodiments. In other exemplary embodiments, the offline phase may be performed at some time prior to the fitting process of the PPE to the user.

In the offline phase, one or more types of PPE may be selected to be associated with semantic information as in step. In an exemplary embodiment, several PPE are analyzed and processed to build a database of PPE having semantic properties. In some examples, the PPE types may include a variety of sizes and models of face respirators (e.g., masks). A volunteer face model having semantic properties may then be correlated with the specific PPE such that the semantic properties of the face model are correlated with intersecting points or vertices of the specific PPE as depicted in step. To increase the accuracy of the locations of the semantic properties applied to the specific PPE model, the volunteer face model may be chosen based on how well the specific PPE fits the volunteer face model. For example, if the specific PPE fits the volunteer face model well, then the respective volunteer face model may be used.

In the selection phase, a specific PPE may be compared to a specific user model to determine a fit of the PPE with respect to a specific user model. A region of interest to receive the PPE may be defined on the user. The region of interest may be the face of the user. The region of interest may be captured and modeled in a 3D format. For example, a scanning device or image capture device may scan the face of the user and form a 3D model of the user's face through one or a series of images. A point cloud set may be defined on the 3D model of the user and semantic properties are applied to one or more of the defined points to generate a semantic face model as shown in step.

Also in the selection phase, a database may be accessed to retrieve a specific PPE model to be compared to the specific user model, where the PPE model has semantic properties as shown by respirator model. In an exemplary embodiment, the database may be populated in the offline phase with a multitude of PPE models each representative of a specific model and size PPE and each having semantic properties.

The respirator model and the face model may be aligned to determine a fit. For example, the respirator model may be superimposed upon the face model. The locations of the semantic properties of the respirator model and the face model may be then compared to determine a fit level of the respirator model to the face model as in step. In an exemplary embodiment, the distance between points on the respirator model and the user face model each having the same semantic properties may be determined for assessing a fit level of the respirator model to the user face model. Once an acceptable number of respirator models have been evaluated against the specific user face model, the respirator model having the best fit or highest fit level may be chosen for the specific user to wear as in step.

A final fit score determination process computes an overall fit score of PPE being virtually worn by a user, for example a 3D respirator model representative of a specific respirator being virtually worn by a 3D facial model representative of a specific user. In an exemplary embodiment, the determination process may include a graphical interface adapted for control by an administrator. For example, the administrator may individually control a variety of parameters to determine whether the 3D respirator model fits the 3D face model.

In some examples, determination of whether the respirator model fits the 3D face model may be determined in response to a calculated estimated level of comfort parameter, an estimated level of face-seal parameter, and an amount of dead space parameter. In an exemplary embodiment, the estimated level of comfort parameter may be a degree of comfort felt by the user calculated by evaluating a contacting portion of the respirator model against the face model. In an exemplary embodiment, the estimated level of face-seal parameter may be a calculated gap between a seal of the respirator model and the face model. In an exemplary embodiment, the amount of dead-space parameter may be a calculated internal distance between the respirator model and the face model.

Based on the parameters, a final fit score may be calculated. In an exemplary embodiment, the final fit score may be representative of how well the respirator model fits the face model, or the perceived feeling or comfort of the user while wearing the respirator. In an exemplary embodiment, a final fit score of 100% may be representative of a perfect fit of the respirator model on the face model, and a final fit score of 0% may be representative of a worst-case fit of the respirator model on the face model. In an exemplary embodiment, a final fit score of 75% may be representative of a very good fit of the respirator model on the face model and a final fit score of 25% may be representative of a below average fit of the respirator model on the face model.

In some examples, each parameter may be weighted by a predetermined weighted function to arrive at a parameter result. For example, the estimated level of comfort may have a weighted function of 0.4. Since the estimated level of comfort parameter for the particular respirator model may be 35%, for example, the parameter result may become 35%×0.4=14%. Each parameter result may be totaled to arrive at the final fit score. In an exemplary embodiment, the weighted function may be changed for a particular type of respirator or particular type of PPE. In another exemplary embodiment, the weighted function may be predetermined by the administrator or the user based on company or user preferences.

In some examples, a 3D representation of the respirator model being worn by the face model may be illustrated in the graphical interface for display to the user. In an exemplary embodiment, a screenshot or printout of a PPE fit result may be provided to the user.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, device driver, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs and PLDs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g/n, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are contemplated.

What is claimed is:

1. A non-transitory computer readable medium (CRM) tangibly embodying a Graphical User Interface (GUI) program and containing instructions that, when executed, cause a processor to perform operations to calculate a dead-space volume, the operations comprising:
receiving a three-dimensional facial model corresponding to a face of a person;
retrieving, from data memory locations, a three-dimensional mask model that includes a contacting interface configured to provide an integrity seal continuously circumscribing a nose and mouth region of the face;
superimposing the retrieved mask model onto the received facial model;
calculating a dead-space volume circumscribed by the contacting interface and located between the received facial model and the retrieved mask model when superimposed onto the received facial model;
associating a fit-quality metric with the calculated dead-space volume;
sending, for display on the display device, indicia representative of the associated fit-quality metric and indicia representative of the calculated dead-space volume.

2. The CRM of claim 1, wherein superimposing the retrieved mask model onto the received facial model comprises:
rotating the retrieved mask model with respect to the received facial model; and,
translating the retrieved mask model with respect to the received facial model.

3. The CRM of claim 1, wherein superimposing the retrieved mask model onto the received facial model comprises:
translating the retrieved mask model along a direction substantially toward or away from the facial model, wherein the translation distance is calculated to correspond with an actual translation of a mask subject to a force of a mask-securing device when securing a mask to a face.

4. The CRM of claim 1, containing further instructions that, when executed, cause a processor to perform operations comprising:
storing the retrieved mask model in a mask-model database.

5. The CRM of claim 1, containing further instructions that, when executed, cause a processor to perform operations comprising:
storing the received facial model in a facial-model database.

6. A non-transitory computer readable medium (CRM) tangibly embodying a Computer Program Product (CPP) and containing instructions that, when executed, cause a processor to perform operations to calculate a dead-space volume, the operations comprising:
receiving a three-dimensional facial model corresponding to a face of a person;
retrieving, from data memory locations, a three-dimensional mask model that includes a contacting interface configured to provide an integrity seal continuously circumscribing a nose and mouth region of the face;
superimposing the retrieved mask model onto the received facial model;
calculating a dead-space volume circumscribed by the contacting interface and located between the received facial model and the retrieved mask model when superimposed onto the received facial model; and
sending, for display on a display device, indicia representative of the calculated dead-space volume.

7. The CRM of claim 6, containing further instructions that, when executed, cause a processor to perform operations comprising:
associating a fit-quality metric with the calculated dead-space volume; and
sending, for display on the display device, indicia representative of the associated fit-quality metric.

8. The CRM of claim 6, containing further instructions that, when executed, cause a processor to perform operations comprising:
Sending, for display on a display device, image data representative of the face model with the mask model as superimposed onto the face model.

9. The CRM of claim 6, wherein superimposing the retrieved mask model onto the received facial model comprises:
rotating the retrieved mask model with respect to the received facial model; and,
translating the retrieved mask model with respect to the received facial model.

10. The CRM of claim 6, wherein superimposing the retrieved mask model onto the received facial model comprises:
translating the retrieved mask model along a direction substantially toward or away from the facial model, wherein the translation distance is calculated to correspond with an actual translation of a mask subject to a force of a mask-securing device when securing a mask to a face.

11. The CRM of claim 6, containing further instructions that, when executed, cause a processor to perform operations comprising:
storing the retrieved mask model in a mask-model database.

12. The CRM of claim 6, containing further instructions that, when executed, cause a processor to perform operations comprising:
storing the received facial model in a facial-model database.

13. The CRM of claim 6, wherein superimposing the retrieved mask model, calculating a dead-space volume, and sending indicia representative of the calculated dead-space volume are each repeated for a plurality of retrieved three-dimensional mask models.

14. The CRM of claim 6, wherein superimposing the retrieved mask model, calculating a dead-space volume, and sending indicia representative of the calculated dead-space volume are each repeated for a plurality of received three-dimensional facial models.

15. The CRM of claim 14, containing further instructions that, when executed, cause a processor to perform operations comprising:
sorting the calculated dead-space volumes; and,
sending, for display on a display device, the sorted calculated dead-space volumes.

16. A method for calculating a dead-space volume, the method comprising:
receiving a three-dimensional facial model corresponding to a face of a person;
retrieving, from data memory locations, a three-dimensional mask model that includes a contacting interface configured to provide an integrity seal continuously circumscribing a nose and mouth region of the face;

superimposing the retrieved mask model onto the received facial model;

calculating a dead-space volume circumscribed by the contacting interface and located between the received facial model and the retrieved mask model when superimposed onto the received facial model; and, sending, for display on a display device, indicia representative of the calculated dead-space volume.

17. The method of claim 16, wherein superimposing the retrieved mask model onto the received facial model comprises:

rotating the retrieved mask model with respect to the received facial model; and, translating the retrieved mask model with respect to the received facial model.

18. The method of claim 16, wherein superimposing the retrieved mask model onto the received facial model comprises:

translating the retrieved mask model along a direction substantially toward or away from the facial model, wherein the translation distance is calculated to correspond with an actual translation of a mask subject to a force of a mask-securing device when securing a mask to a face.

19. The method of claim 16, further comprising:

storing the retrieved mask model in a mask-model database.

20. The method of claim 16, further comprising:

storing the received facial model in a facial-model database.

* * * * *